(12) United States Patent
Younes

(10) Patent No.: US 7,484,508 B2
(45) Date of Patent: Feb. 3, 2009

(54) METHOD AND DEVICE FOR MONITORING AND IMPROVING PATIENT-VENTILATOR INTERACTION

(75) Inventor: Magdy Younes, Toronto (CA)

(73) Assignee: YRT Limited, Toronto, Ontario (CA)

( * ) Notice: Subject to any disclaimer, the term of this patent is extended or adjusted under 35 U.S.C. 154(b) by 1110 days.

(21) Appl. No.: 10/606,751

(22) Filed: Jun. 27, 2003

(65) Prior Publication Data

US 2004/0050387 A1 Mar. 18, 2004

Related U.S. Application Data

(60) Provisional application No. 60/391,594, filed on Jun. 27, 2002.

(51) Int. Cl.
*A61M 16/00* (2006.01)
(52) U.S. Cl. .................. 128/204.18; 128/204.21; 128/204.23
(58) Field of Classification Search ........... 128/204.18, 128/204.21, 204.23
See application file for complete search history.

(56) References Cited

U.S. PATENT DOCUMENTS

| | | | | |
|---|---|---|---|---|
| 5,319,540 A | * | 6/1994 | Isaza et al. .................... | 700/41 |
| 5,582,163 A | | 12/1996 | Bonassa | |
| 5,660,171 A | | 8/1997 | Fennema et al. | |
| 5,927,274 A | * | 7/1999 | Servidio et al. ........ | 128/204.18 |
| 6,105,575 A | * | 8/2000 | Estes et al. ............ | 128/204.23 |
| 6,305,374 B1 | * | 10/2001 | Zdrojkowski et al. .. | 128/204.21 |
| 6,439,229 B1 | * | 8/2002 | Du et al. ................ | 128/204.23 |
| 6,609,517 B1 | * | 8/2003 | Estes et al. ............ | 128/204.23 |

FOREIGN PATENT DOCUMENTS

WO WO 00/45881 8/2000

OTHER PUBLICATIONS

Giannouli et al., Am J Respir Crit Care Med., Jun. 1999; vol. 159(6):1716-25.
Leung, Philip et al. Comparison of assisted ventilator modes on triggering, patient effort, and dyspnea. vol. 155 pp. 1940-1948, 1997.
Yamada, Yoshitsugu and Du, Hong-Ling. Analysis of the mechanisms of expiratory asynchrony in pressure support ventilation: a mathematical approach. J. Appl Physiol vol. 88, pp. 2143-2150, 2000.
Younes, M. Patient-Ventilator Interaction with Pressure-Assisted Modalities of Ventilatory Support. vol. 14, pp. 299-322, 1993.

* cited by examiner

*Primary Examiner*—Danton DeMille
(74) *Attorney, Agent, or Firm*—Michael I. Stewart; Sim & McBurney

(57) ABSTRACT

Method and apparatus for non-invasively determining the time onset ($T_{onset}$) and end ($T_{end}$) of patient inspiratory efforts. A composite pressure signal is generated comprising the sum of an airway pressure signal, a gas flow pressure signal obtained by applying a gain factor ($K_f$) to a signal representing gas flow rate and a gas volume pressure signal obtained by applying a gain factor ($K_v$) to a signal representing volume of gas flow. $K_f$ and $K_v$ values are adjusted to result in a desired linear trajectory of composite pressure signal baseline in the latter part of the exhalation phase. The current composite pressure signal is compared with (i) selected earlier composite pressure signal values and/or (ii) value expected at current time based on extrapolation of composite pressure signal trajectory at specified earlier times and/or (iii) the current rate of change in the composite pressure signal with a selected earlier rates of change. The differences obtained by the comparison are compared with selected threshold values. $T_{onset}$ is identified when at least one of the differences exceeds the threshold values.

33 Claims, 32 Drawing Sheets

Generation of pressure and flow signals

US 7,484,508 B2

METHOD AND DEVICE FOR MONITORING AND IMPROVING PATIENT-VENTILATOR INTERACTION

REFERENCE TO RELATED APPLICATION

This application claims priority under 35 USC 119(e) from U.S. Provisional Patent Application No. 60/391,594 filed Jun. 27, 2002.

FIELD OF INVENTION

This invention relates to assisted mechanical ventilation.

BACKGROUND TO THE INVENTION

With assisted ventilation (e.g. assist volume cycled ventilation, pressure support ventilation and proportional assist ventilation) ventilator cycles are triggered by the patient and are intended to coincide with patient's inspiratory effort. In practice, however, the ventilator cycle never begins at the onset of patient's inspiratory effort (trigger delay) and the end of the ventilator's inflation phase only rarely coincides with the end of inspiratory effort (cycling-off errors). FIG. 1 provides an example. The bottom channel is transdiaphragmatic pressure (measured by esophageal and gastric catheters) and reflects true patient inspiratory effort. As may be seen, ventilator cycle was triggered several hundred milliseconds after onset of effort (interval between vertical lines) and the inflation cycle continued well beyond the effort. In fact, the ventilator was cycling almost completely out-of-phase with the patient. Trigger delay is often so marked that some efforts completely fail to trigger the ventilator (ineffective efforts, e.g. third effort, FIG. 1). A more advanced form of non-synchrony is shown in FIG. 2. In this case, the inflation cycle of the ventilator extends over two patient cycles. There are, accordingly, two inspiratory efforts within a single inflation phase and there is an additional ineffective effort during the ventilator's expiratory phase. The arrows in FIG. 2 indicate the location of the extra patient efforts that did not trigger corresponding ventilator cycles.

Non-synchrony between patient and ventilator is extremely common. Leung et al found that, on average, 28% of patient's efforts are ineffective (Leung P, Jubran A, Tobin M J (1997). Comparison of assisted ventilator modes on triggering, patient effort, and dyspnea. Am J Respir Crit Care Med 155:1940-1948). Considering that ineffective efforts are the extreme manifestation of non-synchrony, less severe, yet substantial (e.g. first two breaths, FIG. 1), delays must occur even more frequently. Non-synchrony is believed to cause distress, leading to excessive sedation and sleep disruption, as well as errors in clinical assessment of patients since the respiratory rate of the ventilator can be quite different from that of the patient. Monitoring respiratory rate is a fundamental tool for monitoring critically ill patients on ventilators.

In current mechanical ventilators, triggering occurs when flow becomes inspiratory (i.e.>0) and exceeds a specified amount, or when airway pressure decreases below the set PEEP (positive end-expiratory pressure) level by a specified amount. Trigger delay has two components. One component is related to ventilator trigger response and sensitivity. Thus, if the response of the ventilator is poor, triggering may not occur immediately when the triggering criteria are reached. Alternatively, the threshold for triggering may be set too high by the user. The component of trigger delay attributable to ventilator response and sensitivity is given by the interval between zero flow crossing (arrow, FIG. 1) and triggering (second vertical line). The response of modern ventilators has improved substantially over the past several years such that it is difficult to effect further improvements in this respect, and this invention does not contemplate any such improvements. This component of trigger delay can, however, still be excessive if the user sets an unnecessarily high threshold. This setting may be because of lack of sufficient expertise, or because there was excessive baseline noise at some point, which necessitated a high threshold to avoid auto-triggering. The threshold then remains high even after disappearance of the noise.

The second component of trigger delay is the time required, beyond the onset of inspiratory effort ($T_{onset}$), for expiratory flow to be reduced to zero (interval between first vertical line and the arrow, FIG. 1). This delay is related to the fact that expiratory resistance is usually high in ventilated patients and expiratory time is frequently too short to allow lung volume to return to FRC (functional residual capacity) before the next effort begins. At $T_{onset}$, therefore, elastic recoil pressure is not zero (DH, dynamic hyperinflation). Inspiratory effort must first increase enough to offset the elastic recoil pressure associated with DH before flow can become inspiratory, and/or before $P_{aw}$ (airway pressure) decreases below PEEP, in order to trigger the ventilator. By identifying the true $T_{onset}$, which is one aspect of the current invention, this component of trigger delay (usually the largest component, seen, for example, FIG. 1) can be essentially eliminated.

Cycling-off errors result from the fact that, except with Proportional Assist Ventilation, current ventilator modes do not include any provision that links the end of ventilator cycle to end of the inspiratory effort of the patient. In the most common form of assisted ventilation, Volume Cycled Ventilation, the user sets the duration of the inflation cycle without knowledge of the duration of patient's inspiratory effort. Thus, any agreement between the ends of ventilator and patient inspiratory phases is coincidental. With the second most common form, Pressure Support Ventilation, the inflation phase ends when inspiratory flow decreases below a specified value. Although the time at which this threshold is reached is, to some extent, related to patient effort, it is to the largest extent related to the values of passive resistance and elastance of the patient. In patients in whom the product [resistance/elastance], otherwise known as respiratory time constant, is high, the ventilator cycle may extend well beyond patient effort, while in those with a low time constant the cycle may end before the end of patient's effort (Younes M (1993) Patient-ventilator interaction with pressure-assisted modalities of ventilatory support. Seminars in Respiratory Medicine 14:299-322; Yamada Y, Du H L (2000) Analysis of the mechanisms of expiratory asynchrony in pressure support ventilation: a mathematical approach. J Appl Physiol 88:2143-2150).

In U.S. Pat. No. 6,305,374 B1, an approach is described to identify the onset and end of patient's inspiratory effort during non-invasive bi-level positive pressure ventilation (Bi-PAP). This approach relies exclusively on the pattern of flow waveform to make these identifications. Thus, current values of flow are compared with an estimated value based on projections from preceding flow pattern. If the difference exceeds a preset amount, a phase switch is declared. While this method may yield reasonably accurate results in the intended application (treatment of obstructive sleep apnea patients with non-invasive BiPAP), a number of considerations suggest that its use in critically ill, intubated, ventilated patients may not provide accurate results:

1) Implicit to the use of flow as a marker of respiratory muscle pressure output is the assumption that flow pattern reflects changes in alveolar pressure inside patient's lung.

This is where respiratory muscle pressure is exerted. This assumption, however, is true only if airway pressure is constant. Since airway pressure is one of the two pressure values that determine flow (flow=(airway pressure-alveolar pressure)/resistance), it is clear that changes in airway pressure can alter flow even if there is no change in respiratory muscle pressure. In non-invasive bi-level support, airway pressure, one of the two pressure values that determine flow, is reasonably constant during both inspiration and expiration, even though the absolute level is different in the two phases. If one of the two pressure values is constant during a given phase, it is reasonable to assume that changes in flow during that phase reflect changes in the other pressure, namely alveolar pressure. This condition does not apply in intubated, mechanically ventilated patients. In most modern intensive care ventilators, airway pressure is actively controlled during expiration through adjustments of the PEEP/exhalation valve mechanism. The pattern of such active changes in airway pressure during expiration varies from one ventilator brand to another and in the same ventilator from time to time depending on the state of the PEEP/exhalation valve mechanism. Under these conditions, changes in flow trajectory during expiration cannot be assumed to reflect changes in alveolar pressure trajectory. Likewise, during inspiration airway pressure is far from being constant, regardless of the mode used. Thus, changes in inspiratory flow profile cannot be used to reflect similar changes in alveolar pressure. The use of flow to infer end of effort during the inflation phase is accordingly not plausible.

2) When passive elastance (E) and resistance (R) are constant over the entire tidal volume range, the product R/E, or respiratory time constant, is also constant over the entire period of expiration. Because the time constant governs the pattern of lung emptying, a constant R/E produces a predictable exponential flow pattern in the passive system. With a predictable pattern it is possible to make forward extrapolations, or predictions, for the sake of identifying a deviation from the expected passive behaviour. Such deviation may then be used, with reasonable confidence, to infer the development of an additional active force, such as the onset of inspiratory muscle effort. When E and R are not constant throughout the breath, R/E may change from time to time causing changes in flow trajectory (Δflow/Δt) that are not related to muscle pressure. Under these conditions, deviation in Δflow/Δt from previous values cannot reliably signify a change in pressure generated by respiratory muscles. Patients with obstructive sleep apnea, the intended population of U.S. Pat. No. 6,305,374 B1, have generally normal lungs; R and E are expected to be constant over the tidal volume range, particularly when expiratory airway pressure is higher than atmospheric (i.e. the usual case when BiPAP is applied). In critically ill, intubated ventilated patients, this is not the case. Resistance is not constant, primarily because these patients are intubated and the resistance of the endotracheal tube is flow-dependent (the higher the flow, the higher the resistance). The relation between resistance and flow varies from one tube to the other. Furthermore, tidal volume in these patients often extends into the volume range where elastance is not constant. Thus, as the lung is emptying, either or both elastance and resistance may be changing, causing changes in respiratory time constant during the same expiration. Under these conditions, changes in flow trajectory need not reflect changes in respiratory muscle pressure. This considerably decreases the sensitivity and specificity of flow pattern as a marker of inspiratory effort.

3) Changes in respiratory muscle pressure ($P_{mus}$) are not exclusively used to change flow. According to the equation of motion, specifically applied to intubated patients:

$$P_{mus} = \text{Volume}*E + \text{Flow}*K_1 + (\text{Flow}*\text{absolute flow}*K_2) - P_{aw} \qquad \text{Equation 1}$$

Where, E is passive respiratory system elastance, $K_1$ is the laminar component of passive respiratory system resistance, $K_2$ is the resistance component related to turbulence (mostly in the endotracheal tube), and $P_{aw}$ is airway pressure which is determined by the pressure at the exhalation/PEEP valve ($P_{valve}$), flow and $R_{ex}$, that is resistance of the exhalation tubing ($P_{aw} = P_{valve} - \text{flow}*R_{ex}$). In this equation expiratory flow is negative. When $P_{mus}$ changes, as at $T_{onset}$, the flow trajectory should change. However, a change in flow trajectory also results in changes in volume and $P_{aw}$ trajectories. According to Equation 1, these changes will oppose the change in flow. For example, if expiratory flow decreases at a faster rate, volume decreases at a slower rate than in the absence of $P_{mus}$. At any instant after $T_{onset}$, elastic recoil pressure, which is related to volume, is higher, and this promotes a greater expiratory flow. The same can be said for the effect of changes in flow trajectory on $P_{aw}$ trajectory; a lower expiratory flow decreases $P_{aw}$, which promotes more expiratory flow. How much of the change in $P_{mus}$ is used to change the flow trajectory depends on the magnitude of the opposing forces. In particular, a higher passive elastance and/or a higher $R_{ex}$ tends to reduce the fraction of the change in $P_{mus}$ used to change flow trajectory. Furthermore, for a given $P_{mus}$ expended to change the flow trajectory, the actual change in trajectory is determined by resistance (i.e. $K_1$ and $K_2$). When E, $R_{ex}$, $K_1$ and $K_2$ are all low, a modest change in $dP_{mus}/dt$ results in a sharp change in flow trajectory. As these characteristics become more abnormal, the change in flow trajectory, for a given $dP_{mus}/dt$, progressively is attenuated. FIG. 3 illustrates this in a computer simulation.

In the example of FIG. 3, respiratory muscles were inactive in the first second of expiration (as they usually are). This is represented by $P_{mus}$ of zero (lower panel). At 1.0 sec an inspiratory effort begins. $P_{mus}$ rises at a rate of 10 cmH$_2$O/sec, representative of a normal respiratory drive. The three flow waveforms represent, from below upwards, progressively increasing values of $K_1$, $K_2$, E and $R_{ex}$. The values used in the lowest waveform are those of a patient with normal passive elastance and resistance, intubated with a large endotracheal tube (#9 tube, $K_2=3$), and exhalation tubing with a low resistance ($R_{ex}=2$). The onset of effort results in a sharp change in the flow trajectory that can be readily detected within a very short time after $T_{onset}$.

The middle waveform (FIG. 3) was generated with values representing the average intensive care patient on mechanical ventilation. Both passive $K_1$ and passive E are higher than normal, $K_2$ is that of a #8 endotracheal tube, the most common size used, and the exhalation tubing has a moderate (average) resistance. Note that the change in flow trajectory is considerably less pronounced. An experienced eye, with the benefit of hindsight (i.e. observing the flow waveform for a substantial period-after $P_{mus}$ started), may be able to tell that a change in trajectory occurred at 1.0 sec. However, it is not possible to prospectively identify that a trajectory change took place in a timely manner, for the sake of triggering the ventilator. Prospective identification of a trajectory change requires comparison between current and previous Δflow/Δt values, or between current flow values and values expected based on forward extrapolation of the preceding flow pattern (e.g. dashed lines, FIG. 3). There is always uncertainty with extrapolation, particularly with non-linear functions where the exact function is not known and, even more so, when the signal is noisy, as the flow signal commonly is (due to cardiac artefacts or secretions). Comparison of current and previous $\Delta$flow/$\Delta$t is also fraught with uncertainties when the rate may change for reasons other than respiratory muscle action (see #1 and #2, above). Thus, a wide difference (trigger threshold) must be specified, between current and projected flow, or between current and previous $\Delta$flow/$\Delta$t, before a trajectory change can be identified with confidence. Otherwise, false triggering will occur frequently. When the change in flow trajectory is: small, a longer interval must elapse before the threshold separation is achieved. It can be seen from the middle flow waveform that a conservative flow separation (between actual and projected flow) of 0.2 l/sec would not be reached until after flow became inspiratory. Thus, in the average mechanically ventilated patient the use of flow trajectory to identify $T_{onset}$ is not likely to result in a significant improvement. Over the current approach of waiting for flow to become inspiratory.

With more severe mechanical abnormalities (top waveform, FIG. 3), the change in flow trajectory is even more subtle. Even an experienced eye, with the benefit of hindsight, cannot distinguish between a true trajectory change and some flow artefact. Clearly, with a much stronger effort a flow trajectory change may be identifiable before flow becomes inspiratory. However, when patients have vigorous inspiratory efforts, there is no significant trigger delay even with current triggering techniques.

In summary, the use of flow to identify respiratory phase transitions is entirely unsuitable for identification of inspiratory to expiratory transitions during mechanical ventilation in critically ill patients (because of the highly variable $P_{aw}$ during inflation), and has poor sensitivity and specificity for identifying expiratory to inspiratory transitions in these patients because of the frequent use of active exhalation valves, the presence of variable time constant during expiration and the often marked abnormalities in elastance and resistance.

SUMMARY OF INVENTION

In one aspect, the present invention provides a method for detecting the onset of inspiratory effort ($T_{onset}$) in a patient on mechanical ventilation, comprising the steps of:

(a) monitoring airway pressure, rate of gas flow, and volume of gas flow of the patient;

(b) applying a gain factor ($K_f$) to the signal representing rate of gas flow to convert the gas flow signal into a gas flow pressure signal;

(c) applying a gain factor ($K_v$) to the signal representing volume of gas flow to convert the gas volume signal into a gas volume pressure signal;

(d) generating a composite pressure signal (signal) comprising the sum of airway pressure signal, gas flow pressure signal, and gas volume pressure signal, with all signals, having a suitably adjusted polarity;

(e) adjusting $K_f$ and $K_v$ to result in a desired linear trajectory of composite pressure signal baseline in the latter part of the exhalation phase;

(f) comparing (i) the current composite pressure signal values with selected earlier composite pressure signal values, and/or (ii) the current composite pressure signal values with values expected at current time based on extrapolation of composite pressure signal trajectory at specified earlier times, and/or (iii) the current rate of change in the composite pressure signal with a selected earlier rate of change in the composite pressure signal;

(g) comparing differences obtained from such comparison(s) made in step (f) with selected threshold values; and (h) identifying $T_{onset}$ when at least one of the differences exceeds the threshold values.

The composite pressure signal may contain a fourth component, consisting of the square of the rate of gas flow to which a gain factor ($K_{f2}$) is applied to convert the fourth signal to a pressure signal. $K_{f2}$ may also be used to adjust the trajectory of the composite pressure signal baseline in the latter part of the exhalation phase. $K_{f2}$ may be assigned a value corresponding to the $K_2$ constant of an endotracheal tube in the patient. The values of $K_v$, $K_f$ and/or $K_{f2}$ may be adjusted to result in a specified slope or pattern of the composite pressure signal during part or all of the expiratory phase.

A default value of $K_f$ may be used while the value of $K_v$ is adjusted to obtain a desired baseline composite pressure signal trajectory. Alternatively, a default value of $K_v$ is used while the value of $K_f$ is adjusted to obtain a desired baseline composite pressure signal trajectory.

The $K_f$ or $K_v$ value used may be a known or estimated value of the respiratory system resistance or elastance, respectively, of the patient.

The current composite pressure signal value may be compared with the composite pressure signal value at the most recent point where the composite pressure signal began a new rising phase and $T_{onset}$ is identified when the calculated difference exceeds a set threshold value.

$T_{onset}$ detection may be precluded in the early part of the exhalation phase.

The amplitude of the composite pressure signal may be monitored through the inspiratory phase and the end of inspiratory effort ($T_{end}$) is identified from a reduction in signal amplitude or signal slope below a specified value, which may be a specified fraction of the highest value obtaining during the inspiratory phase. $T_{end}$ detection may be precluded in the early part of the inflation phase. The generated signals corresponding to $T_{onset}$ may be used to trigger ventilation cycles and/or signals corresponding to $T_{end}$ may be used to cycle off ventilation cycles.

In another aspect of the invention, there is provided a method for detecting the onset of inspiratory effort ($T_{onset}$) in a patient on mechanical ventilation, comprising the steps of:

(a) monitoring airway pressure and rate of gas flow of the patient, (b) applying a gain factor ($K_f$) to the signal representing rate of gas flow to covert the gas flow signal into a gas flow pressure signal, (c) generating a composite pressure signal comprising the sum of airway pressure signal and the gas flow pressure signal, (d) comparing (i) the current composite pressure signal values with values expected based on extrapolation of composite pressure signal trajectory at specified earlier times, and/or (ii) the current rate of change of composite pressure signal with a selected earlier rate of change of composite pressure signal, (e) comparing differences obtained from such comparison(s) made in step (d) with selected threshold values, and (f) identifying $T_{onset}$ when at least one of the differences exceeds said threshold values.

In this aspect of the invention, the composite pressure signal may incorporate a third component consisting of the square of the rate of gas flow, to which a gain factor ($K_{f2}$) is applied to convert the third signal to a pressure signal. The selected $K_f$ may be a known or assumed value of respiratory system resistance.

The generated signal representing $T_{onset}$ may be used to trigger ventilation cycles.

The present invention further includes, methods for determining a suitable threshold value for identifying the onset of inspiratory effort from the composite pressure signal obtained according to the procedures described above.

In one such method, suitable for use where the composite pressure signal includes the sum of the airway pressure signal, gas flow pressure signal and gas volume pressure signal, and, optionally, the fourth component, comprises:

- monitoring the composite pressure signal over suitable intervals preceding onset of inspiratory effort, in a suitable number of elapsed breaths;
- identifying peaks and troughs in the composite pressure signal over the duration of the intervals;
- measuring the changes in signal amplitude between successive peaks and troughs, the amplitudes reflecting the range of amplitudes of noise included in the composite pressure signal; and
- determining from the detected range of noise amplitude, a value that exceeds the prevailing noise value, such value then being used prospectively to distinguish between true inspiratory efforts and noise.

Another such method, suitable for use where the composite pressure signal includes the sum of the airway pressure signal, gas flow pressure signal and gas volume pressure signal, and optionally, the fourth component, or where the composite pressure signal includes the sum of the airway pressure signal and the gas flow pressure signal, and optionally, the third component, comprising:

- monitoring the composite pressure signal over suitable interval preceding onset of inspiratory effort in a suitable number of elapsed breaths;
- determining slope of the composite pressure signal in successive subintervals within the intervals;
- measuring the range of slope in the subintervals, such range reflecting the range of slope change in composite pressure signal related to noise; and
- determining from the detected range of slope changes, a difference in slope that exceeds the prevailing noise level, the resulting value then being used prospectively to distinguish between changes in composite pressure signal slope due to inspiratory efforts and those due to composite pressure signal noise.

An alternative to the latter method comprises:

- monitoring the composite pressure signal over suitable intervals preceding the onset of inspiratory effort, in a suitable number of elapsed breaths;
- comparing signal amplitude at discrete points within such intervals with values predicted to occur at such times from the signal pattern in previous intervals, the difference in signal amplitude reflecting the range of difference related to composite pressure signal noise; and
- determining from the detected range of differences, a value that exceeds the prevailing noise level, such value then being used prospectively to identify differences between current and predicted values that reflect true inspiratory effort.

In another aspect of the present invention, there is provided a method for cycling off the inflation phase of a mechanical ventilator, which comprises:

- measuring the average interval between successive inspiratory efforts in a patient in a suitable number of elapsed breaths ($T_{TOT}$);
- identifying onset of inspiratory effort by utilizing any of the procedures provided in accordance with the present invention or otherwise;
- monitoring the time from the onset of inspiratory effort; and
- generating a signal that causes the ventilator to cycle off when time elapsed since onset of inspiratory effort exceeds a specified fraction of $T_{TOT}$.

The time to generate a signal to cycle off the ventilator may be calculated from the trigger time of current ventilation cycle plus a specified fraction of $T_{TOT}$.

In a further aspect of the present invention, there is provided a method for cycling off the inflation phase of a ventilator in pressure support ventilation, comprising:

- measuring the interval between successive inspiratory efforts in a suitable number of elapsed breaths ($T_{TOT}$);
- measuring inspiratory flow rate at specified times in the elapsed breaths which triggered ventilator cycles, the specified times corresponding to a fraction of the $T_{TOT}$, measured from the onset of inspiratory effort of each breath or from the trigger time of the ventilator;
- calculating the average of the flow values obtained at such specified times in the elapsed breaths; and
- generating a signal that causes the ventilator to cycle off when inspiratory flow in the current inflation phase decreases below said average flow value.

The results concerning patient ventilator interaction may be displayed in suitable format, including but not limited to a monitor, digital or electrical output ports, or printed material. Such results may include, but not limited to, display of the composite pressure signal, $T_{onset}$ and $T_{end}$ markers and displays regarding trigger delay, cycling-off errors, patient respiratory rate, number and frequency of ineffective efforts, and frequency and duration of central apneas, desirable duration of inflation phase, and flow at a specified fraction of $T_{TOT}$ of the patient in the pressure support ventilation mode.

In accordance with another aspect of the present invention, there is provided an apparatus for detecting the onset of inspiratory effort ($T_{onset}$) in a patient on mechanical ventilation, comprising:

- circuitry for measuring airway pressure, rate of gas flow and volume of gas flow of the patient;
- amplifier to apply a gain factor ($K_f$) to the signal representing rate of gas flow to convert the signal into a gas flow pressure signal;
- amplifier to apply a gain factor ($K_v$) to the signal representing volume of gas flow to convert the signal into a gas volume pressure signal;
- summing amplifier that generates a composite pressure signal comprising the sum of airway pressure signal, the gas flow pressure signal and the gas volume pressure signal, with all signals having suitably adjusted polarity;
- means to permit adjustment of $K_f$ and $K_v$ to provide a desired trajectory of composite pressure signal baseline in the latter part of the exhalation phase;
- circuitry to direct the composite pressure signal to a $T_{onset}$ identification circuitry during a suitable period in the expiratory phase, the identification circuitry comprising circuitry to detect a change in trajectory; and
- means for generating a signal corresponding to $T_{onset}$ when measured change in composite pressure signal trajectory exceeds a specified threshold.

In the device of the invention, an additional signal may be generated to be summed by the summing amplifier being generated by multiplying the flow signal by the absolute value of the flow signal and applying a gain factor ($K_{f2}$) to the resulting square flow signal using an amplifier and $K_{f2}$ is also used to adjust the trajectory of the composite pressure signal baseline in the latter part of the exhalation phase. $K_{f2}$ may be assigned a value corresponding to the $K_2$ constant of the endotracheal tube in place in the patient.

The $K_f$ value may be fixed at a default value while adjustment of signal trajectory is made using $K_v$ and/or $K_{f2}$. Alternatively, $K_v$ is fixed at a default value while adjustment of signal trajectory is made using $K_f$ and/or $K_{f2}$.

In one embodiment of the invention, the summing amplifier input related to volume of flow is omitted.

The device provided herein may include circuitry that precludes $T_{onset}$ identification during an adjustable period after the end of the inflation phase of the ventilator.

The $T_{onset}$ identification circuitry may comprise circuitry to obtain the rate of change of composite pressure signal amplitude and to obtain the difference between the current rate of change and the rate of change of the composite pressure signal amplitude at a specified earlier time and to generate a $T_{onset}$ signal when the difference exceeds a set threshold value.

The $T_{onset}$ identification circuitry may comprise circuitry to measure the difference between the current composite pressure signal amplitude and the composite pressure signal amplitude at a specified earlier time and to generate a $T_{onset}$ signal when the difference exceeds a set threshold value.

In the device of the invention, $K_v$ and/or $K_f$ and/or $K_{f2}$ may be adjusted to produce a horizontal or slightly downward sloping composite pressure signal baseline in the latter part of expiration and the $T_{onset}$ identification circuitry may comprise circuitry to measure the difference between current composite pressure signal amplitude and composite pressure signal amplitude at the most recent point where the composite pressure signal began rising and to generate a $T_{onset}$ signal when the difference exceeds a set threshold value.

The composite pressure signal may be gated to circuitry to identify end of inspiratory effort ($T_{end}$), such circuitry comprising:

circuitry to identify the highest amplitude (peak) of the composite pressure signal reached during the current inspiratory effort;

circuitry to detect when amplitude of the composite pressure signal decreases below a specified value beyond the time at which the peak occurred; and circuitry to generate a signal corresponding to $T_{end}$ when the amplitude of the composite pressure signal decreases below the specified value, which may be a specified fraction of the peak amplitude of the composite pressure signal. Circuitry may be provided to preclude detection of $T_{end}$ during a specified period following ventilator triggering.

Signal corresponding to $T_{onset}$ maybe used to trigger ventilator cycles and/or signal corresponding to $T_{end}$ may be used to cycle off inflation phases of the composite pressure signal.

The output of the device may be used for closed-loop control of ventilation setting. Functions executed by electrical circuitry may be executed in whole or in part by digital techniques.

In a further aspect of the present invention, there is provided a device for estimating a desirable duration of the inflation phase of a ventilator, comprising:

circuitry to identify inspiratory efforts of the patient, which may be a device according to the invention or by other suitable circuitry;

means to calculate the time difference between patient inspiratory efforts (patient $T_{TOT}$); and means for displaying a value corresponding to a specified fraction of patient $T_{TOT}$, such specified fraction being a user input or a default value between 0.3 and 0.5.

In this device, a signal may be generated to cycle off the inflation phase of the ventilator when the desirable duration has lapsed after ventilator triggering.

A signal may be generated to cycle off the inflation phase of the ventilator when the desirable duration has elapsed after onset of inspiratory effort in current breaths or after a point intermediate between onset of effort and ventilator triggering.

A user input may be provided for inputting patient $T_{TOT}$ or its reciprocal, patient respiratory rate, and the input then is used by the device, in lieu of device-determined patient $T_{TOT}$, to determine desirable duration of inflation phase.

In an additional aspect of the invention, there is provided a device for determining the desirable inspiratory flow threshold for terminating inflation cycles in the pressure support ventilation mode, comprising:

circuitry for estimating desirable duration of inflation phase of the ventilator, by using the device provided herein or by any other suitable alternative;

means for measuring inspiratory flow in recently elapsed breaths after the desirable duration has elapsed from the ventilator trigger time, or from the onset of inspiratory effort preceding triggered breaths, or from a specified point in between the two points; and means for displaying the value of said measured flow.

In such device, the value of the measured flow may be communicated to the cycling mechanism of the ventilator to effect termination of the inflation phase when the measured flow, or a reasonable approximate thereof, is reached during the inflation phase.

The values relating to patient ventilator interaction determined in the devices provided herein may be calculated and displayed in suitable format, including but not limited to a monitor, digital or electrical output ports. The values may be any of those discussed above.

The present invention, therefore, concerns a novel method and apparatus to, non-invasively, determine the true onset ($T_{onset}$) and end ($T_{end}$) of patient's inspiratory efforts. Such, method/device can be used simply as a monitor, informing the user of the presence and magnitude of trigger delays, ineffective efforts and cycling-off errors. The user can then take appropriate action to reduce the non-synchrony. Alternatively, the method/device can be coupled with the cycling mechanisms of the ventilator, whereby onset and end of ventilator cycles are automatically linked to onset and end of patient's efforts, thereby insuring synchrony without intervention by the user.

One aspect of the current invention is to minimize the cycling-off errors either by directly identifying the end of patient's inspiratory effort or by insuring that the ventilator's inflation phase does not extend beyond the physiologic limit of the duration of inspiratory effort.

DETAILED DESCRIPTION OF THE INVENTION

Figure 1:
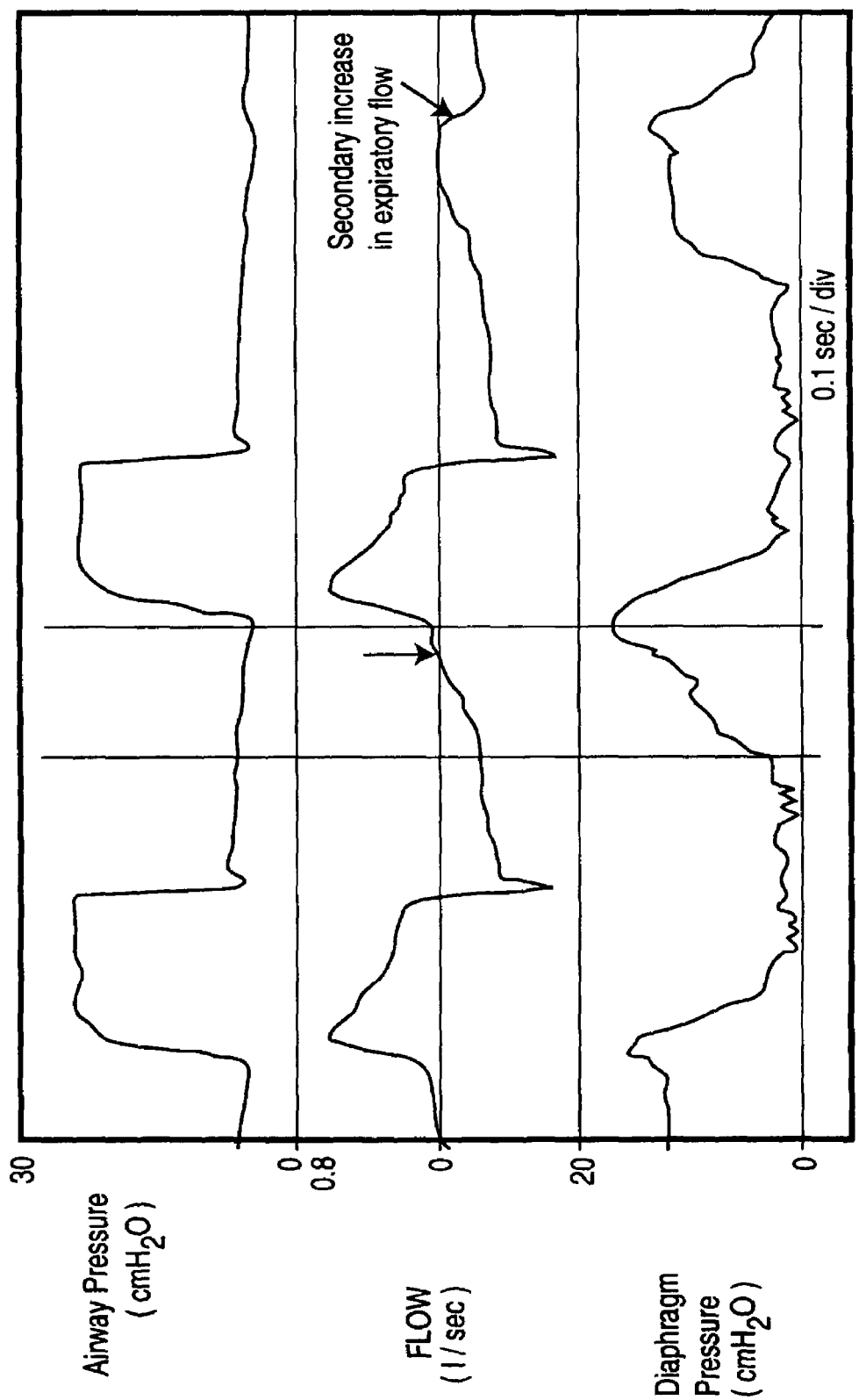
FIG. 1 contains traces of airway pressure, flow and diaphragm pressure for a patient on mechanical ventilation.

The present invention contemplates novel methods and devices for specific and timely identification of respiratory phase transitions within the patient for use in monitoring patient-ventilator interaction or to effect switching of ventilator cycles. These methods/devices represent a progression in complexity that address the problems inherent in the prior art ventilation procedures described above.

In the simplest of these methods, a signal is generated (signal X) that incorporates changes in both the flow and airway pressure ($P_{aw}$) signals. Thus, $$\text{Signal } X = (\text{Flow} * K_f) - P_{aw} \quad \text{Equation 2,}$$

where, $K_f$ is a constant that converts flow to pressure. $K_f$ may be an estimated or assumed value of patient's resistance (including endotracheal tube). There are two advantages to this approach: First, the signal becomes relatively immune to changes in flow trajectory produced via changes in pressure at the exhalation/PEEP valve mechanism (#1 in Background above). Thus, if pressure at the exhalation/PEEP valve increased near the end of expiration (to maintain PEEP), flow will decrease at a faster rate. Without the $P_{aw}$ component, this effect may appear as an inspiratory effort. With inclusion of $P_{aw}$ in the signal, changes in flow and $P_{aw}$ tend to cancel out. The extent to which this compensation is complete depends on how close $K_f$ is to actual patient resistance. In the absence of a known value, a default value may be used, for example 15 cmH$_2$O/l/sec, representing average resistance (including ET tube) in critically ill, mechanically ventilated patients. With such a default value, correction is not perfect, but the signal is more specific (than flow) in reflecting $T_{onset}$. Second, by including $P_{aw}$ in the signal, the signal incorporates that component of $P_{mus}$ that was dissipated against $R_{ex}$ (see #3 in Background). For example, if $P_{aw}$ decreases at $T_{onset}$ (because of the lower expiratory flow), this decrease is summed with the component related to flow, resulting in a sharper change in signal trajectory. With this approach, however, signal baseline prior to inspiratory effort is not flat, but, as in the case of flow, rises in a non-linear fashion. Forward extrapolation continues to be required to identify phase transition. Thus, the uncertainty associated with forward extrapolation is not eliminated but the change in signal trajectory is sharper, resulting in a more timely detection of $T_{onset}$ for the same selected detection threshold (i.e. difference between actual and predicted signal required for identification). Furthermore, this approach continues to be unsuitable for detection of inspiration to expiration transitions ($T_{end}$).

A further improvement is achieved by incorporating a component related to volume in the signal (signal Y). Thus:

$$\text{Signal } Y = \text{Volume} * K_v + \text{Flow} * K_f - P_{aw} \quad \text{Equation 3,}$$

where, $K_v$ is a factor that converts volume to pressure. With this treatment, the increase in the flow term during expiration (note that flow is negative) is offset by the decrease in the volume term. This tends to linearize, and decrease the slope of (flatten) the signal in the interval prior to $T_{onset}$, reducing the uncertainty associated with extrapolation, while the change in trajectory at $T_{onset}$ is rendered more acute on account of incorporating representation of all actions resulting from the change in $P_{mus}$ (see #3 in Background). In the best case scenario, where $K_v$ is identical to passive elastance, $K_f$ is identical to passive resistance, and there are no non-linearities in the passive pressure-flow and pressure-volume relations, signal Y would be identical to the actual $P_{mus}$ waveform, with a flat baseline and a crisp rising phase at $T_{onset}$ (i.e. as in the $P_{mus}$ panel of FIG. 3). Under these conditions, extrapolation is unnecessary, and phase transition is identified when signal Y exceeds a set threshold above the baseline value, to account for random baseline noise. Unfortunately, however, precise determination of actual passive properties during assisted ventilation is impossible, and there are non-linearities in the pressure-flow and pressure-volume relations. These result in some instability in baseline, necessitating the use of extrapolation. It may be expected, however, that the transition from baseline to active inspiration will be crisper after including a volume component (see below).

A further improvement is achieved by allowing for non-linearity in the pressure-flow relation. In mechanically ventilated patients, the non-linear element is almost exclusively due to endotracheal tube characteristics. Thus, a suitable alternate approach is to partition the flow component in two parts, one related to the endotracheal tube and the other related to a laminar component of resistance ($K_f$). Such signal is referred to as signal Z. Thus:

$$\text{Signal } Z = \text{Volume} * K_v + \text{Flow} * K_{f1} + (\text{Flow} * \text{absolute flow} * K_{f2}) - P_{aw} \quad \text{Equation 4,}$$

where $K_{f2}$ may be the commercially available $K_2$ value of the endotracheal tube in place. This treatment essentially eliminates any artifactual baseline instability related to non-linear pressure-flow behaviour, further reducing the need for extrapolation and enhancing the crispness of the transition.

As indicated earlier, precise estimates of E and $K_1$ are impossible to obtain during assisted ventilation. Passive E and R (including $K_1$) may be available from earlier determinations in which the patient was made passive. These values may be different from the current values, either because the ventilation conditions under which measurements were made were different, or true E and R (i.e. $K_1$) may have changed in the interim. Some techniques can be used to estimate E and R during conventional assisted ventilation, but these are not very reliable. An important issue, therefore, is the impact of differences between the $K_v$ and real E, and between $K_f$ and real resistance, on the baseline of the generated signals and on the sharpness of the transition.

Figure 3:
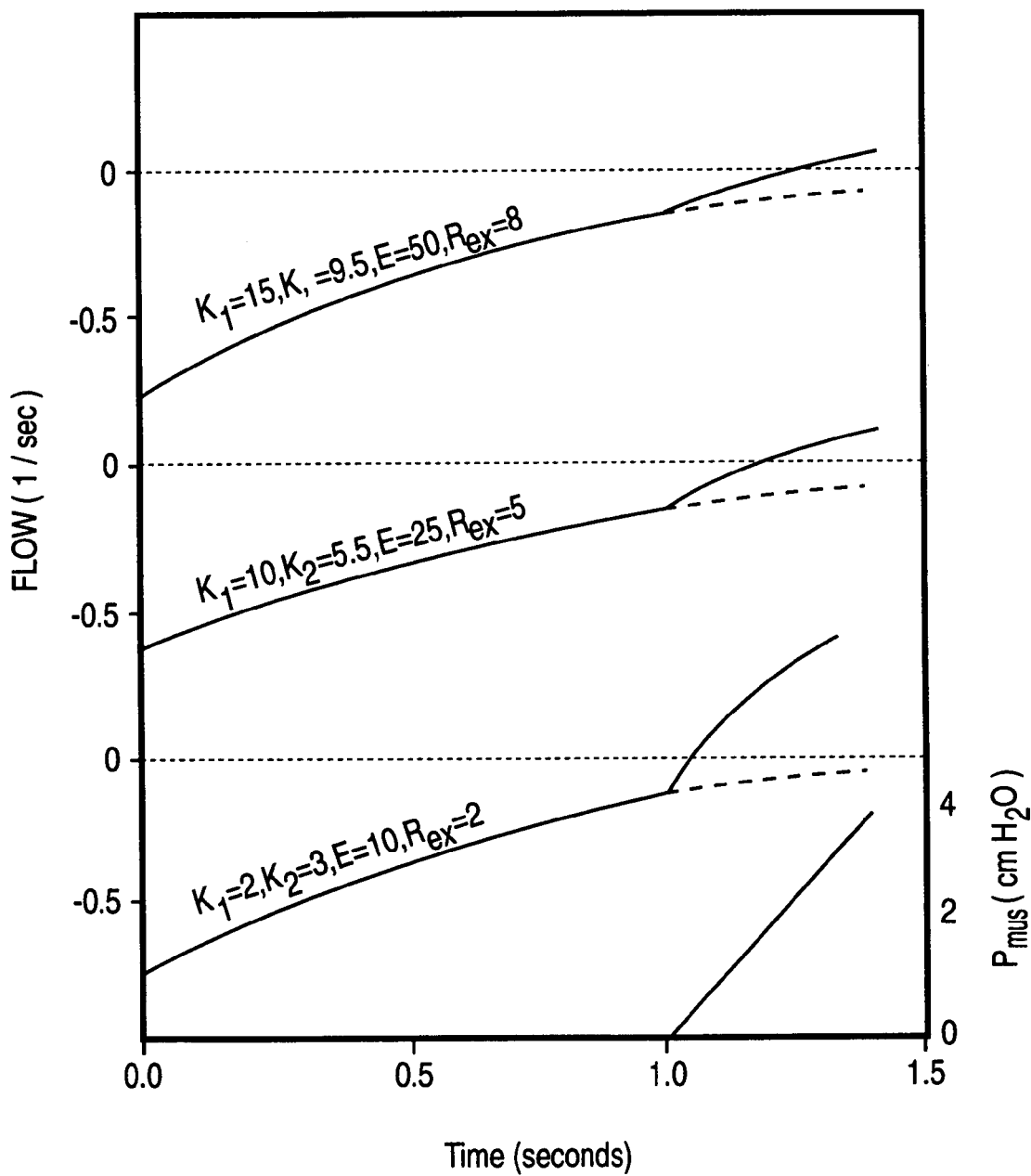
FIG. 3 is a graphical representation of the effect of variation in certain parameters on change in trajectory of flow upon start of inspiration.
Figure 4:
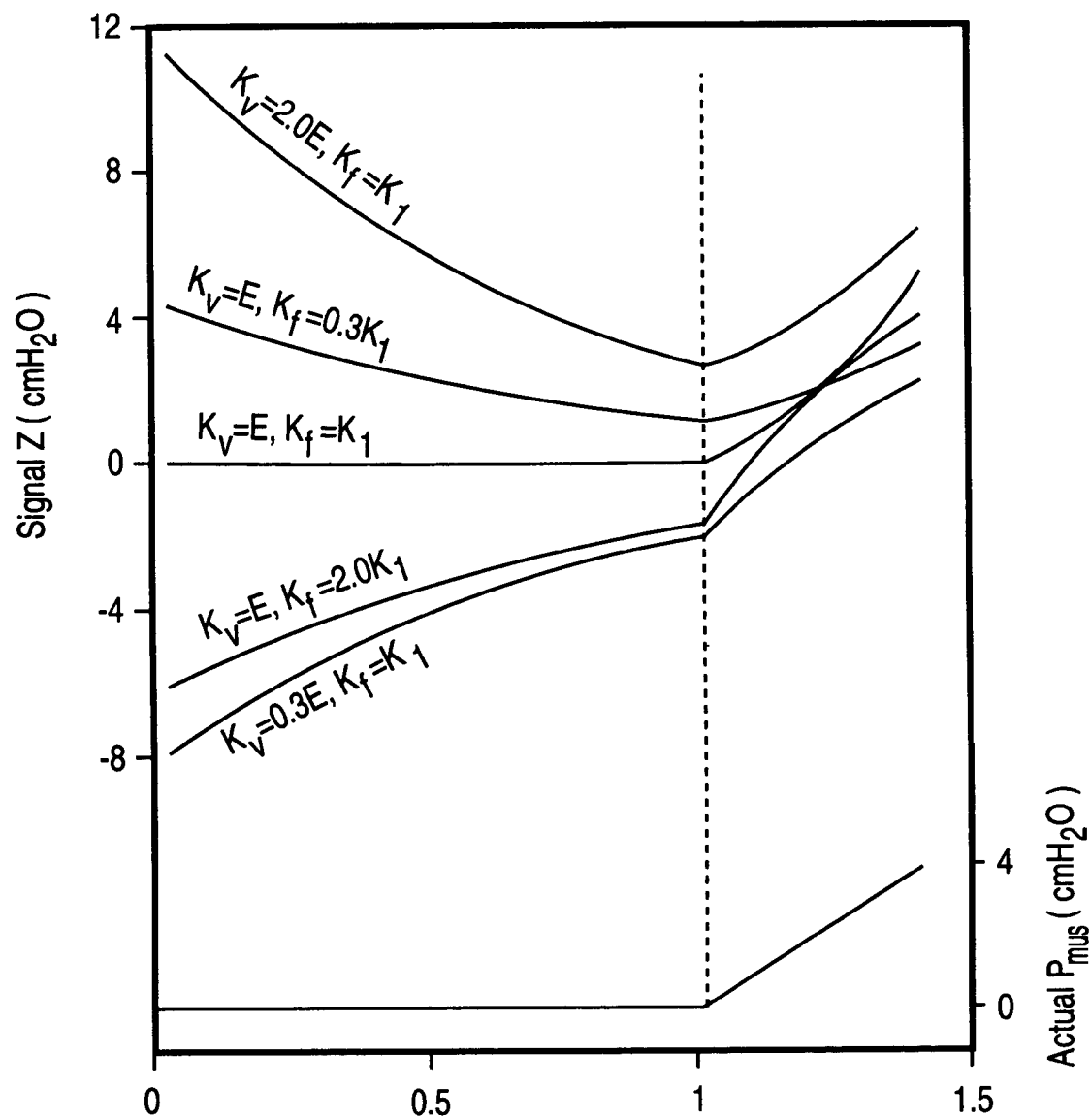
FIG. 4 is a graphical representation of the effect of variation in certain parameters on change in trajectory of composite pressure signal Z upon start of inspiration.

In FIG. 4, the same $P_{mus}$ waveform shown at the bottom of FIG. 3 was used to generate flow, volume and $P_{aw}$ waveforms using values representative of the average patient ($K_1$=10, $K_2$=5.5, E=25, $R_{ex}$=5, similar to the values used to generate the middle flow panel of FIG. 3). Signal Z was then generated from the resulting flow, volume and $P_{aw}$ waveforms using inaccurate values of $K_v$ and $K_f$ (i.e. $K_v$ different from real E and $K_f$ different from true $K_1$). Simulations were made with errors in either direction (over- or underestimation) of a magnitude that reflects reasonable outside limits of such errors in practice (i.e. E and $K_1$ overestimated by 100% or underestimated by 70%).

As may be expected, when there are no errors (i.e. $K_v$=E and $K_f$=K1, middle line, FIG. 4), signal Z is identical to the actual $P_{mus}$ waveform. However, when there are differences between assumed values and actual values, the baseline, prior to $T_{onset}$, is neither flat nor linear. When $K_v$ is >E, or $K_f$ is <$K_1$ (upper two lines), baseline is sloping down. Under these conditions, there is a qualitative change in direction of signal Z at $T_{onset}$ of effort. Such a directional change can be easily detected (e.g. by differentiating signal Z and looking for the point at which the differentiated signal becomes positive). However, when $K_v$ is <E, or $K_f$ is >$K_1$ (bottom two lines, FIG. 4), baseline is sloping up and $T_{onset}$ is evident as a change in slope; a quantitative, as opposed to the qualitative, difference observed with the opposite errors. To identify inspiratory effort under these conditions, as in the case of flow (FIG. 3), requires forward projection or extrapolation with the attendant increase in uncertainty and the necessity to increase trigger threshold. It should be noted, however, that with this approach (i.e. using signal Z (or Y) as opposed to flow) the change in trajectory is much sharper than in the case of flow (middle line, FIG. 3), making it possible to identify inspiratory effort sooner. It should also be noted that the upward slope of the signal, once effort begins, is related to the $K_f$ value, being higher when $K_f$ is higher than $K_1$, and vice versa.

It follows that the use of known values of E and $K_1$, obtained from previous direct measurement, offers advantages over the use of flow. However, under some conditions (i.e. baseline sloping upward) extrapolation techniques (or comparisons between current and previous rates of signal change) are required, and this may delay detection of phase transition.

A further novel aspect of this invention is to completely ignore patient values of E and $K_1$ and to simply select empiric values of $K_v$ and $K_f$ that result in a flat or slightly downward sloping baseline in the latter part of expiration. It is clear from FIG. 4 that, with respect to baseline pattern (i.e. pattern prior to inspiratory effort), errors can be made to cancel out. Thus, overestimation of E and overestimation of $K_1$ produce opposite errors. If empiric values of $K_v$ and $K_f$, that may have no bearing on actual values, are used, the baseline may be sloping up or down depending on the nature and magnitude of errors. Even though one cannot tell which value is in error, or by how much, it is always possible to obtain a flat baseline by adjusting either $K_f$ or $K_v$. For example, if using the empiric values results in an upward sloping baseline, the baseline can be made flat by increasing the empiric $K_v$ or decreasing the empiric $K_f$. If such adjustments result in a flat baseline but some systematic non-linearities persist, these can be offset by adjustments of the non-linear $K_{f2}$ term, if signal Z is used, resulting in a flat, and linear baseline. Under such conditions, identification of $T_{onset}$ presents little difficulty. A particularly suitable approach for generating signal Z is to use a default $K_f$ value of 10 cmH$_2$O/l/sec (15 if signal Y is used) and adjust $K_v$ to obtain a flat signal baseline. Alternatively, a default $K_v$ value (e.g. 25 cmH$_2$O/l, representing average elastance in ICU patients) is used and $K_f$ is adjusted to obtain a flat signal baseline. The former approach was found preferable by the inventor as it guarantees a fairly brisk rate of signal rise at $T_{onset}$. Adjustments of $K_v$ at a set $K_f$, or vice versa, can be implemented by the user employing external inputs for $K_v$, and/or $K_f$, with feedback from a graphic display of the generated signal (signal Y or Z). Alternatively, selection of the optimum $K_v$ and $K_f$ values may be done automatically using appropriate software.

The above approach does not address the possibility of non-linear passive pressure-volume relation in the tidal volume range (i.e. non-constant elastance). When this is present, and it is common in mechanically ventilated patients, the respiratory system is stiffer in the higher part of the tidal range. When $K_v$, which is a constant, is adjusted to produce a flat or slightly decreasing signal in the latter part of expiration the signal is not flat in the early part of expiration. In the presence of non-constant elastance (higher elastance at higher volumes) the signal shows a rising phase in the early part of expiration that continues until volume reaches the range of constant elastance. This artifactual rising phase may cause false identification of a new inspiratory effort. This problem is averted by "blinding" the $T_{onset}$ detection circuitry to the signal during the early part of expiration. This can be done, for example, by gating the signal to the $T_{onset}$ detection circuitry only after a certain delay from onset of expiratory flow ($T_{onset}$ window delay). Alternatively, the $T_{onset}$ detection circuitry may continue to detect $T_{onset}$ during this period but the resulting identification is gated out during this period; Detection of these false triggers can be easily recognized visually by their consistent relation to end of ventilator cycle. The magnitude of the delay (blinding or blanking period) can then be adjusted accordingly. Alternatively, software algorithms can be developed to detect triggering signals with a consistent relation to end of ventilator cycle and automatically adjusting the width of the window.

Figure 5:
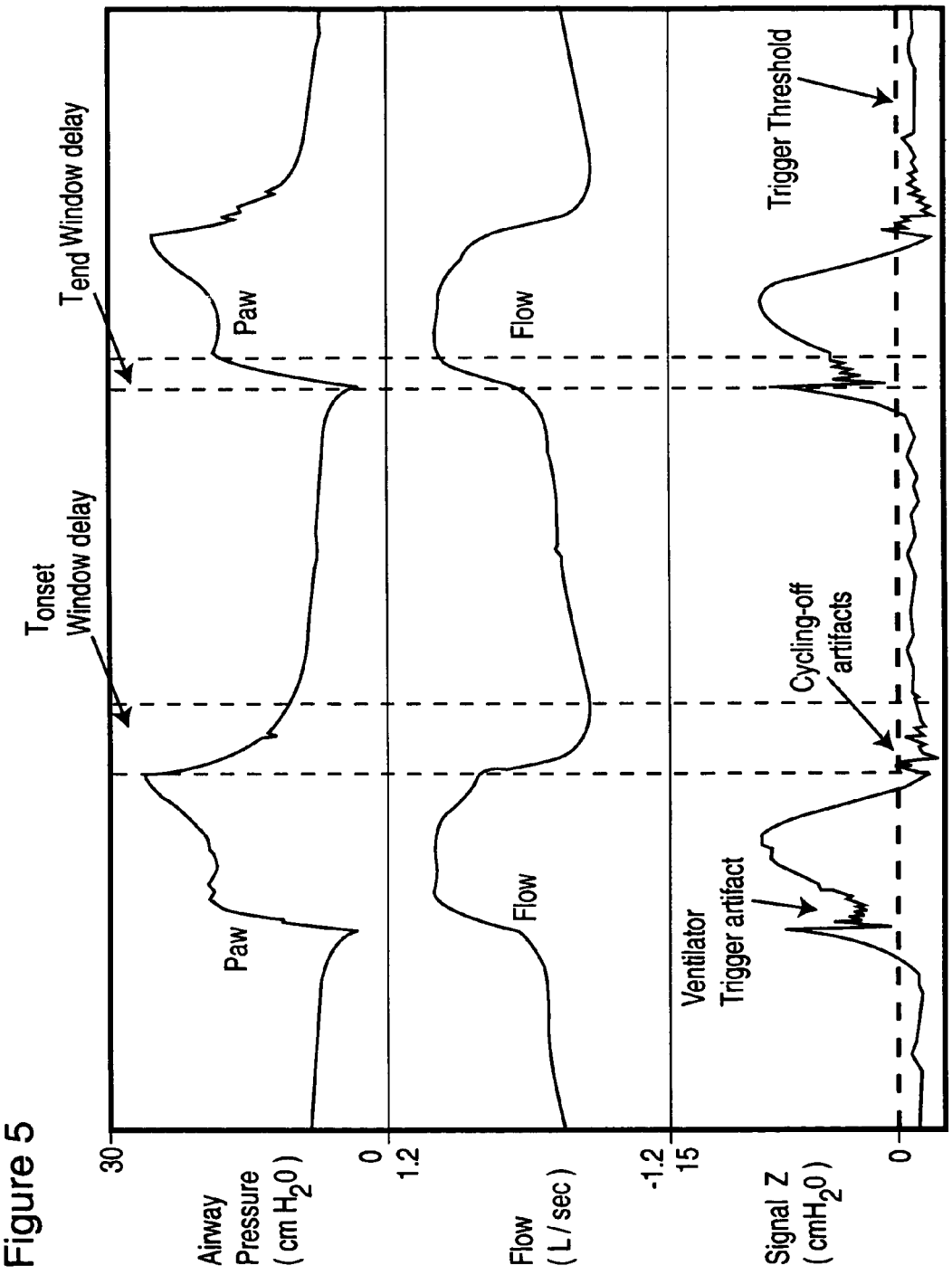
FIG. 5 contains traces of airway pressure, flow and composite pressure signal Z calculated in accordance with the invention.

The approach of blinding the $T_{onset}$ detection circuitry to the signal over a time zone close to ventilator cycling-off, where flow is changing rapidly, also helps weed out false triggers related to other artifacts that commonly occur in the signal at this time (see Cycling-off Artifacts, FIG. 5). These are related to acceleration pressure losses, which are difficult to compensate for, or to phase delays between pressure and flow signals, which are common in this setting, among other factors.

It should be pointed out that the selected values of $K_v$ and $K_f$ may have little to do with actual patient elastance and resistance. These values are simply used to facilitate detection of phase transitions. As such the actual value of the signal does not reliably reflect actual $P_{mus}$, and such signals cannot be used to reliably estimate the work of breathing or quantitative level of pressure output by the patient.

Figure 6:
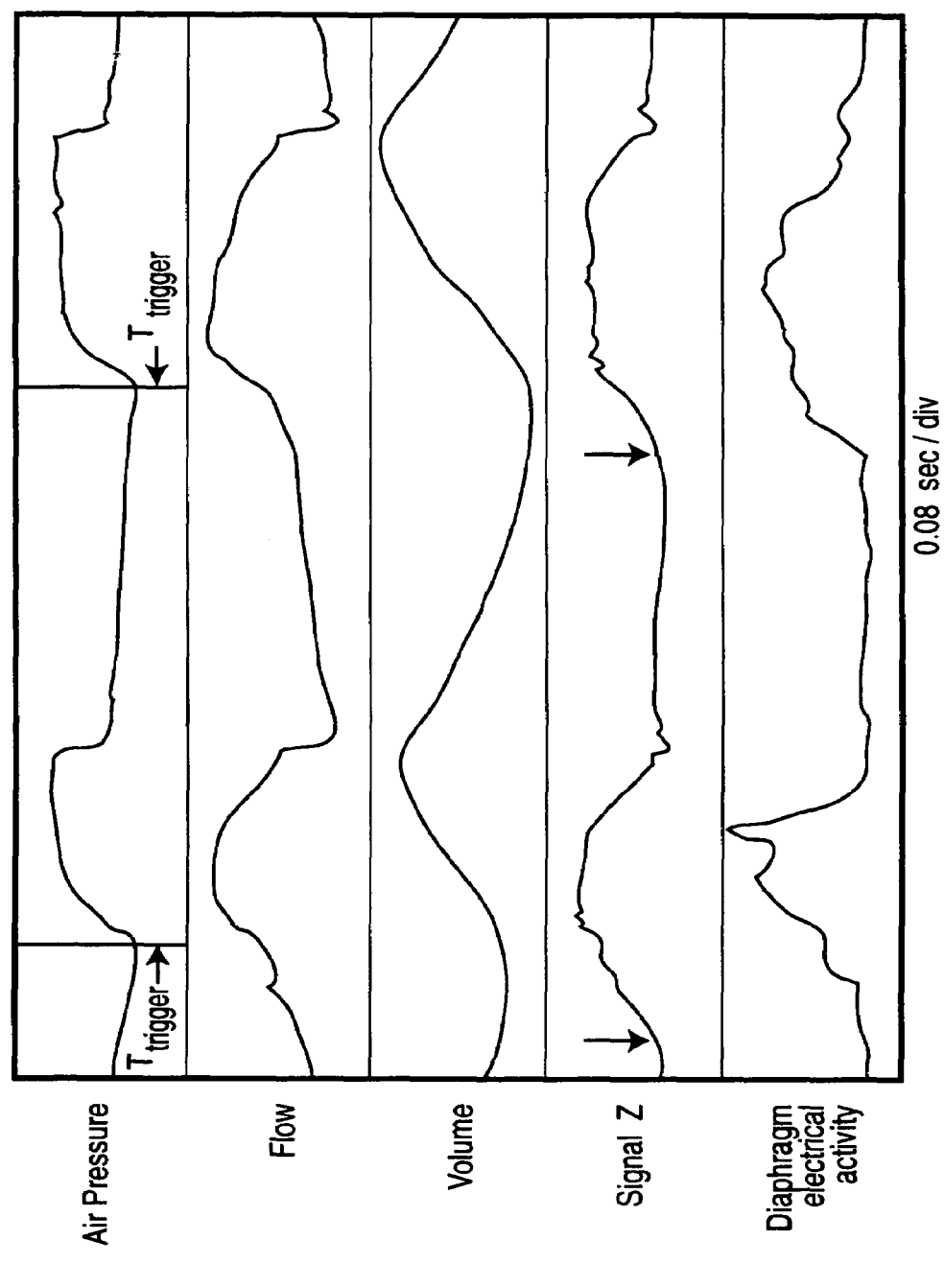
FIG. 6 contains traces of airway pressure, flow, composite pressure signal Z and diaphragm electrical activity, with the signal Z tracing being generated from pressure, flow and volume tracings.

FIG. 6 shows an example of signal Z generated from pressure, flow and volume tracings. The signal was generated using a default $K_f$ of 10, $K_{f2}$ of 5.5 (ET tube #8) and a $K_v$ of 30.5 selected because it produced a flat baseline in the latter part of expiration. Note the flat baseline of signal Z in the latter part of expiration. In this patient, diaphragmatic electrical activity was also monitored (lowest tracing), and this reflects the activity of the main inspiratory muscle. Note the excellent agreement between the onset of effort identified from the signal Z (arrows) and the onset of diaphragm electrical activity. Note also that $T_{onset}$ (arrows) was identified much earlier than the time at which the ventilator triggered with a conventional triggering algorithm ($T_{trigger}$, top channel).

A number of approaches can be used to identify a change in signal trajectory indicative of E→I transition ($T_{onset}$). Some of these include:

a) Differentiating the signal ($\Delta$signal/$\Delta$t) and comparing current values with values obtained earlier. $T_{onset}$ is identified when the difference exceeds a specified amount.
b) Comparing current values of signal with predicted values obtained from forward projection of previous signal trajectory. $T_{onset}$ is identified when the difference exceeds a specified amount.
c) Comparing current values of signal with values obtained earlier. $T_{onset}$ is identified when the difference exceeds a specified amount.
d) Preferred approach: Differentiating the signal ($\Delta$signal/$\Delta$t) and identifying points where $\Delta$signal/$\Delta$t crosses zero in a positive direction ($t_0(+)$). The change in signal amplitude, relative to amplitude at the immediately preceding $t_0(+)$, is continuously calculated. $T_{onset}$ is identified when the difference between current value and value at the preceding $t_0(+)$ exceeds a specified amount (threshold). If the difference does not reach threshold by the time $\Delta$signal/$\Delta$t crosses zero in a negative direction ($t_0(-)$), the difference is reset to zero, until the next $t_0(+)$. This approach has the advantage of filtering out slow, random undulations in baseline signal without altering the relation between signal and inspiratory effort (which would occur if a simple high pass filter were used). Such slow, random undulations in baseline signal may be produced, for example, by changes in thoracic blood volume, imperfect compensation for mechanical non-linearities, or random changes in respiratory muscle tone unrelated to phase transitions. The same approach can also be used to estimate the amplitude of higher frequency baseline noise (e.g. due to cardiac artifacts or secretions, see below). Such information can then be used to automatically adjust the threshold for identifying $T_{onset}$.

Regardless of which approach is used to identify $T_{onset}$ (a-d, above, or other approaches), a threshold must be set for the magnitude of change that must be reached for $T_{onset}$ to be declared. Several methods can be used to select such threshold. Some of these include:

i) A fixed threshold is arbitrarily selected. For example, with approach (d), a signal increase, beyond the latest $t_0(+)$, of 2 cmH$_2$O may be used under all conditions. Appropriate values may be chosen for other approaches. Although feasible, when a universal threshold is used, the value must be sufficiently high to avoid false auto-triggering under all circumstances. Since noise level varies from patient to patient, and from time to time, such a universal threshold would have to be set to a level that is unnecessarily high under most conditions.
ii) Threshold may be individually selected by the user via external controls. This can be achieved by the user selecting a value that results in minimal auto-triggering. Alternatively, with the help of graphical display of the signal, the user may adjust the threshold above baseline noise level (e.g. horizontal dashed line, FIG. 5).
iii) Software algorithms can be developed to distinguish noise from efforts and automatically adjust the threshold accordingly.

The preceding account focussed primarily on identification of E→I transitions. However, once $K_v$ and $K_f$ are selected to produce a nearly flat baseline during expiration, the shape of the signal during inspiration (but not necessarily its amplitude, see above) provides a reasonable approximation of the shape of inspiratory muscle output ($P_{mus}$) (for example, see FIG. 6). End of inspiratory effort ($T_{end}$) is normally defined as the point at which inspiratory muscle output rapidly declines from its peak value. To implement this definition, the highest value of signal Y (or Z) during the inflation phase can be identified, in real time, using any of a number of standard techniques. $T_{end}$ is identified when the signal decreases below a specified value or a specified fraction of peak value.

At times, the signal undergoes a transient artifactual reduction soon after ventilator triggering. An extreme example is shown in FIG. 5 (arrow indicating Ventilator Trigger Artifact). It is recognized as an artifact, as opposed to natural end of effort ($T_{end}$), because the signal resumes rising again. The presence of these artifacts may cause false identification of $T_{end}$. To avoid this, if false $T_{end}$ identification occurs, the $T_{end}$ identification circuitry is "blinded" to the signal for a set period after $T_{trigger}$ (see $T_{end}$ Window Delay, FIG. 5) in the same way the $T_{onset}$ identification circuitry is "blinded" to the signal soon after ventilator cycling-off. Distinction between artifactual and true $T_{end}$ can be easily made by the consistent occurrence at $T_{trigger}$ and the secondary rise in signal that characterize false $T_{end}$s. The distinction can be made by the user with the help of a monitor displaying the signal, or by using software algorithms. The width of the $T_{end}$ Window delay is adjusted accordingly.

At times, true $T_{end}$ occurs soon after ventilator triggering. This is because inspiratory muscle activity can be inhibited if inspiratory flow is high, and the ventilator frequently delivers excessive flow soon after triggering. For this reason, the procedure described above for $T_{end}$ identification may, if used to cycle off the ventilator, result in medically unacceptable inflation times. A back-up procedure is, therefore, required to insure that the duration of inflation phase is physiologically appropriate. The same procedure can be used to insure that the inflation phase does not extend beyond physiologically sound limits. The following is the rationale and method for ensuring that the duration of the inflation phase remains within physiologic limits.

Figure 2:
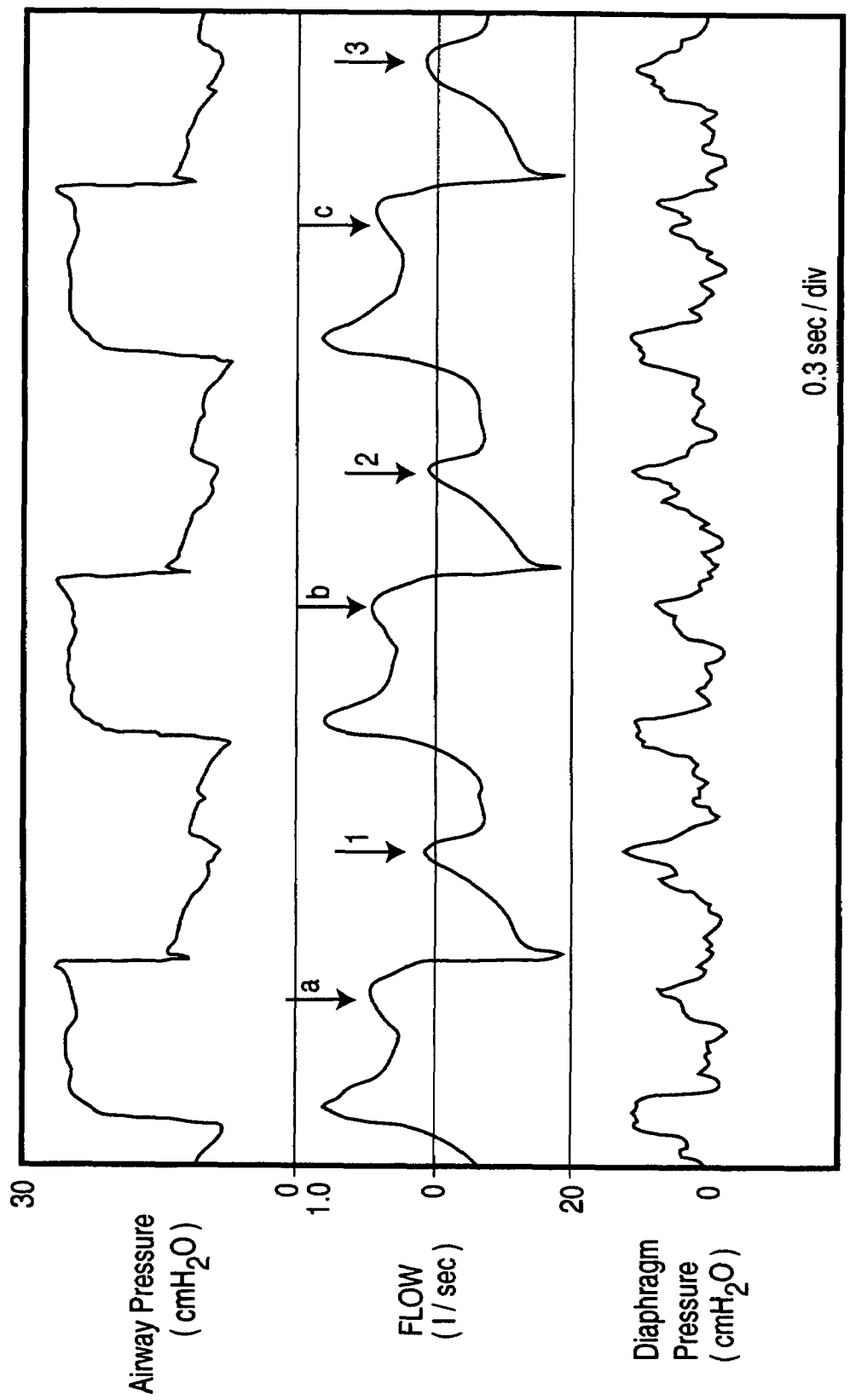
FIG. 2 contains further traces of airway pressure, flow and diaphragm pressure for ventilator cycles.

In spontaneously breathing subjects and patients, the duration of the inspiratory phase ($T_I$) ranges between 25% and 50% of respiratory cycle duration ($T_{TOT}$). In studies by the inventor using proportional assist ventilation (PAV), with which the duration of the ventilator's inflation phase mirrors the patient's own $T_I$, the ratio of $T_I$ to $T_{TOT}$ ($T_I/T_{TOT}$ ratio) was also found to be between 0.25 and 0.5. Therefore, one approach to insure that the duration of the inflation phase is within the physiologic range in modes in which end of ventilator cycle is not automatically synchronized with the patient is to constrain the duration of the inflation phase to be between 0.25 and 0.5 of the total cycle duration of patient's own efforts (to be distinguished from duration of ventilator cycles). Accordingly, in another aspect of this invention, the end of the ventilator cycle is constrained to occur within this physiological range. Implementation of this procedure requires knowledge of the true respiratory rate of the patient (as opposed to ventilator rate). The true rate of the patient is the sum of ventilator rate, the number of ineffective efforts occurring during the ventilator's exhalation phase (arrows 1 to 3, FIG. 2) and the number of additional efforts occurring during inflations triggered by an earlier effort (arrows a to c, FIG. 2). The above-described method for identifying $T_{onset}$ detects ineffective efforts occurring during the ventilator's exhalation phase. These can be added to ventilator rate. It may also be possible to identify extra efforts occurring during the inflation phase of the ventilator (a,b,c, FIG. 2) from the generated Y or Z signals. A simpler approach, however, that is particularly suited for pressure support ventilation, is to identify points in time at which flow begins rising again during the inflation phase (FIG. 2). In pressure support, flow typically declines progressively in the latter part of inflation. The only possible explanation for a secondary rise in flow, that is sustained for a significant duration (e.g. >0.3 second) is the occurrence of a second effort during inflation (described by Giannouli et al, American Journal of Respiratory and Critical Care Medicine, vol. 159, pages 1716-1725, 1999). Identification of the extra efforts during the inflation or exhalation phase can be made visually by the user (FIG. 2). Alternatively, it can be done automatically using software or analog circuitry. There are several possible approaches to automatically obtain the number of extra efforts that did not result in separate ventilator cycles. One such approach is to differentiate the flow signal and determine the number of positive and negative zero crossings of substantial duration (e.g. >0.4 second, to distinguish from high frequency noise and cardiac artefacts). Another approach is to use Fourier frequency analysis of the flow signal. There are clearly other mathematical approaches to identify the characteristic flow transitions associated with additional efforts. Thus, it is evident that there are many ways by which true respiratory rate of patient can be determined.

Once the true respiratory rate of patient is known, it becomes possible to calculate the real duration of respiratory cycles of the patient ($T_{TOT}$=60/respiratory rate) and determine the range of inflation times consistent with a physiologic $T_I/T_{TOT}$. For example, if patient's rate is 30/min, $T_{TOT}$ is 2.0 seconds and the physiologic range for the inflation phase is 0.5 to 1.0 second, reflecting a $T_I/T_{TOT}$ range of 0.25 to 0.50. Thus, according to this aspect of the invention, average $T_{TOT}$ is determined using any of a number of possible methods. The desirable duration of the ventilator's inflation phase is then determined by multiplying $T_{TOT}$ by a user selected physiologic $T_I/T_{TOT}$ ratio or a suitable default value (e.g. 0.4). In another implementation of this method, a timer is reset at the onset of a new $T_{onset}$ or a new ventilator cycle. The ventilator ignores other cycling-off commands so long as time elapsed since the last $T_{onset}$, or onset of ventilator cycle, is less than a set value (e.g. 0.3 of $T_{TOT}$). Similarly, to guard against excessively long ventilator cycles, the timer may send a cycling-off command once time, since the last $T_{onset}$ or onset of inflation phase, exceeds a set fraction of average $T_{TOT}$ (e.g. 0.45). The fractions used for minimum and/or maximum cycling-off time can be fixed within the ventilator or adjustable by the user.

An adaptation of this last aspect of the invention is particularly suited for pressure support ventilation (PSV). Because there is often some breath by breath variability in $T_{TOT}$, setting the end of ventilator cycle to a fixed fraction of average $T_{TOT}$ results in some cycles having higher, and other cycles having lower, $T_I/T_{TOT}$ ratios. In this aspect of the invention, only applicable to PSV, rather than causing the ventilator to cycle-off at a predetermined time from the last $T_{onset}$, the ventilator is cycled off when inspiratory flow reaches a specified amount, with this specified amount selected to provide, on average, the specified $T_I/T_{TOT}$. This aspect of the invention is implemented as follows: The interval between successive inspiratory efforts ($T_{TOT}$) is determined in several elapsed ventilator cycles. The level of inspiratory flow at the specified $T_I/T_{TOT}$ fraction is noted. For example, if the specified (desired) fraction is 0.4, and $T_{TOT}$ is 3.0 seconds, flow is measured at 1.2 second after the preceding $T_{onset}$ which triggered a ventilator cycle or, optionally, after the trigger time of the relevant ventilator cycle. The average of several such determinations, in several elapsed breaths, is used as the cycling-off flow threshold in subsequent breaths. With this approach, current cycles destined to have long $T_{TOT}$ automatically have longer inflation cycles. This is so because there is normally a correlation between the duration of inspiratory muscle activity and the $T_{TOT}$ of individual breaths. Thus, in breaths destined to have a long $T_{TOT}$, inspiratory activity tends to last longer and this, in PSV, delays the point at which a specified cycling-off flow threshold is reached.

The information provided by the present invention can be utilized in a number of ways: First, the time of $T_{onset}$, generated by the current invention, can be used to trigger ventilator cycles by providing an appropriate signal to the ventilator's triggering mechanism. Second, the end of the ventilator inflation phase can be made to coincide with the end of patient effort, as identified by the present invention, through appropriate connections to the cycling-off mechanism of the ventilation. Third, cycling-off can be made to occur at specified times or, in the case of pressure support ventilation, at a specified flow rate, after $T_{onset}$ or after the onset of ventilator cycle. In this application, the user enters a desired $T_I/T_{TOT}$ ratio. The appropriate time, or flow, to cycle-off is then determined from the inputted $T_I/T_{TOT}$ ratio and the value of average patient $T_{TOT}$, obtained using the present invention. Fourth, cycling off may occur at the identified $T_{end}$, conditional on this not violating a specified minimum $T_I/T_{TOT}$ ratio.

Whether or not it is used to synchronize the ventilator with patient effort, the information provided by the current invention can be displayed to the user to assist him/her in adjusting ventilator settings to, indirectly, improve patient ventilator interaction. In this connection, the information may be printed out on command or be displayed on a monitor. The signal itself can be displayed in real time along with other useful signals such as flow and airway pressure. In addition, numerical values concerning patient ventilator interaction can be displayed. Some recommended values include:

a) Trigger delay (difference between ventilator trigger time and $T_{onset}$).
b) Cycling-off error (difference between ventilator cycling-off time and end of inspiratory effort).
c) True respiratory rate of patient (number of inspiratory efforts per minute).
d) Average duration between inspiratory efforts ($T_{TOT}$).
e) Number of ineffective efforts, per minute or as a fraction of respiratory rate. This is calculated as the difference between true rate of the patient and ventilator rate.
f) Number of central apneas (no inspiratory efforts for a specified period, for example 10 seconds) per hour, and/or % of time spent in central apnea.
g) Flow at a specified fraction of average $T_{TOT}$ in the pressure support ventilation mode.

The numerical values may be accompanied by displayed suggestions on how to adjust ventilator settings to reduce the undesirable aspects of current interaction.

DESCRIPTION OF PREFERRED EMBODIMENT

Figure 7:
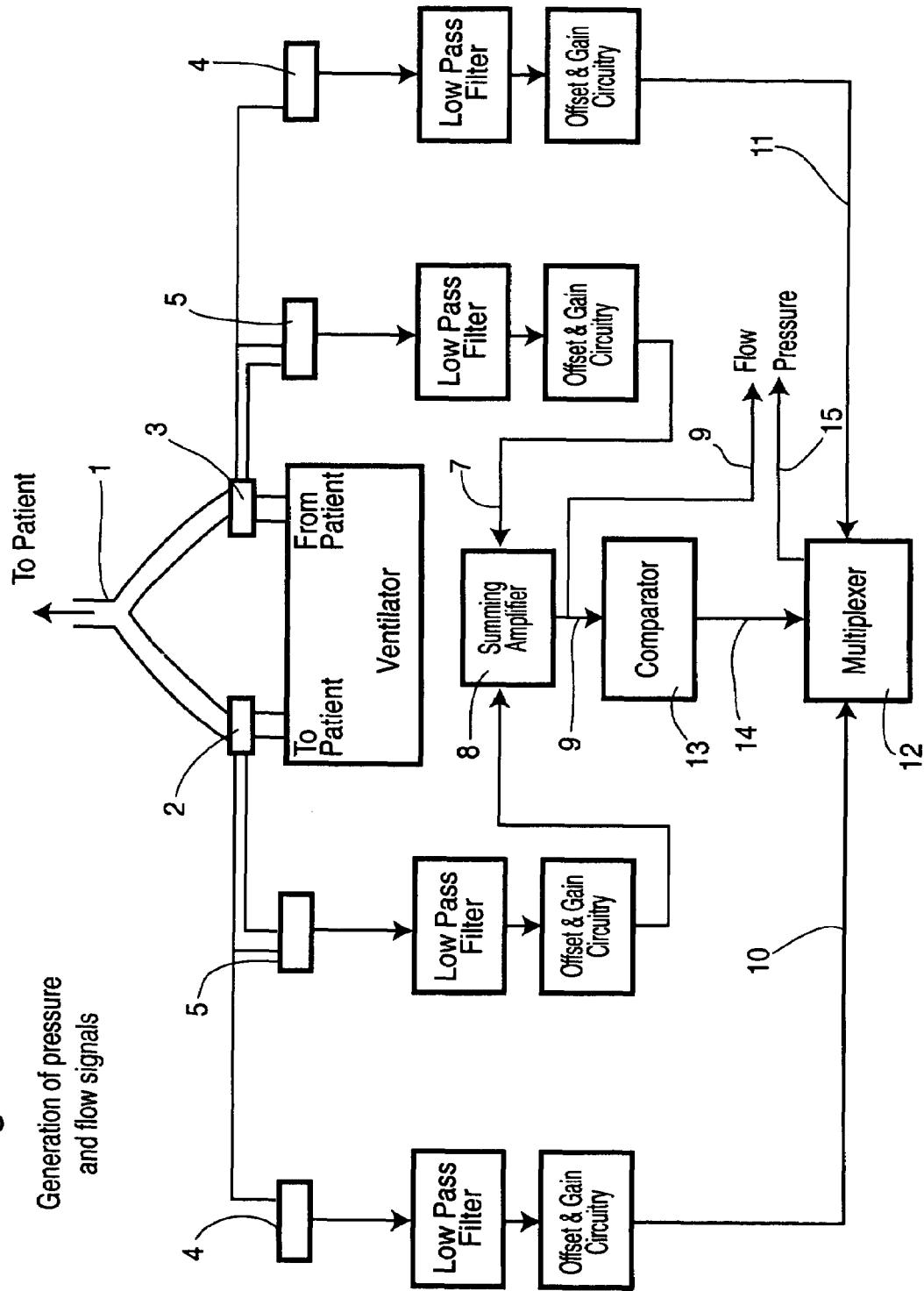
FIG. 7 is a schematic representation of the generation of pressure and flow signals.

The procedures of the present invention as described in details above may be implemented in a device which may be constructed as a freestanding device to be attached externally to a ventilator, or may be incorporated within the ventilator. In either case, the operation of the device requires inputs related to pressure and airflow in the ventilator circuit. FIG. 7 shows a design and components suitable for obtaining these signals. Although it is possible to obtain these signals by attaching a flow meter and pressure port to the common tube connecting ventilator to patient 1, it is preferable to monitor flow and pressure separately in the inspiratory and expiratory lines and to combine the signals. This is to avoid clogging of the flow meter and to minimize the number of tubing connections extending from near the patient's head to the device. Accordingly, as shown in FIG. 7, a flow meter and pressure port are inserted in the inspiratory line 2 and another set is inserted in the expiratory line 3. Each set is connected to appropriate pressure 4 and flow 5 transducers, which generate signals proportional to pressure and flow, respectively. The signals from each pressure 4 and flow 5 transducer is conditioned with suitable low pass filters (e.g. 10 Hz) and offset and gain circuitry. Suitable calibrations for the pressure and flow signals are 10 cmH$_2$O/volt and 1.0 l/sec/volt, respectively. The processed inspiratory 6 and expiratory 7 flow signals are summed using a summing amplifier 8 to produce a composite flow signal 9 to be used by the device. The inspiratory 10 and expiratory 11 pressure signals are connected to a multiplexer 12. A comparator 13 receives the common flow signal 9 and provides a signal 14 to the multiplexer 12 indicating the polarity of the flow signal 9. The multiplexer generates a pressure signal 15 composed of the inspiratory pressure signal 10 when flow is expiratory and the expiratory pressure signal 11 when flow is inspiratory. In this fashion the pressure measured at any instant is a close approximation of pressure in the tubing near the patient 1 since at all times a static air column exists between the active transducer and the common ventilator tubing 1 near the patient.

Pressure and flow signals are routinely generated in modern ventilators using an approach similar to that of FIG. 7. If the device of this invention is incorporated in the ventilator, the pressure and flow signals generated independently by the ventilator can be used instead.

Figure 8A:
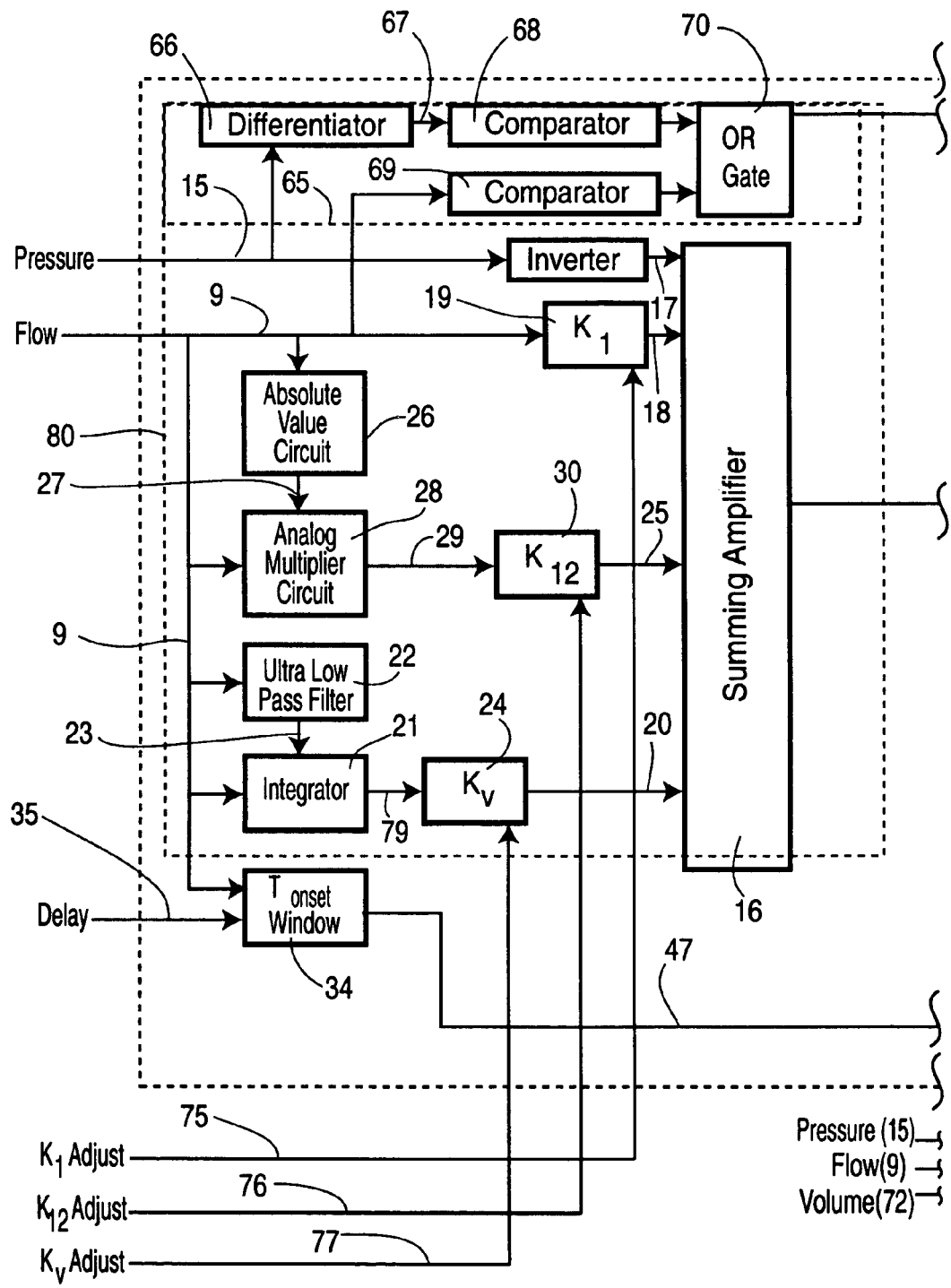
FIG. 8 is a block diagram of one embodiment of a device operating in accordance with the method of the invention.
Figure 8B:
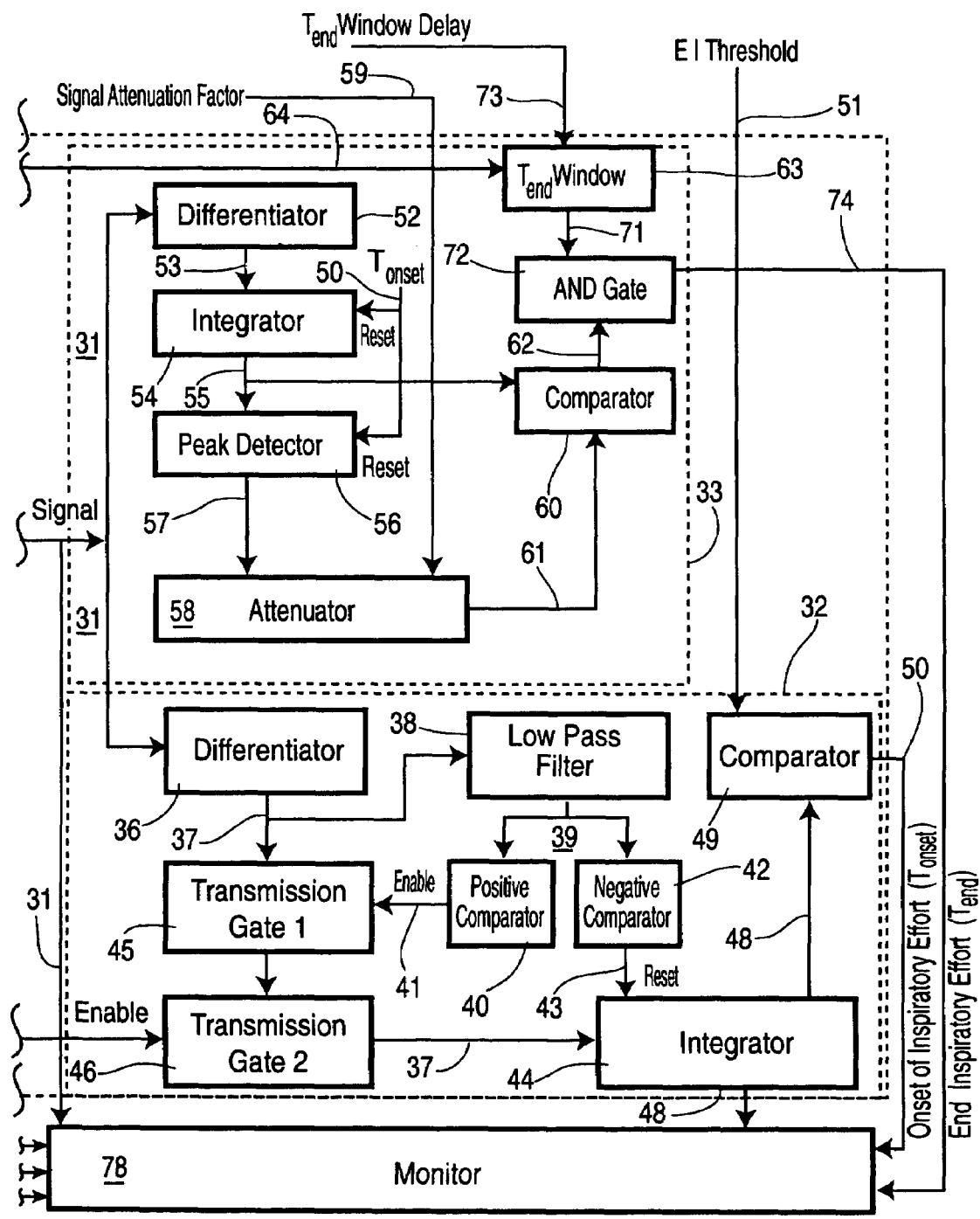

FIG. 8 is a block diagram of an analog embodiment of the invention. A summing amplifier 16 combines four signals, namely a) the pressure signal 15 suitably inverted 17 and b) the flow signal 9 after suitable amplification 18 using a variable gain amplifier 19. This amplifier 19 provides the desired value of $K_f$ (Equations 2, 3 and 4). c) A suitably conditioned and amplified volume signal 20 generated by integrating 21 the flow signal (9) after subtracting a highly filtered (using an ultra low pass filter 22) flow signal 23 to minimize volume drift. A variable gain amplifier 24 provides the desired amplification ($K_v$) of the volume signal (as per Equations 3 and 4). d) A signal 25 comprised of the product [flow*absolute flow] after suitable amplification. This is an optional signal to be included if it is desired to compensate for non-linearities in the pressure-flow relation as per Equation 4. The signal corresponding to [flow*absolute flow] is generated by processing the flow signal 9 through an absolute value circuit 26, and multiplying the output of this circuit 27 by the flow signal 9 using an analog multiplier circuit 28. The resulting signal 29 is then amplified with a variable gain amplifier 30 that provides the desired value of $K_{f2}$ (Equation 4).

The signal 31 generated by the summing amplifier 16 is further processed by two circuits, one for detecting the onset of inspiratory effort ($T_{onset}$ identification circuit 32) and one for detecting the end of inspiratory effort ($T_{end}$ identification circuit 33). The overall purpose of the first circuit 32 is to measure the increase in the amplitude of the signal 31 during periods in which the signal 31 is rising, within a specific time window in the breath determined by a $T_{onset}$ window circuit 34. This time window begins after a specified delay 35 from the point at which expiratory flow decreases below a specified value (e.g. −0.2 l/sec) during expiration. As seen in the diagram of the first circuit 32, the signal 31 is differentiated using a differentiator 36. The differentiated signal 37 is filtered using an appropriate low pass filter (e.g. 5 Hz) 38 to remove high frequency noise. The filtered differentiated signal 39 is passed through two comparators. One comparator 40 sends an enabling positive signal 41 when the filtered differentiated signal 39 is positive and the other comparator 42 sends an enabling positive signal 43 when the filtered differentiated signal 39 is negative. The unfiltered signal 37 is integrated 44 when two gates 45,46 are enabled. The first gate 45 is enabled when the filtered differentiated signal 39 is positive, as detected by the positive comparator 40. The second gate 46 is enabled during the specified time window during expiration, as detected by the $T_{onset}$ window circuit 34 and conveyed to the gate by an enabling signal 47. The integrator 44 is reset whenever the filtered differentiated signal 39 becomes negative as detected by the negative comparator 42. In this fashion integration begins anew only when the signal is rising within the specified time window. The integrator output 48 is received by a comparator 49 which sends out a signal 50, indicating $T_{onset}$, when integrator output exceeds a specified threshold set by an external EI threshold adjust 51.

The specific design used for detection of onset of effort in this implementation 32 is selected because it offered an optimal combination of sensitivity and specificity (i.e. sensitive yet not prone to false triggering). It is clear, however, that other designs for detecting a change in signal trajectory are possible. For example, the filtered differentiated signal 39, representing current rate of change in signal, can be delayed by a specified amount (e.g. 200 msec). A comparator (not shown) compares the current and delayed forms of the filtered differentiated signal. A signal, indicating onset of effort, is generated when the difference exceeds a threshold value. Alternatively, the signal itself 31 may be delayed by a specified amount (e.g. 200 msec). A comparator (not shown) compares the current and delayed forms of the actual signal and generates a signal, indicating onset of effort, when the difference exceeds a threshold value. Other approaches are possible within the scope of this invention.

For identifying the $T_{end}$ 33, the signal 31 is first differentiated 52 and the differentiated signal 53 is reintegrated 54. The integrator is reset at the onset of inspiratory effort ($T_{onset}$) using the signal 50 generated from the $T_{onset}$ identification circuit 32. In this fashion, any baseline offset in the signal 31 is eliminated and the output of the integrator 55 reflects only the increase in signal 31 amplitude from $T_{onset}$. Integrator output 55 is connected to a peak detector circuit 56, which is also reset by the $T_{onset}$ signal 50. The output of the peak detector 57 is attenuated 58 with a suitable attenuation factor (e.g. 50%). Optionally, the attenuation factor may be individually adjusted by the user through an external input 59. A comparator 60 sends a signal 62 when current integrator output 55 decreases below the attenuated peak detector output 61. In this fashion the end of inspiratory effort is detected when the current integrator output 55 decreases below a set percent of the peak level reached during the current inspiratory effort.

At times, the signal 31 or 55 transiently decreases at the time of ventilator triggering (Ventilator Trigger Artifact, FIG. 5). Unless corrected, or allowed for, this artefact may result in false detection of $T_{end}$. A circuit is incorporated to reduce or eliminate the occurrence of false identification of $T_{end}$. The circuit consists of a delay circuit 63 similar to the one used in the $T_{onset}$ identification circuit 34. A timer is activated by a $T_{trigger}$ signal 64 received from a $T_{trigger}$ identification circuit 65. The latter circuit receives inputs from the pressure 15 and flow 9 signals. The pressure signal is differentiated 66 and the resulting signal 67 is directed to a comparator 68 with a suitable reference value (e.g. 15 cmH$_2$O/sec). The flow signal 9 also is connected to a comparator 69 with a suitable reference value (e.g. 0.3 l/sec). The outputs of the two comparators 68, 69 are received by an OR gate 70 which sends a $T_{trigger}$ signal 64 to the delay circuit 63 when either the differentiated pressure signal 67 or the flow signal 9 exceed the set value in the respective comparator 68 or 69. The delay circuit 63 in turns sends a signal 71 to an AND gate 72 after a specified delay set either externally via a user input 73 or internally as a default value (e.g. 0.2 sec). The AND gate 71 also receives the $T_{end}$ signal 62 and sends a final $T_{end}$ signal 74 only if it occurs after the specified delay from $T_{trigger}$. In this fashion, $T_{end}$ signals generated by the triggering artifacts are screened out.

User Inputs:

The number and types of user inputs may vary depending on how comprehensive the device is and the extent to which user involvement is desired by the manufacturer. In the most comprehensive analog embodiment shown in FIG. 8, there are seven user inputs:

1) $K_f$ adjust 75: This input determines the gain of the $K_f$ variable gain amplifier 19. A suitable range is 1 to 25 cmH$_2$O/l/sec. Because the calibration factors of the flow and pressure signals may be different (for optimal signal to noise ratio, see above) an attenuation factor is incorporated to make allowance for the different calibration factors. For example, if the flow calibration factor is 1.0 l/sec/volt and the pressure calibration factor is 10.0 cmH$_2$O/volt, the relation between the $K_f$ adjust input 75 and the gain of the $K_f$ variable gain amplifier 19 should be 10. In this fashion, the output of the $K_f$ variable gain amplifier, which has units of pressure, is comparable to the pressure signal 17 at 10.0 cmH$_2$O/volt.

2) $K_{f2}$ adjust 76: This input determines the gain of the $K_{f2}$ variable gain amplifier 30. A suitable range is 1 to 25 cmH$_2$O/l$^2$/sec$^2$ to take account of the various sizes of endotracheal tubes used in practice. Again, a suitable attenuation factor between the $K_{f2}$ input 76 and the actual $K_{f2}$ gain 30 needs to be incorporated to allow for differences in pressure and flow calibration factors (see #1 immediately above).

3) $K_v$ adjust 77: This input determines the gain of the $K_v$ variable gain amplifier 24. A suitable range is 5 to 100 cmH$_2$O/l. A suitable attenuation factor between the $K_v$ input 77 and the actual $K_v$ gain 24 needs to be incorporated to allow for differences in pressure and flow calibration factors (see #1 immediately above).

4) $T_{onset}$ window delay 35: This input determines the desired delay, from the point at which expiratory flow decreases below a set value, before the device begins looking for $T_{onset}$. A suitable range is 0 to 3.0 seconds.

5) E I threshold 51: This determines the amount of increase in signal amplitude, as detected by the integrator 44 of the $T_{onset}$ circuit 32, above which $T_{onset}$ is identified. A suitable range is 0.1 to 10.0 cmH$_2$O.

6) Signal attenuation factor 59: This determines how much signal amplitude must decrease, after $T_{onset}$, before the $T_{end}$ is identified. A suitable range is 20 to 90%.

7) $T_{end}$ Window delay 73: This input determines the period, from $T_{trigger}$, during which $T_{end}$ signals 62 are screened out. A suitable range is 0.0 to 0.3 second.

Some inputs may be deleted by using fixed default values within the device. For example, the $K_f$ adjust input 75 may be deleted and a fixed value of 10.0 is used. A fixed $T_{onset}$ delay value of, for example, 0.3 second may be used, eliminating the $T_{onset}$ window delay input 35. A suitable default signal attenuation value (e.g. 50%) may be used replacing the corresponding input 59. Likewise, a $T_{end}$ window delay of 0.2 second may be used eliminating the $T_{end}$ window delay 73. Clearly, the more fixed the settings are the less reliable the performance of the device may become. However, this may be acceptable under some circumstances with the potential benefit of simplifying the operation of the device. An alternative would be to have the device operate with default settings unless changed by the user.

Other inputs may also become unnecessary if simpler forms of the signal 31 are generated. For example, signal component related to the non-linear flow function 25 may be eliminated according to Equation 3. In this case the $K_{f2}$ adjust input 76 is deleted. Likewise, the signal component related to volume 20 may be eliminated, according to Equation 2, with corresponding deletion of the $K_v$ adjust input 77. Again, the simpler the device, the less reliable its performance will become but this may be acceptable under certain circumstances. In its simplest form, all the user needs to do is to set the E I threshold input 51.

Device Outputs:

Certain internal signals need to be displayed to allow the user to adjust the input settings, while others provide the user with the results of monitoring. These signals can be displayed on a monitor 78 included in a freestanding device. Alternatively, if the device is incorporated inside the ventilator, the monitor of the ventilator can be used for this purpose. A third embodiment involves directing the device's outputs to an analog to digital converter and displaying the outputs on a separate computer.

The following output signals are necessary for adjusting the input settings:

a) The main signal itself 31.
b) The output of the integrator 48 in the $T_{onset}$ circuit (32).

The use of these two signals for the sake of input adjustment is described below under OPERATION (below).

Additionally, the signals representing flow 9, pressure 15 and volume 79 may be displayed on the monitor for general monitoring purposes.

Signals representing the onset of inspiratory effort 50 ($T_{onset}$) and end of inspiratory effort 74 ($T_{end}$) are also displayed on the monitor. In the event these signals are to be used to actively control the cycling of the ventilator, they are communicated to the ventilator's cycling mechanism.

Additional information of value in guiding ventilator setting is most conveniently generated by a small microprocessor. A block diagram of a preferred embodiment (103) is provided in FIG. 9. Here, the flow signal 9 is digitized using an analog to digital converter. In addition, the central processing unit receives the signals corresponding to $T_{onset}$ 50 and $T_{end}$ 74 of inspiratory effort and signals reflecting ventilator trigger time ($T_{trigger}$) 64 and cycling off time ($T_{off}$, derived from the $T_{onset}$ Window circuit 34 see also 96 in FIG. 12). The latter two signals may also be obtained directly from the ventilator. The user inputs the ventilator mode 88 and the desired $T_I/T_{TOT}$ ratio 89. From these data, the microprocessor calculates trigger delay ($T_{trigger}-T_{onset}$) 80 and cycling off delay ($T_{off}-T_{end}$) 81. The flow signal is differentiated. Additional inspiratory efforts during the inflation phase 82 are identified when the differentiated flow becomes positive after an earlier negative phase (Identify additional efforts function 82, FIG. 9). A "calculate patient rate function" (83, FIG. 9) calculates respiratory rate of patient 83 from the sum of number of $T_{onset}$ transitions during expiration 50 in the last minute and the number of additional efforts during inflation 82 in the last minute. The number of ventilator cycles per minute 84 is calculated from the number of $T_{trigger}$ signals 64 in the last minute. The number of ineffective efforts 85 is calculated from the difference between patient respiratory rate 83 and ventilator rate 84. This additional information is then displayed on the monitor. Additionally, with knowledge of patient respiratory rate 83 the average breathing cycle duration ($T_{tot}$, $T_{tot}$=60/respiratory rate) of the patient can be calculated. The microprocessor calculates the desirable duration of ventilator cycle 87 (desirable $T_I=T_{TOT}$*desirable $T_I/T_{TOT}$) where $T_I/T_{TOT}$ is a default value (e.g. 0.4) or a user input 89. The microprocessor also receives a user input indicating the mode of ventilation 88. In the PSV mode, the microprocessor samples flow at the desired $T_I$ in several elapsed cycles (Flow at desired $T_I$ function 90), and displays the average value on the monitor. The user can take advantage of this information (desired $T_I$ or Flow at desired $T_I$) to adjust ventilator settings to result in optimal $T_I/T_{TOT}$.

In another embodiment of the output processor 103 patient respiratory rate (or $T_{TOT}$) is inputted to the processor, replacing the "Calculate Patient Rate" function 83. This input is then used to calculate the "Desirable $T_I$" 87 and "Flow at Desired $T_I$" 90. Patient respiratory rate may be determined by the user from inspection of chest movements or by observing the flow tracing on the monitor, or automatically using computational methods other than the ones described in the above embodiment 103.

Operation

Figure 10:
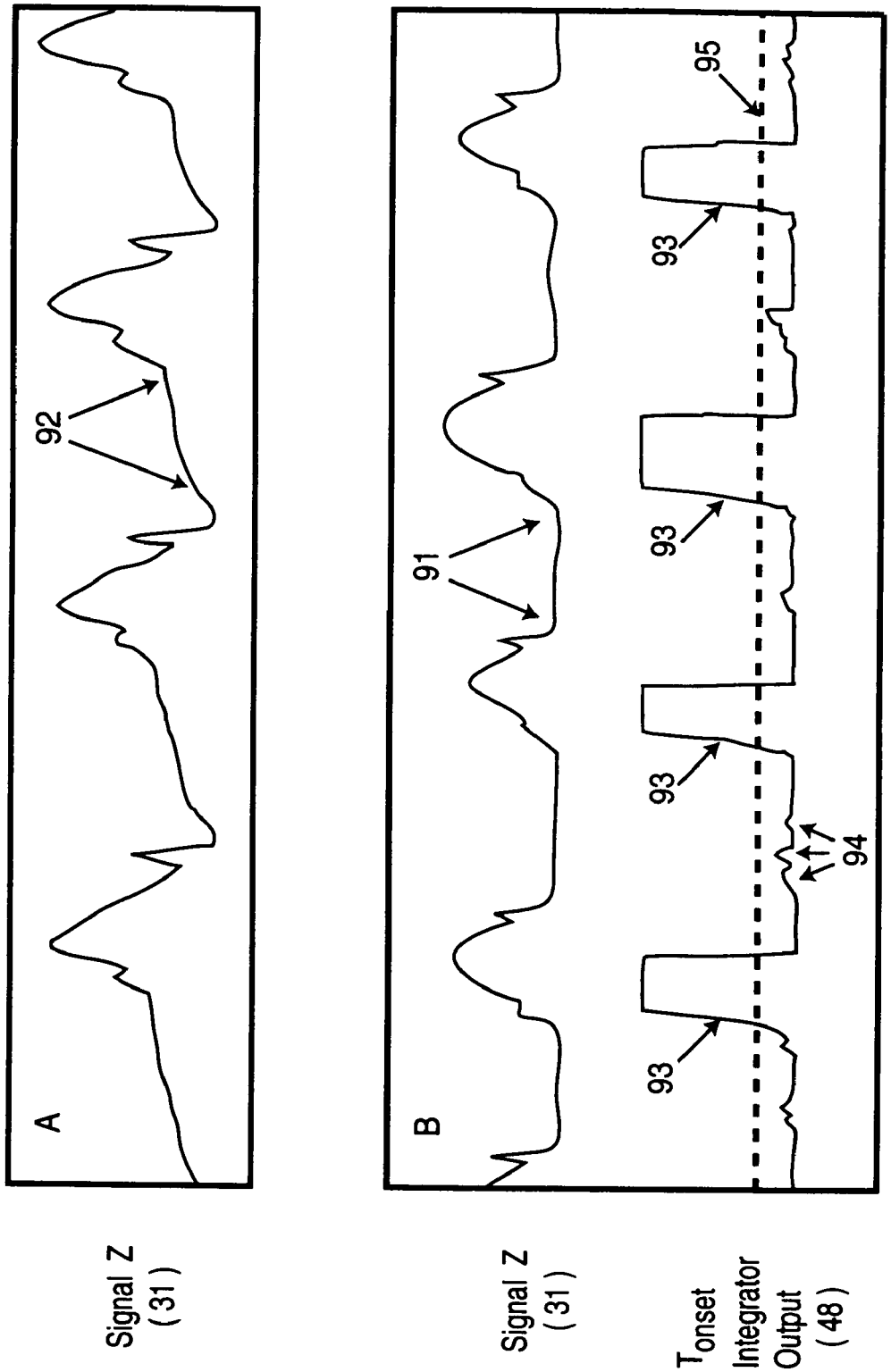
FIG. 10 contains traces of composite pressure signal Z and $T_{onset}$ integrator output.

When the device is built inside the ventilator, the pressure 15 and flow 9 signals are permanently connected to the device. For freestanding systems, the first step is to connect the flow meters and pressure ports to the inspiratory 2 and expiratory 3 lines close to the ventilator (FIG. 7). The device is turned on. Tracing of the Signal 31 appears on the screen (FIG. 10). Subsequent steps depend on what inputs are available on the device and user preference. For the most comprehensive analog embodiment (FIG. 8) the recommended procedure is as follows:

1) Enter the $K_{f2}$ value 76. This is the $K_2$ value of the endotracheal tube in use. A table is provided that states the $K_2$ values for the range of endotracheal tube sizes used.
2) Set the other inputs to default values as follows: $K_f$ 75=10; $K_v$ 77=25; $T_{onset}$ window delay =10% of respiratory cycle duration. For example if respiratory rate is 20/min, set the delay to 0.3 sec; Signal attenuation factor 59=50%; $T_{end}$ Window Delay 73=0.2 second.
3) If the baseline of the signal 31 is flat in the latter half of expiration (e.g. 91, FIG. 10B) no further adjustment of $K_v$ is necessary. If it is not flat (e.g. 92, FIG. 10A), adjust $K_v$ setting 77 to make it flat or slightly sloping down (e.g. 91, FIG. 10B).
4) If it is difficult to have reasonably linear signal trajectory using the $K_v$ adjust input 77 alone, adjust the $K_{f2}$ adjust input 76 up or down as necessary to minimize non-linearities.
5) The tracing representing integrator output 48 (FIG. 10B) shows relatively large broad waves, representing inspiratory efforts 93, FIG. 10B), and smaller, briefer spikes representing noise (94, FIG. 10B). Set the E I threshold level (51) to be just above the smaller spikes in several consecutive breaths (e.g. 95, FIG. 10B).
6) Display the $T_{onset}$ 50 and $T_{end}$ 74 on the screen. If there are frequent $T_{onset}$ signals triggered by noise, increase the level of the E I threshold. If there are frequent $T_{onset}$ signals triggered early in expiration, increase the $T_{onset}$ Window delay 35. If the $T_{end}$ signal occurs too early or too late during the declining phase of the signal 31, adjust the signal attenuation factor 59 accordingly. If there are frequent false triggers of $T_{end}$ at the time of ventilator triggering, increase the $T_{end}$ Window Delay 73 to eliminate false triggering of $T_{end}$.

Figure 11A:
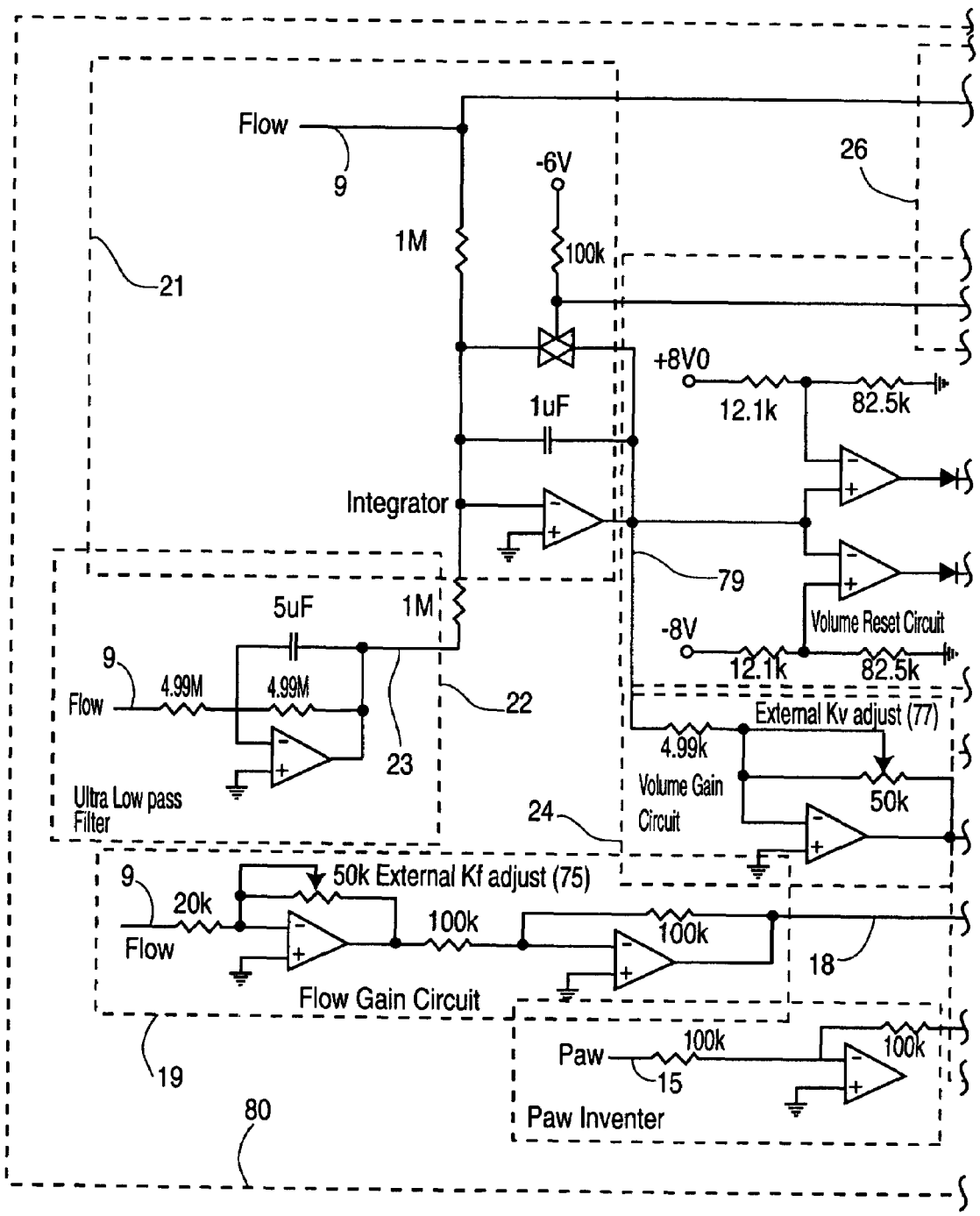
FIGS. 11 and 12 show the electrical circuitry used in apparatus of FIG. 8.
Figure 11B:
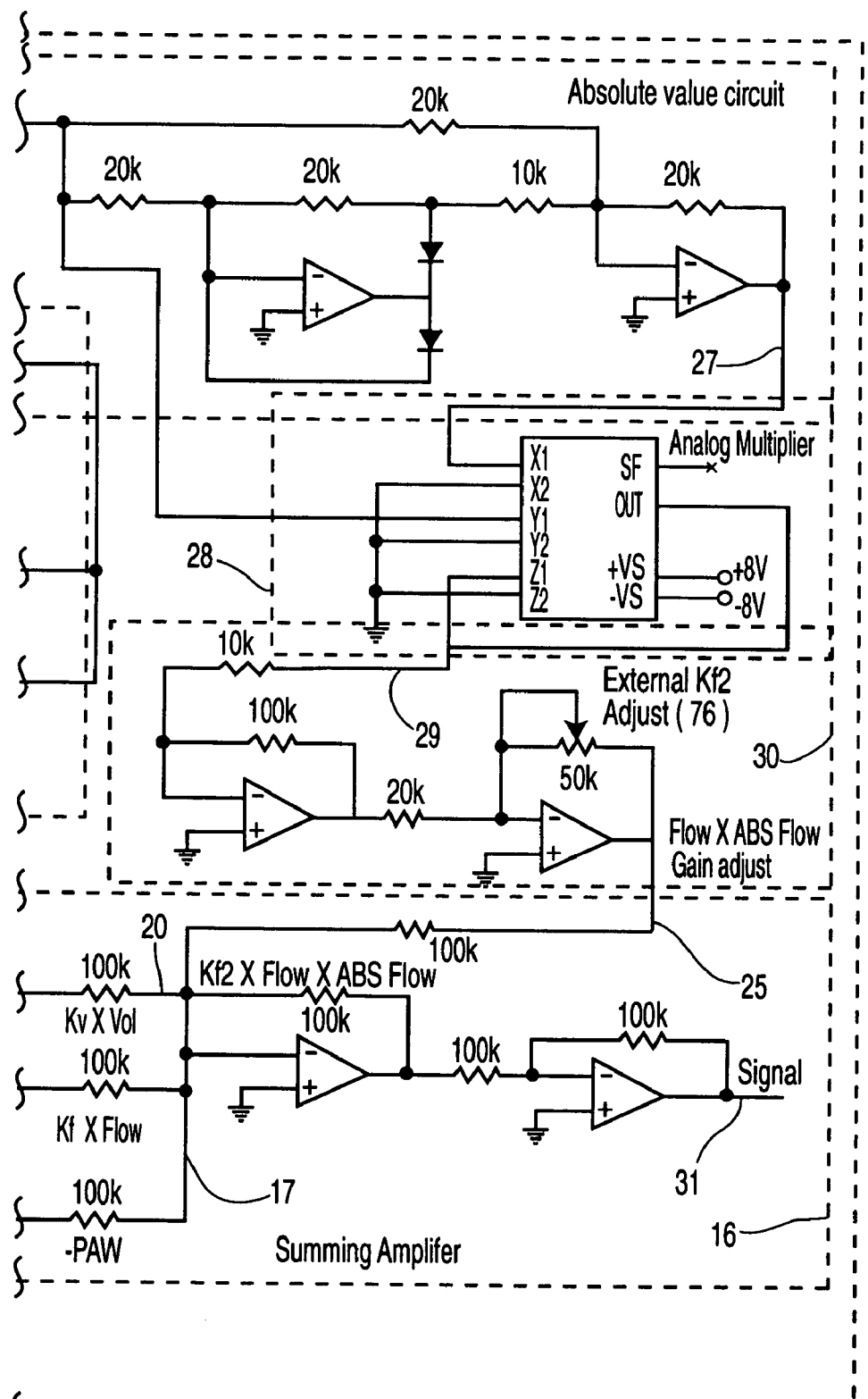
Figure 12:
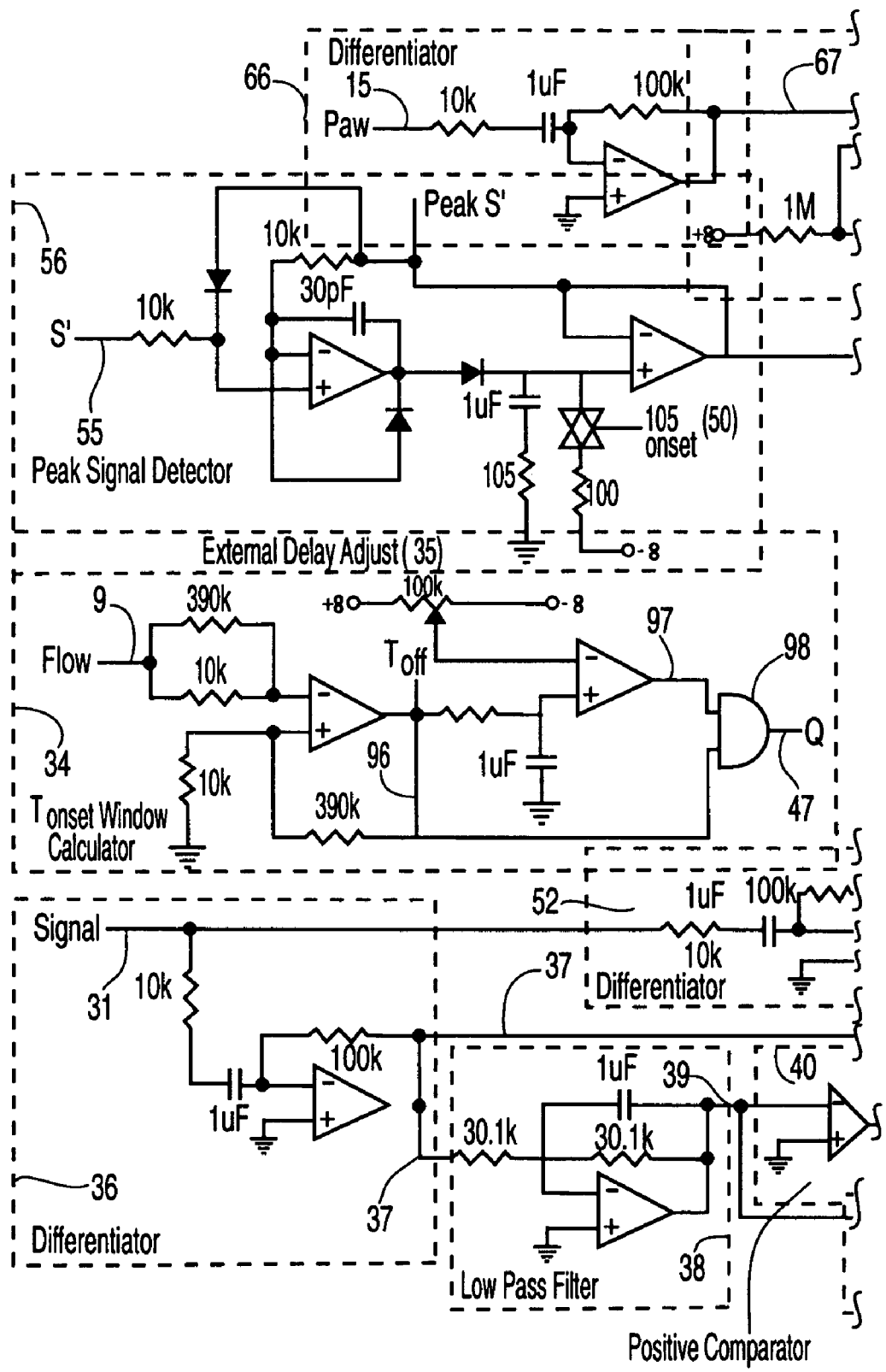
Figure 12:
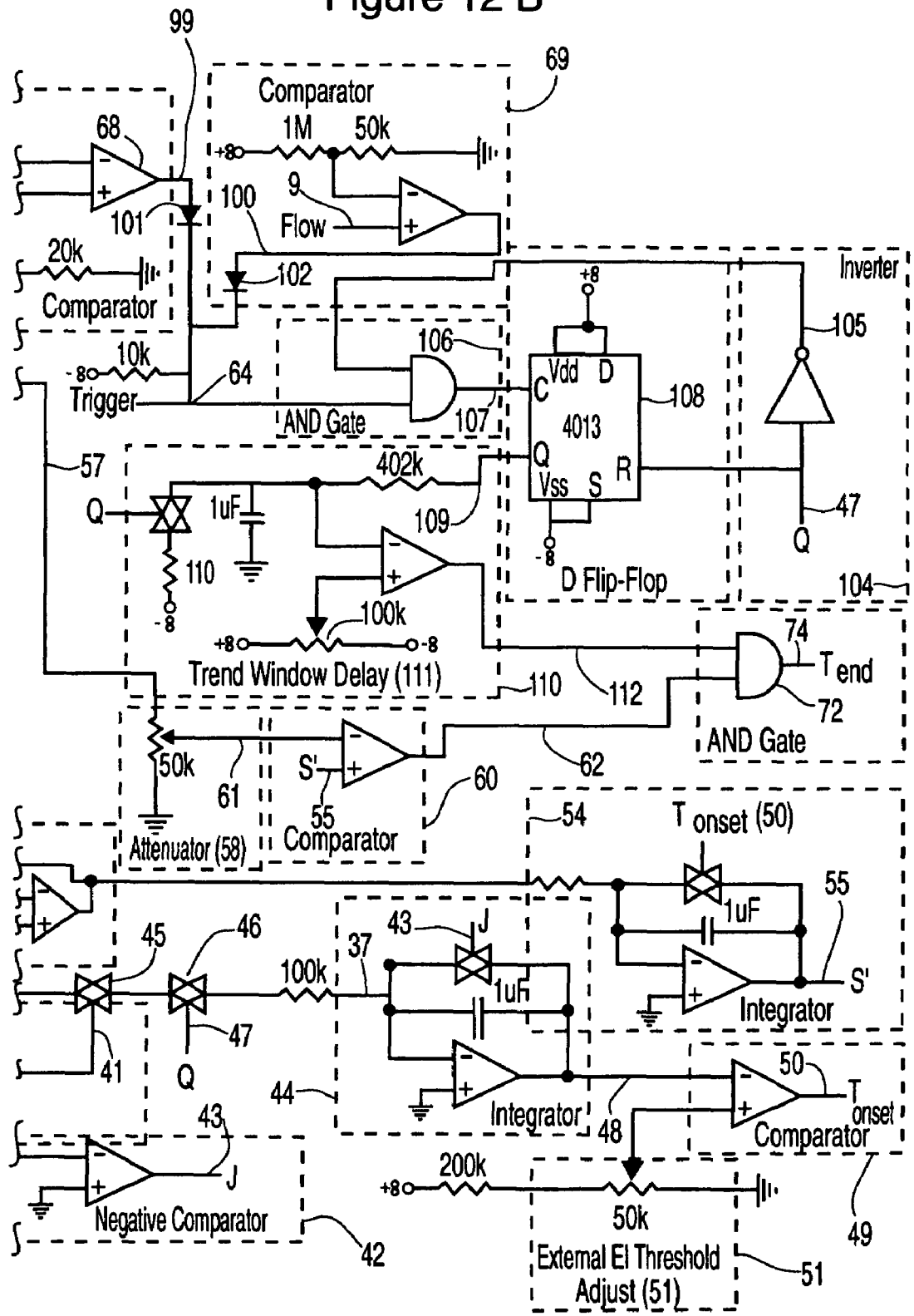
Figure 13:
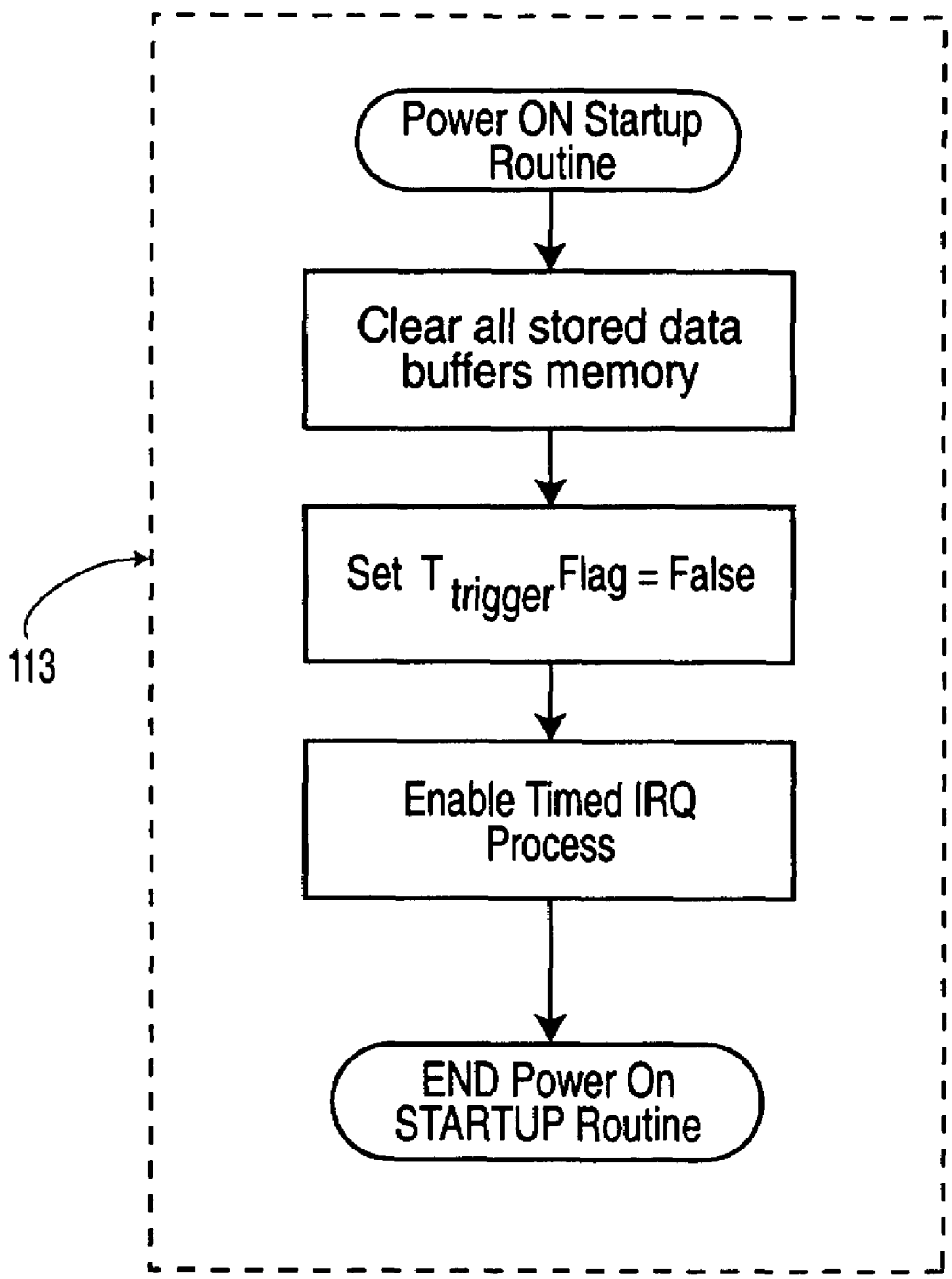
FIGS. 13 to 17 contain flow charts for the different functions performed by the output microprocessor shown in FIG. 9.
Figure 14:
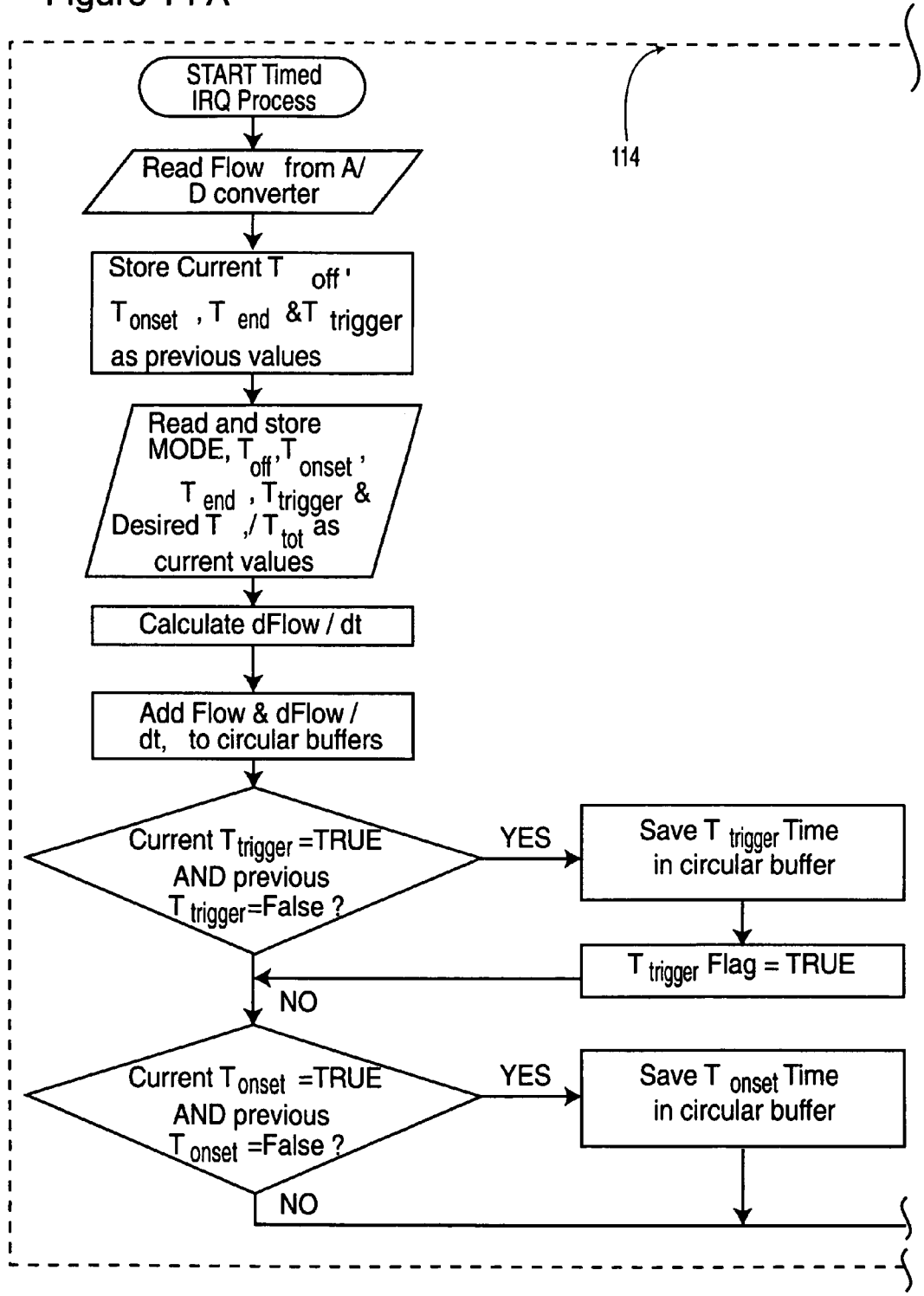
Figure 14:
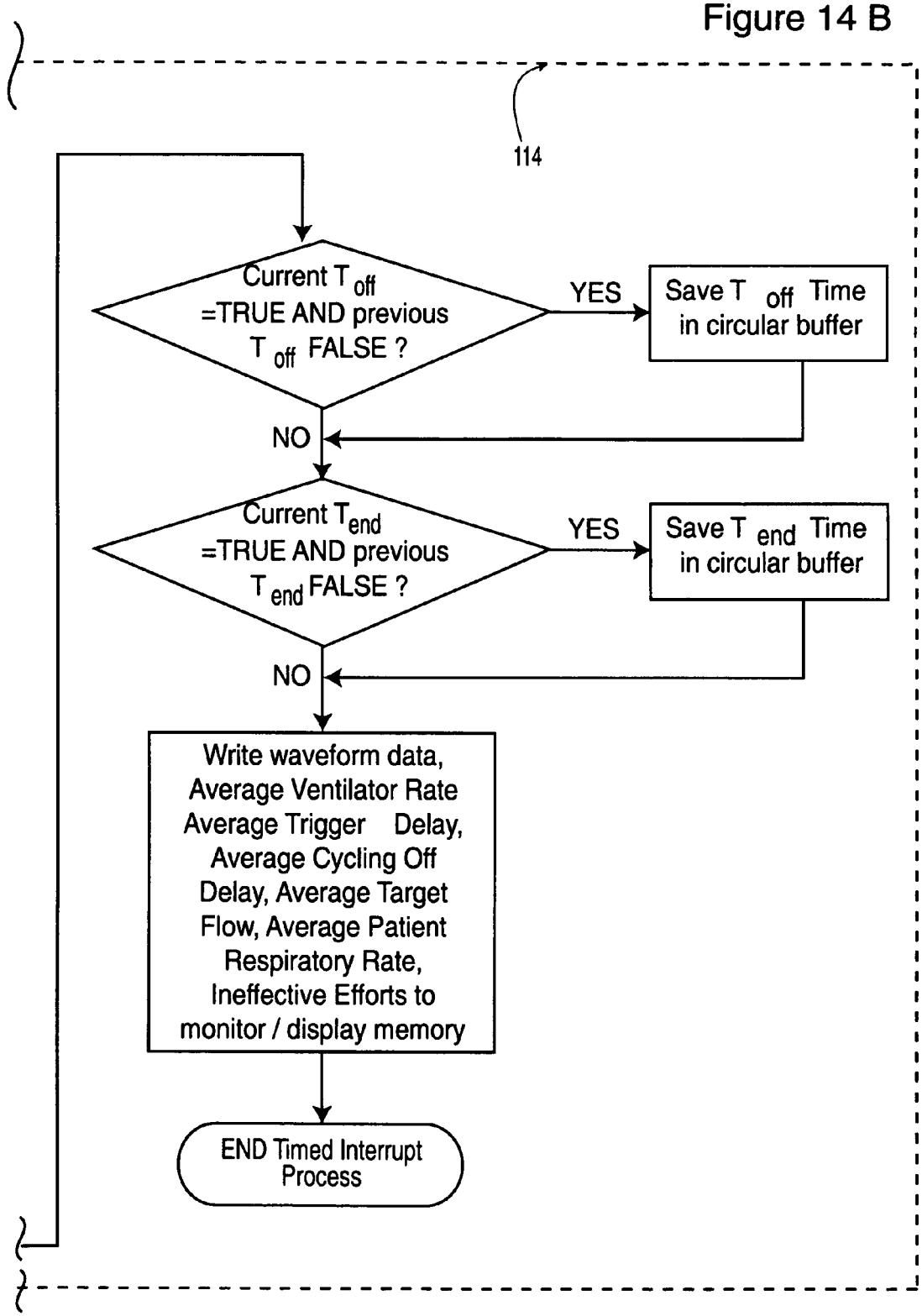
Figure 15:
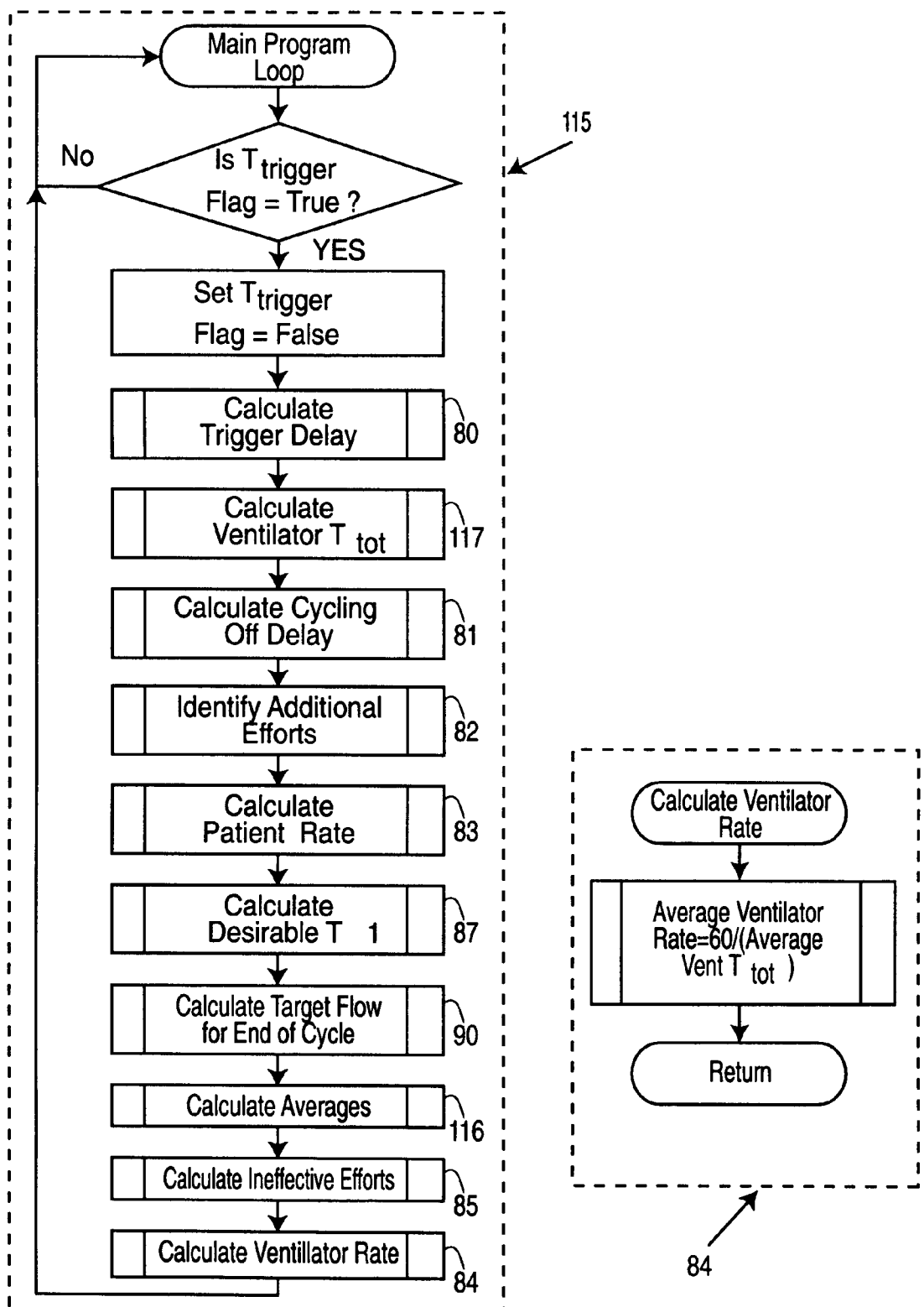
Figure 15:
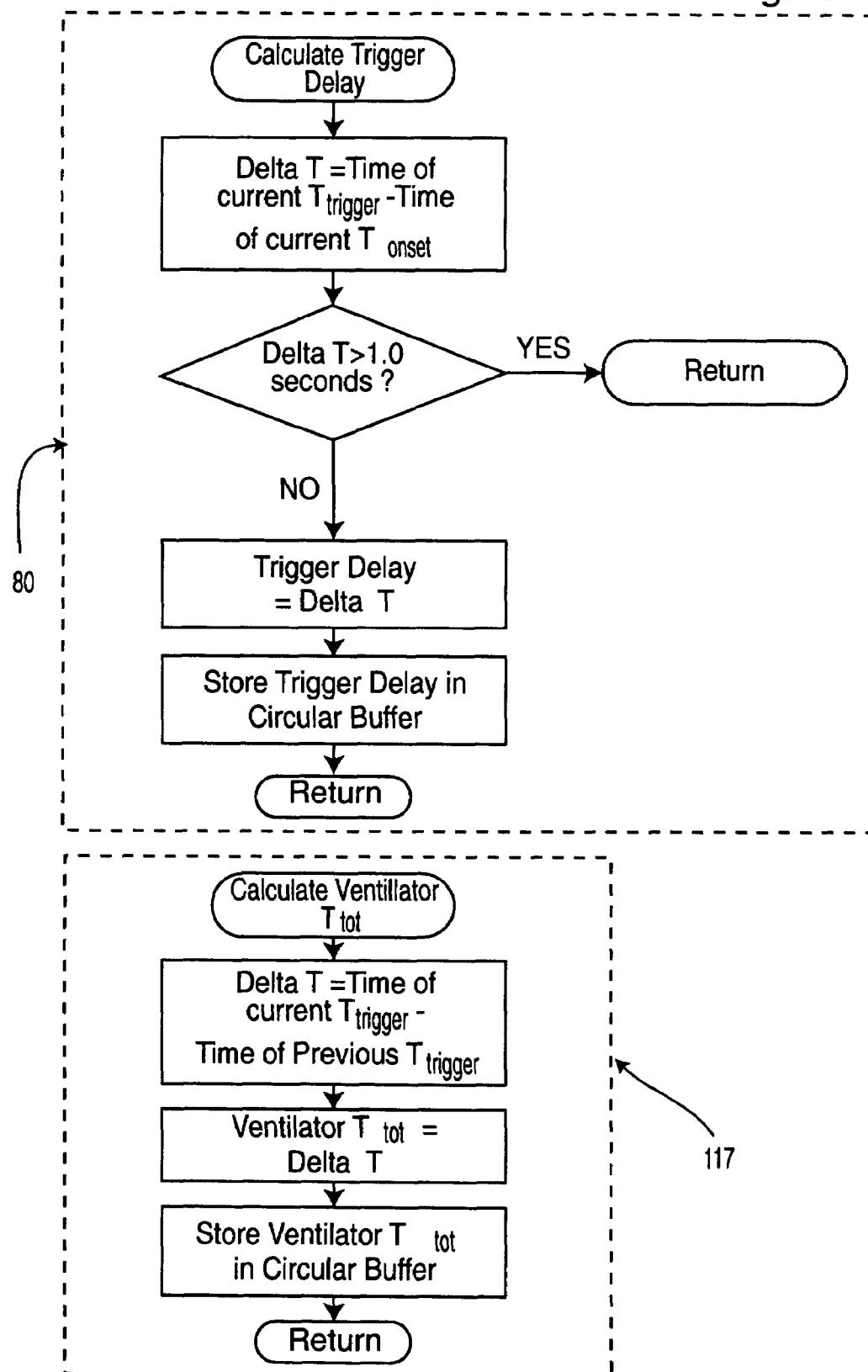

FIGS. 11 and 12 show details of the electrical circuitry used in the preferred embodiment (FIG. 8). All circuits are powered by a suitable +/−8 volts power supply. In FIG. 11 the circuitry used to generate the main signal 31 (block 80 in FIG. 8) is displayed. The summing amplifier 16 with its 4 inputs (17,18,20,25) is shown in the lower right corner of the Figure. Circuitry used to process the four inputs prior to the summing amplifier stage is outlined in boxes bearing the same numbers as in the corresponding components of the block diagram (FIG. 8). The individual electrical components in each circuit are identified by standard electrical symbols and the values of resistors and capacitors indicated are those used in a properly functioning prototype.

FIG. 12 shows details of he electrical circuitry used for $T_{onset}$ identification 32 and $T_{end}$ identification 33. As in FIG. 11, the individual electrical components in each circuit are identified by standard electrical symbols and the values of resistors and capacitors indicated are those used in a properly functioning prototype. The specific function of each circuit and its connections to other circuits have been described in detail in relation to the block diagram of FIG. 8, and the design of each circuit is standard for the purpose intended in each case. Some of the component circuits need additional explanation, however:

$T_{onset}$ Window circuit 34: In this circuit the flow signal is connected to a Schmitt trigger circuit (left half of the $T_{onset}$ window circuit 34) characterized by hysteresis. With the indicated values of the different circuit components, the Schmitt circuit sends out a constant voltage (8 volts) whenever flow decreases below −0.2 l/sec 96. The signal 96 remains on until flow rises to >0.2 l/sec. In this application, the onset of the signal 96 indicates the beginning of the exhalation phase and is also used to mark the end of ventilator cycle ($T_{off}$). The output of the Schmitt trigger circuit is connected to a delay circuit with an externally adjustable delay time 35. The output of the delay circuit 97 is received by an AND gate 98. The AND gate 98 also receives the output of the Schmitt trigger circuit 96 directly and sends a signal when the $T_{onset}$ window is open, as indicated by the output of the Schmitt trigger circuit 96 but only after the specified delay 35 has elapsed, as indicated by a positive output from the delay circuit 97. In turn, the output of the AND gate 47 (referred to as Q signal in FIG. 12) serves multiple functions that include enabling one of the transmission gates 46 in the $T_{onset}$ identification circuit 32.

$T_{trigger}$ 64 detection circuitry: There are many ways by which the time at which the ventilator was triggered can be detected. In this embodiment $T_{trigger}$ was detected when the rate of increase in pressure exceeded 15 cmH$_2$O/second OR flow increased beyond 0.4 l/second. To this end, a differentiator 66 was used to obtain Δpressure/Δt 67. Next, a comparator 68 produces a positive signal 99 when Δpressure/Δt 67 exceeds a set value of 15 cmH$_2$O/second. In another circuit 69 a comparator generates a positive signal 100 when flow (9) exceeds 0.4 l/second. Two diodes 101,102 function as an OR gate so that a positive signal ($T_{trigger}$, 64) is generated when either the Δpressure/Δt or flow exceed the set respective thresholds.

$T_{end}$ Window circuit 63: This circuit has four components. First, the Q signal 47, representing time window for $T_{onset}$ detection, is inverted using an inverter 104. The positive phase of this inverted Q signal 105 defines the maximum period during which $T_{end}$ can be located. The second component is an AND gate 106 which receives the inverted Q signal 105 and the $T_{trigger}$ signal 64 and sends a positive signal 107 when both its inputs are positive. The positive edge of this signal 107 activates a flip-flop switch 108, which is the third component of the $T_{end}$ Window circuit. The flip-flop switch 108 is reset by the Q signal 47. The fourth component is a delay circuit 110 with an adjustable external control 111. The delay circuit 110 receives the output of the flip-flop switch 109. After the set delay, the delay circuit 110 sends out a positive signal 112, which persists until the beginning of the Q signal 47. The output of the delay circuit 112 is one of the two inputs to the main AND gate 72 which generates the $T_{end}$ signal 74.

The other components of the $T_{end}$ circuit 33, as shown in FIG. 12, include the differentiator 52 and integrator 54 that calculate the change in the main signal 31 since the onset of the current effort (55, referred to as S' in FIG. 12). The integrator is reset by the $T_{onset}$ signal 50. The peak detector that determines the highest level of signal S' 55 reached during the current effort, is shown 56 and is also reset by the $T_{onset}$ signal 50. The output of the peak detector 57 is attenuated with an externally adjustable attenuator 58. Finally, a comparator 60 receives the output of the attenuated peak signal 61 and the differentiated integrated signal (55, S') and sends a $T_{end}$ signal 62 when the latter 55 decreases below the former 61. The $T_{end}$ signal 62 is gated out only if the $T_{end}$ Window is open as indicated by a positive output of the $T_{end}$ Window delay circuit 112. This gating function is performed by an AND gate 72.

The circuitry used in this preferred embodiment is clearly not the only way by which the functions and results contemplated by the current invention can be implemented. Other circuit designs can be used to accomplish the same objectives and these are within the scope of this invention.

Figure 9:
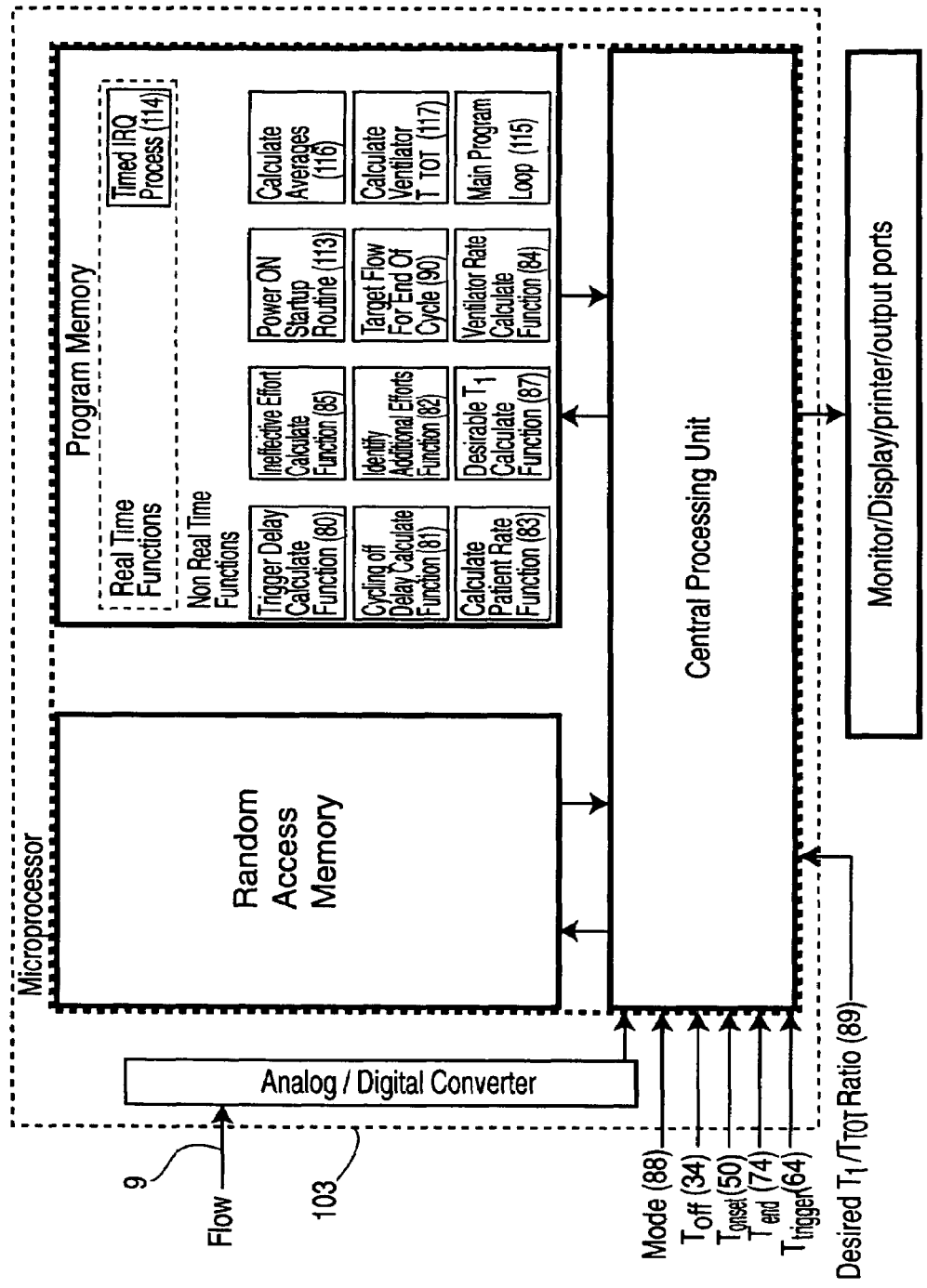
FIG. 9 is a schematic representation of the digital implementation of output functions.

FIGS. 13 to 17 show flowcharts for the different functions performed by the output microprocessor (FIG. 9). The power on start-up routine (113, FIG. 13) clears the memory and enables the Interrupt Request (IRQ) Process. The IRQ process (114, FIG. 14) is executed at suitable intervals (e.g. every 5 msec). It collects data from various inputs (see FIG. 9 for inputs), calculates the time derivative of flow and stores collected and derived data in memory. It also checks for the times at which $T_{trigger}$, $T_{onset}$, $T_{off}$, and $T_{end}$ occur and stores these times in memory. Because all these timing inputs are square functions, detection of the times at which these events occurred is based on a simple comparison of current value with the immediately preceding one. If current value is high and preceding value is low, the event is deemed to have occurred. For example, if current value of $T_{trigger}$ input is high while the immediately preceding value was low, $T_{trigger}$ is deemed to have occurred then, and so on. Finally, the IRQ process writes the waveform data and calculated variables to the monitor. The main program loop (115, FIG. 15) performs the various functions identified in the block diagram (FIG. 9) in sequence each time a $T_{trigger}$ is detected. The flow charts of individual functions are shown in individual diagrams bearing the same numbers. In the trigger delay function (80, FIG. 15), when the difference between current $T_{trigger}$ and the last $T_{onset}$ is >1.0 second, trigger delay is ignored. Thus, the maximum trigger delay allowed is 1.0 second. Situations in which $T_{onset}$ occurs more than 1.0 second before $T_{trigger}$ are usually ventilator cycles triggered by the ventilator and not by the patient. The Calculate Ventilator $T_{TOT}$ function (117, FIG. 15) calculates the interval between current and previous $T_{trigger}$. The cycling off delay function (81, FIG. 16) calculates the difference between the end of ventilator cycle ($T_{off}$) and end of patient effort (($T_{end}$) in current cycle. In the Identify Additional Efforts function (82, FIG. 17) the program looks in the interval between $T_{trigger}$ and $T_{off}$ of the previous cycle for points at which Δflow/Δt crosses from negative to positive and stays positive for 300 msec. When this occurs, it identifies an additional effort during the previous ventilator cycle and adds its time to the circular buffer for subsequent counting. The choice of 300 msec is quite conservative and may suitably be reduced to 200 msec or even less. In the Calculate Patient Rate function (83, FIG. 17) the program calculates the number of $T_{onset}$ transitions and number of Additional Efforts during inflation in the one-minute interval before the current $T_{trigger}$. In this chart PTE refers to efforts occurring during the exhalation phase of the ventilator (i.e. $T_{onset}$ transitions) and PTAE refers to Additional Efforts occurring during the inflation phase of the ventilator. In the Desirable $T_I$ calculate function (87, FIG. 16) the average patient cycle duration ($T_{TOT}$) is calculated from 60/patient respiratory rate calculated in the preceding function (83). Desirable $T_I$ is then calculated from average patient $T_{TOT}$ and the desirable $T_I/T_{TOT}$ as indicated by the desired $T_I/T_{TOT}$ input (89, FIG. 9). In the Calculate Target Flow function (90, FIG. 16) the first decision is whether the mode is pressure support ventilation (PSV). If so, the program reads flow at an appropriate time in the immediately preceding ventilator cycle. There are a number of options for the appropriate time at which to measure flow (see next paragraph). Occasionally, the time at which to measure flow may occur after the end of the ventilator cycle, where flow is negative (i.e. expiratory). This is the case when the respiratory time constant of the patient (resistance/elastance) is too short. A provision is made whereby if flow at the chosen time is negative it is assigned a value of zero. With certain variables it is preferable to provide the user with average results as opposed to, or in addition to, results of individual cycles, which may be quite variable. For this reason individual results of certain variables are stored in circular buffer (e.g. Trigger delay (80, FIG. 15), Cycling off delay (81, FIG. 16), Ventilator $T_{TOT}$ (117, FIG. 15) and Target flow for end of cycle (90, FIG. 16)). The Calculate Averages function (116, FIG. 16) then calculates the average values in a preset number of elapsed breaths. In the illustrated embodiment (116, FIG. 16), the number of cycles averaged is 10. However, other numbers may be chosen depending on manufacturer or user preference. Two other variables are derived from these averaged values. Ventilator rate (84, FIG. 15) is calculated from [60/average ventilator $T_{TOT}$ (117)) and the number of Ineffective Efforts (85, FIG. 16) is calculated from the difference between Average Patient Rate (83, FIG. 17) and Average Ventilator Rate (84, FIG. 15).

Figure 16:
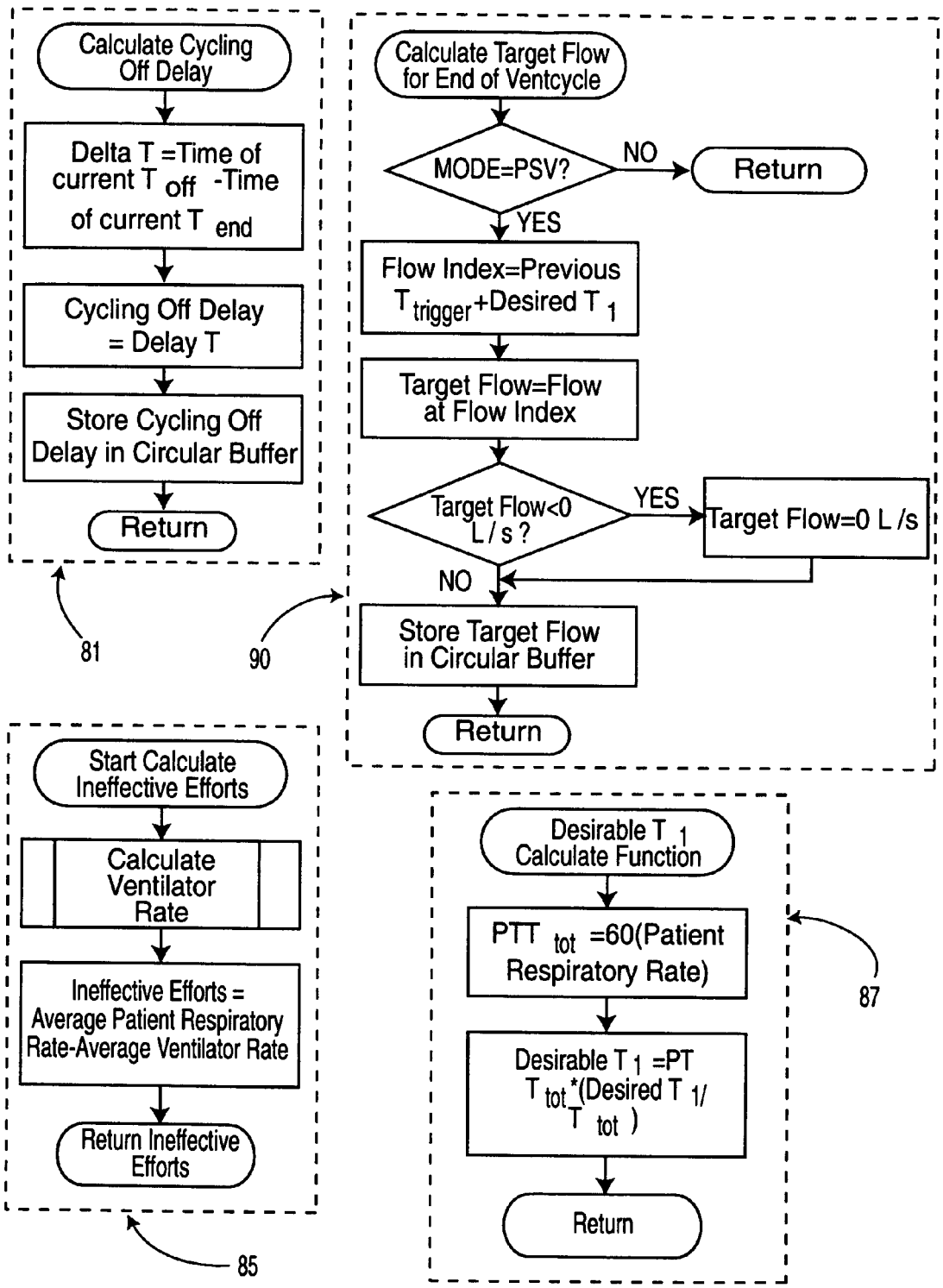
Figure 16:
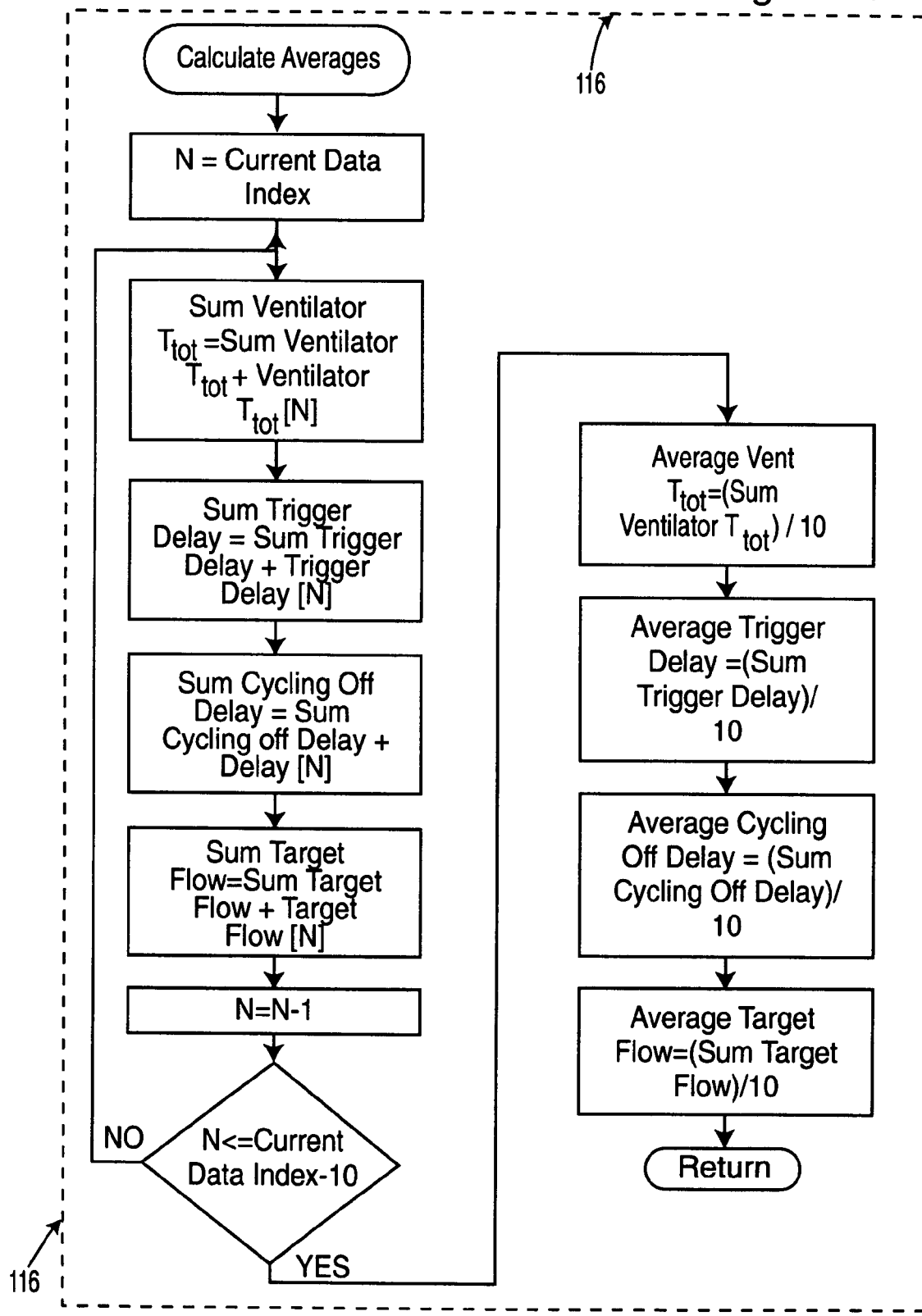
Figure 17:
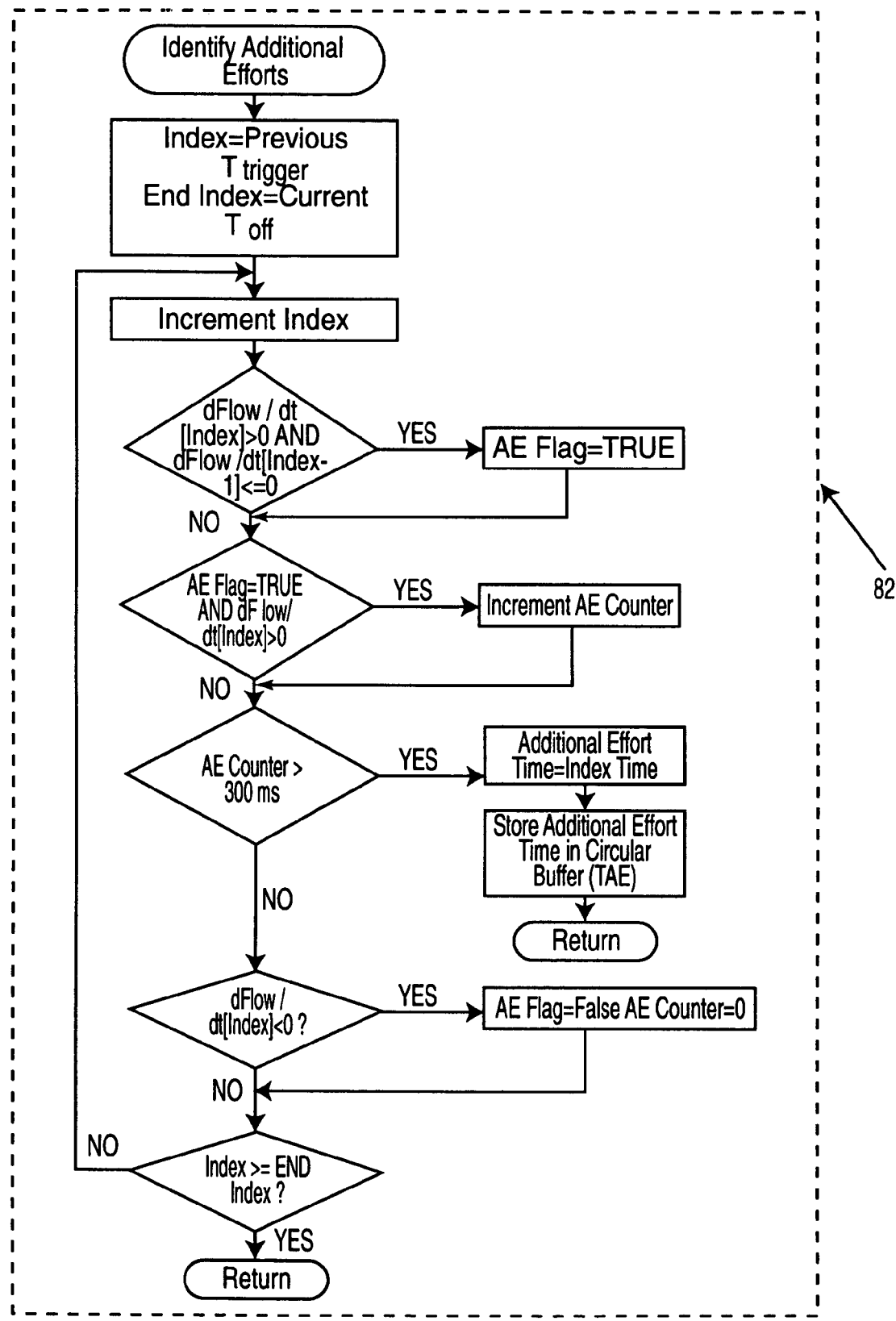
Figure 17:
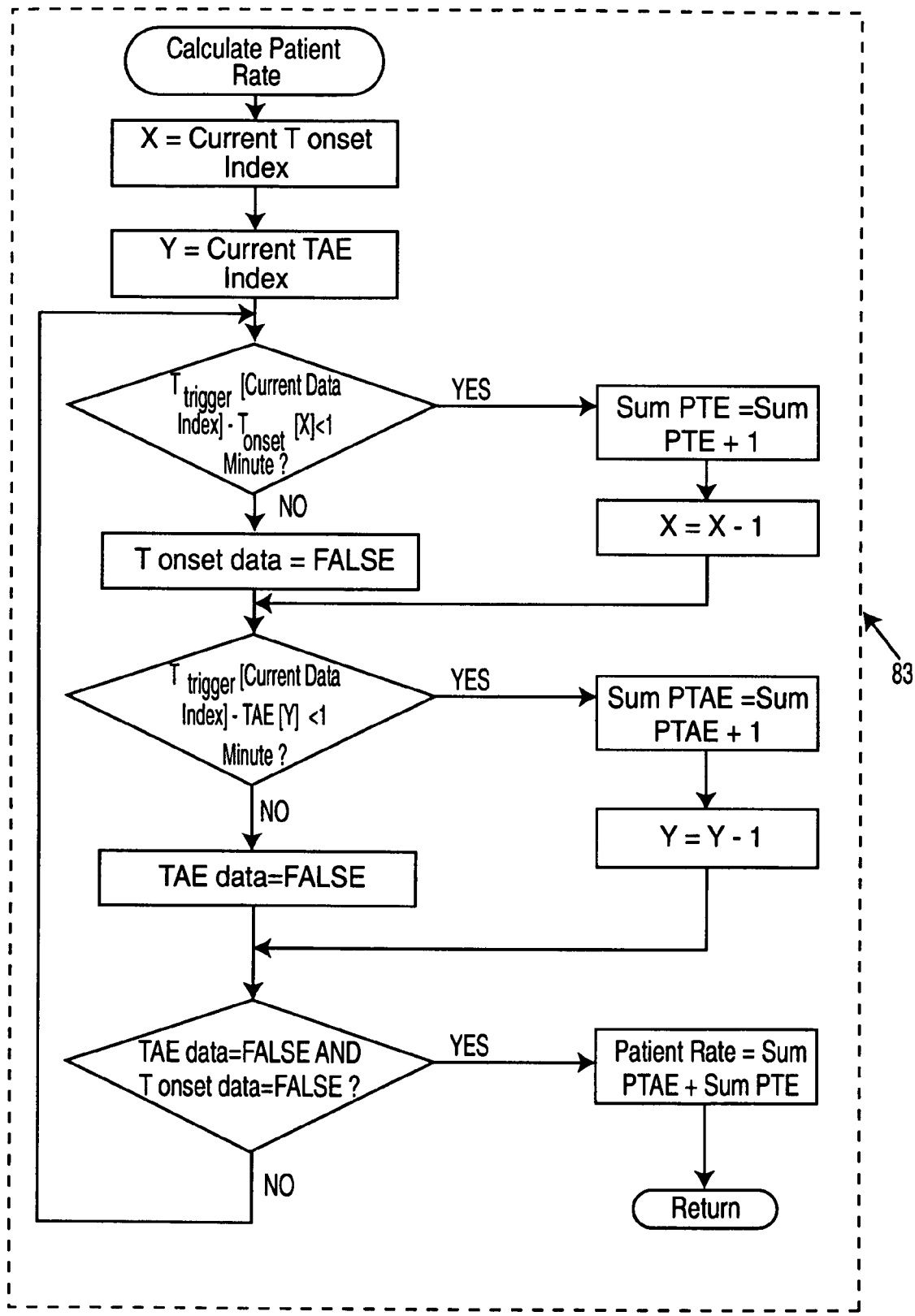

In the illustrated embodiment for calculating target flow to cycle off pressure support ventilation (90, FIG. 16) the point chosen to measure flow was the preceding $T_{trigger}$ plus an interval corresponding to desirable $T_I$, with the latter based on desired $T_I/T_{TOT}$ and average respiratory cycle of patient efforts (87, FIG. 16). There are, however, several other options for selecting the point in time at which to measure flow. These include, but are not limited to:

a. Desirable $T_I$ is added to the $T_{onset}$ preceding the previous $T_{trigger}$ instead of adding it to $T_{trigger}$ itself.
b. Desirable $T_I$ is added to a point in time between previous $T_{trigger}$ and the preceding $T_{onset}$.
c. Desirable $T_I$ is calculated from desired $T_I/T_{TOT}$ fraction of the $T_{TOT}$ of the individual patient cycle that included the previous $T_{trigger}$. This value is then added to the previous $T_{trigger}$, the preceding $T_{onset}$ or some intermediate time.

Each of these options has advantages and disadvantages. In practice, the difference in net result should be small. However, some manufacturers or users may prefer one or the other or even a completely different option.

The resulting output of such microprocessor (FIG. 9) are displayed on a monitor. The information provided can be utilized by the user to adjust ventilator settings in order to optimize patient-ventilator interaction. Alternatively, or in addition, some of the outputs can be channelled to the cycling mechanism of the ventilator to effect such optimization automatically. Of particular utility is the use of information provided by the Desirable $T_I$ function 87 to automatically set the duration of the inflation phase of the ventilator. Likewise, the output of the Target Flow for End of Cycle in the pressure support mode 90 can be used to automatically determine the flow threshold at which the ventilator cycles off in this mode. Other examples of use of generated data include, but are not limited to, increasing the flow threshold for cycling off pressure support when the Cycling off Delay function 81 produces large positive values or when the Calculate Ineffective Efforts function 85 indicates a large number or fraction of such efforts. The magnitude of pressure support (i.e. amount of increase in pressure at triggering) may also be automatically decreased in the presence of long trigger delays, as unveiled by the Calculate Trigger Delay function 80, long and positive Cycling off Delays (per 81) or excessive ineffective efforts (per 85). Microprocessor output can thus be used for closed loop control of amplitude and duration of ventilator assist.

Figure 18:
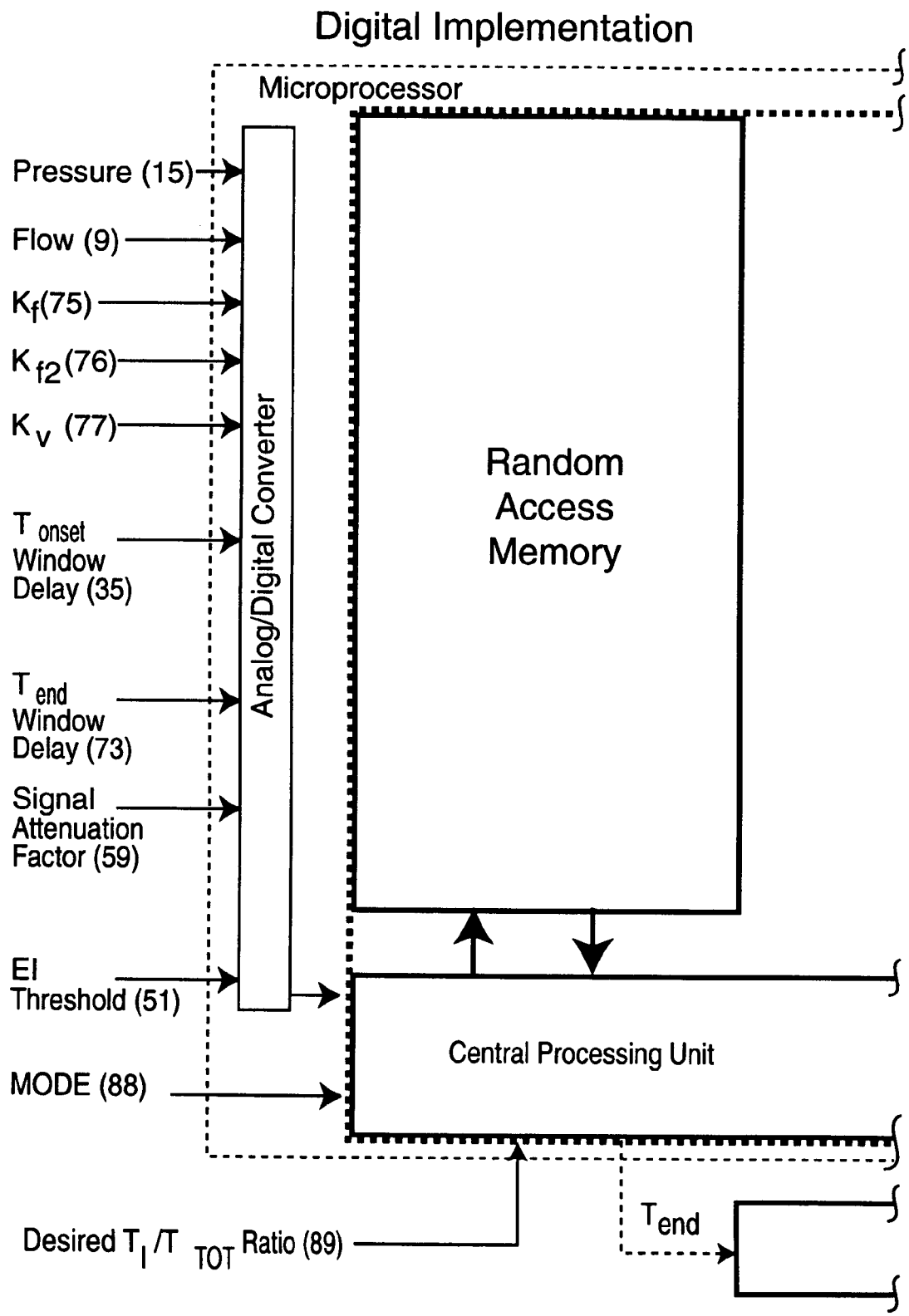
FIG. 18 is a block diagram of one embodiment of a fully digital device for carrying out the method of the invention.
Figure 18:
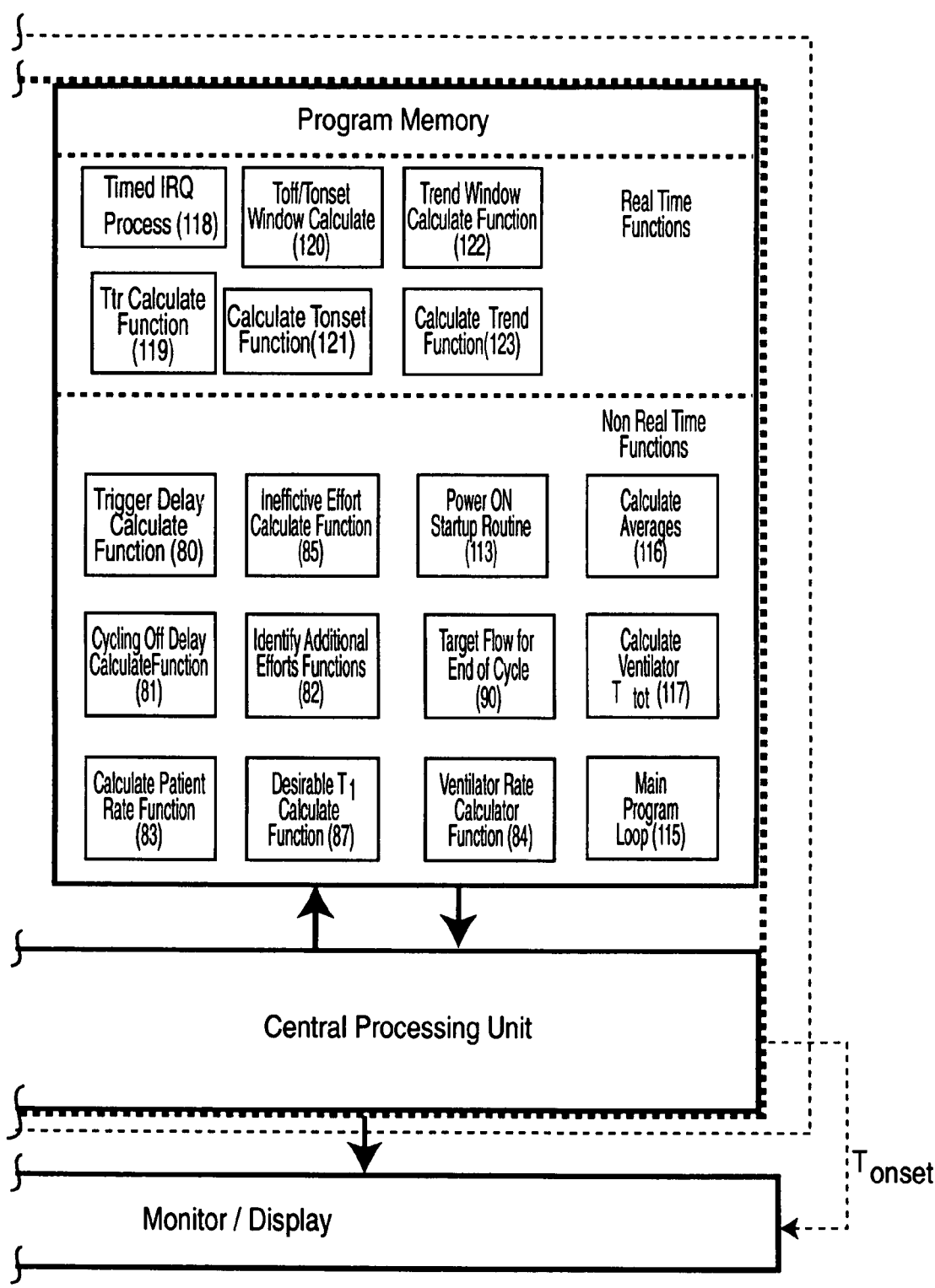
Figure 19:
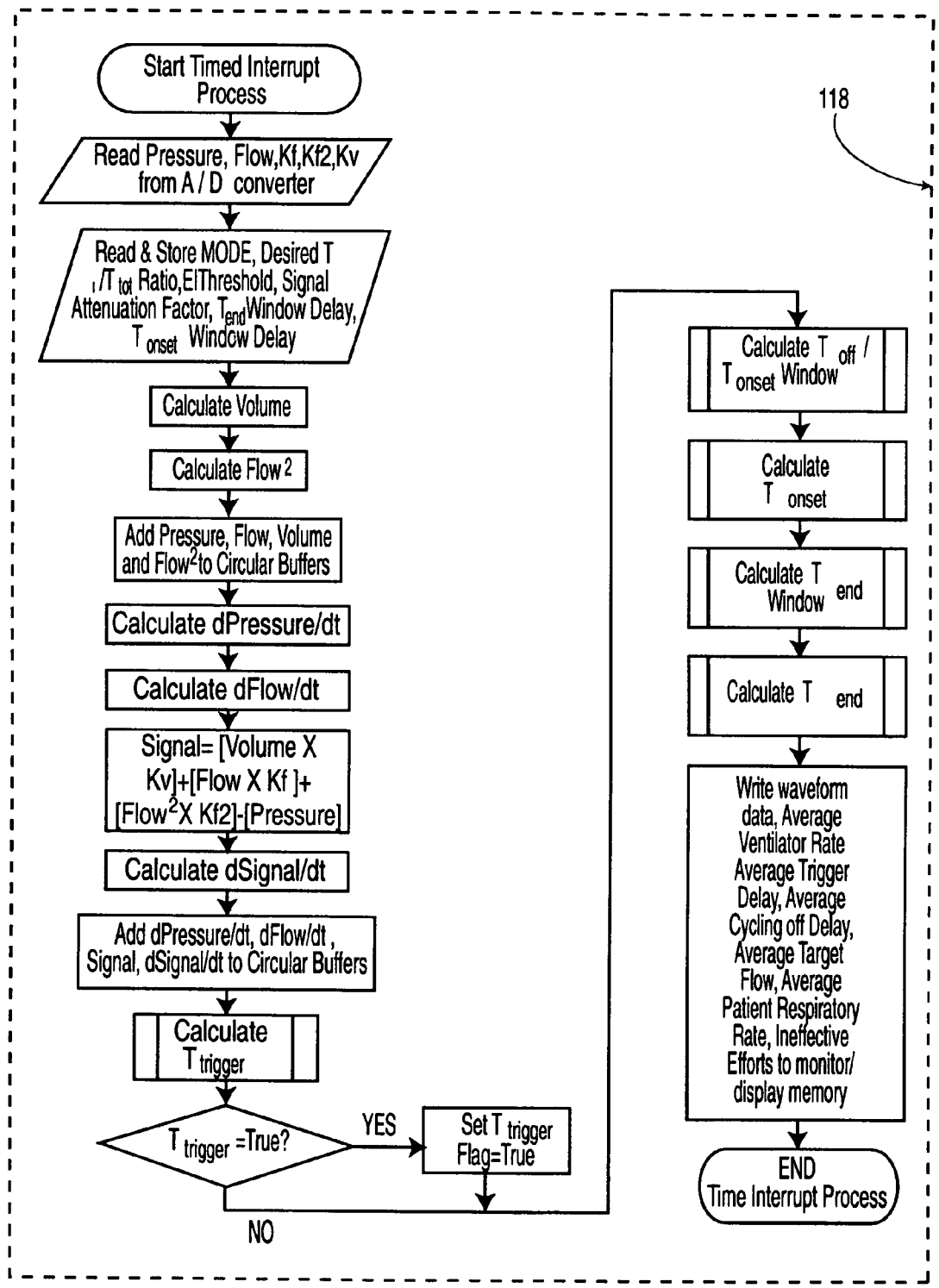
FIGS. 19 to 21 contain flow charts for the different functions performed by the fully digital device of FIG. 18.
Figure 19:
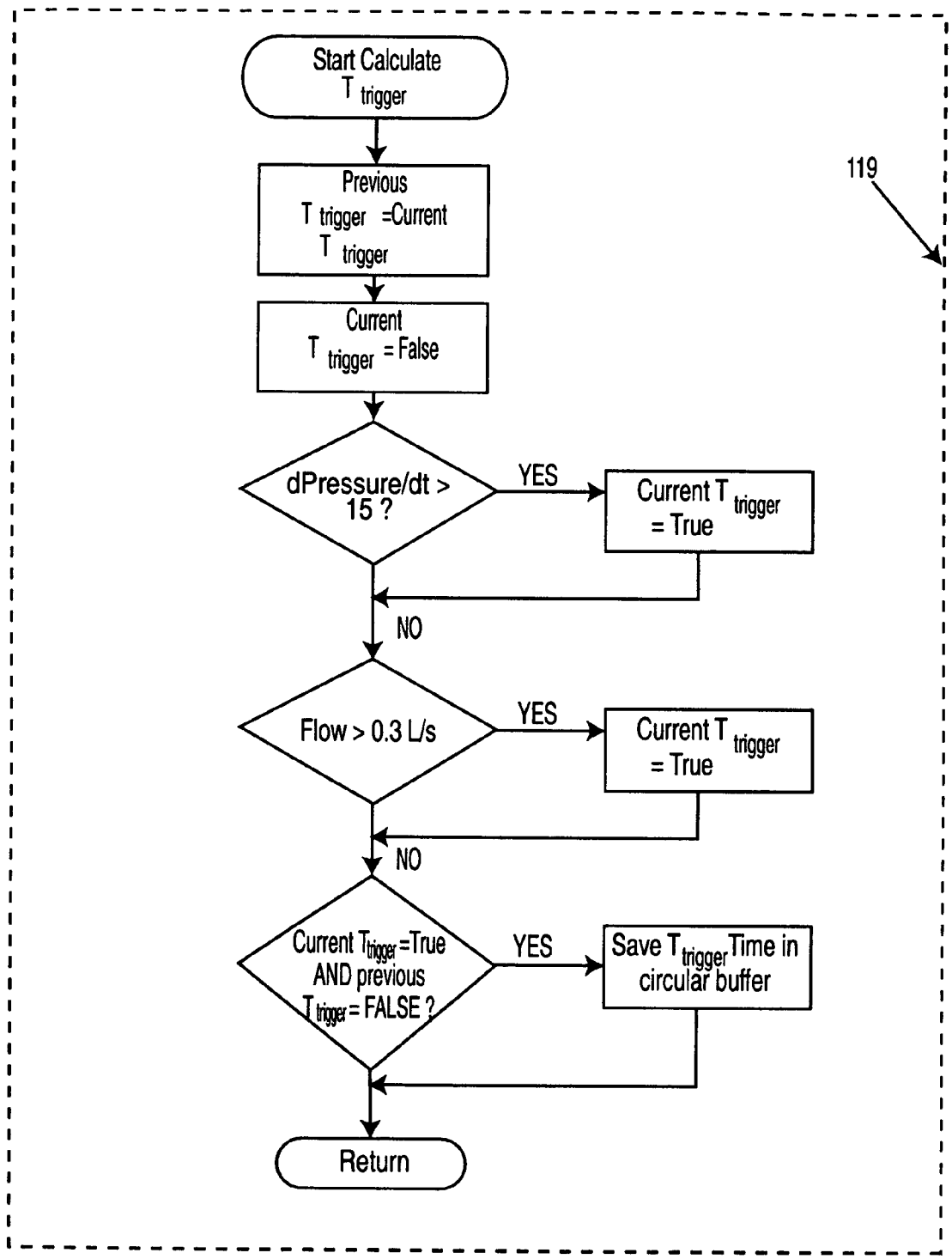
Figure 20:
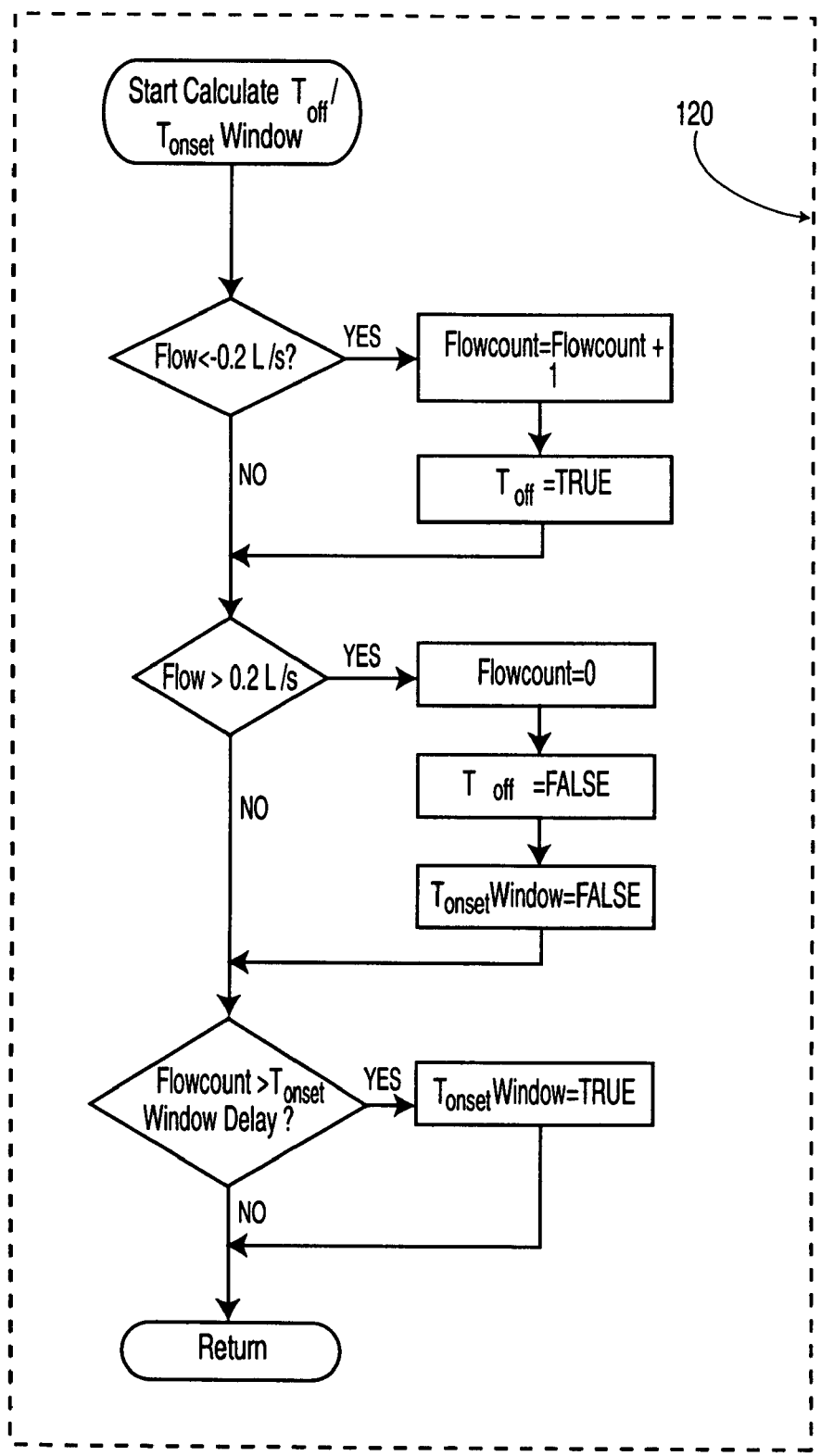
Figure 20:
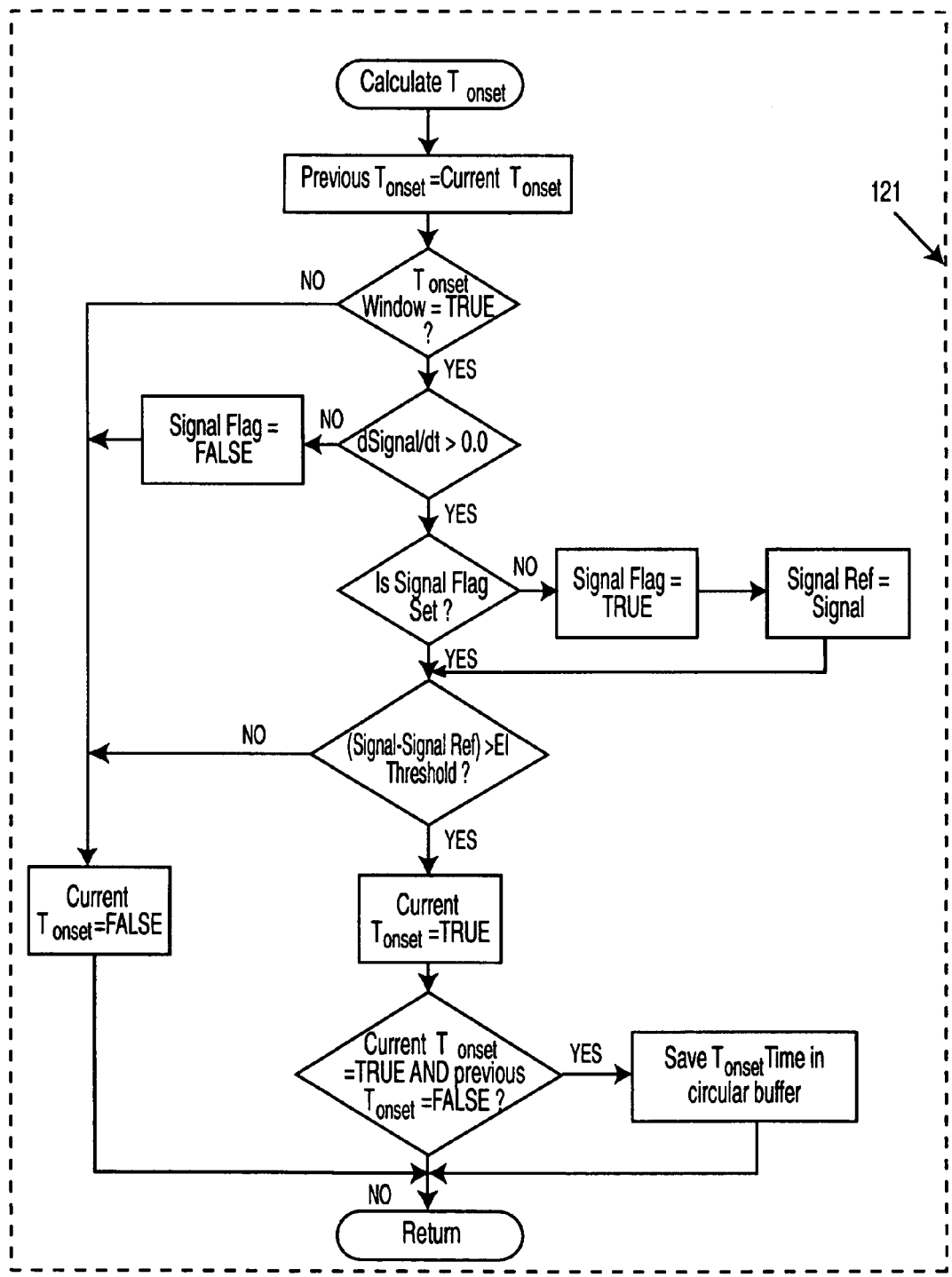
Figure 21:
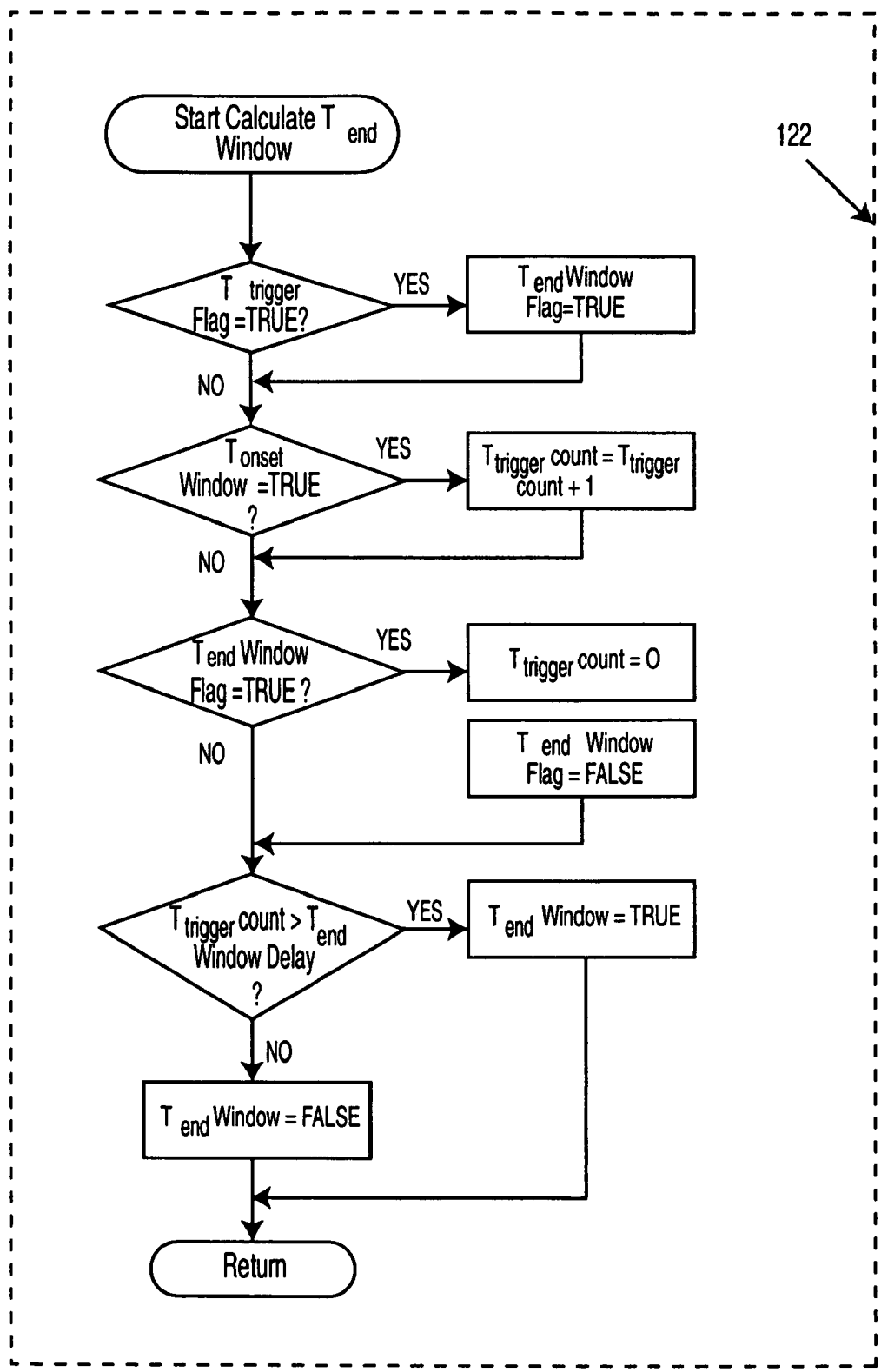
Figure 21:
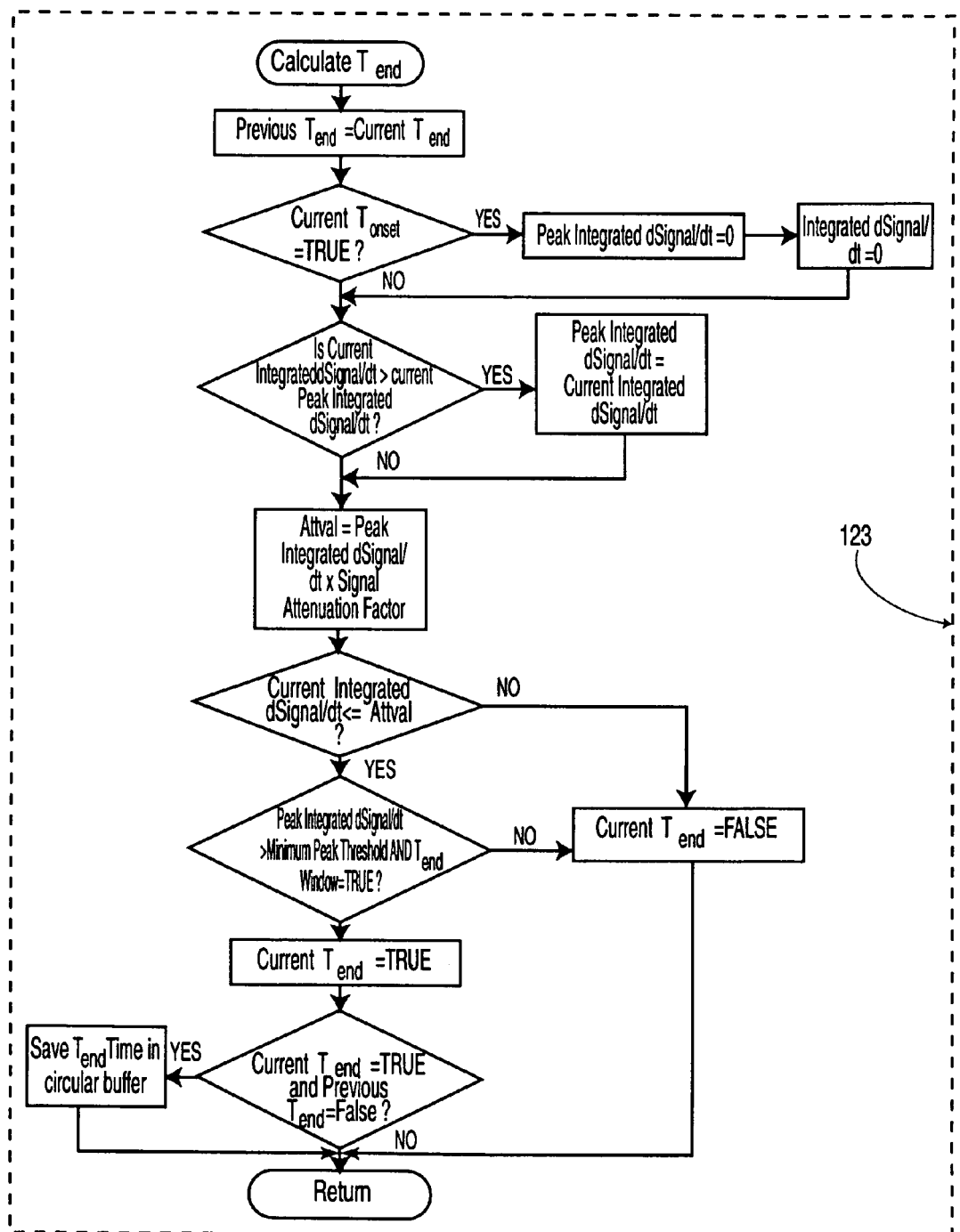

Whereas the preferred embodiment described herein utilized electrical circuitry to generate the Signal and to determine $T_{onset}$ and $T_{end}$, it is clear that any and all the functions executed by electrical circuitry for the current application can be readily executed by digital technology. FIG. 18 is a block diagram illustrating one embodiment of a fully digital device. The device receives the various inputs either via an A/D converter or directly to the central processing unit (CPU) depending on whether the primary inputs are in digital or analog form. In its most comprehensive form, these inputs include pressure 15, flow 9, $K_f$ 75, $K_{f2}$ 76, $K_v$ 77, $T_{onset}$ window delay 35, $T_{end}$ window delay 73, Signal attenuation factor 59, EI threshold 51, Mode 88 and desired $T_I/T_{TOT}$ 89. The microprocessor executes some functions in real time and others in non real time when a $T_{trigger}$ is identified. The non real time functions are similar to those described in detail in relation to the output microprocessor of FIG. 9 and the associated flow charts of FIGS. 13 to 17. These will not be described further. The real time functions are executed at suitable intervals; every 5 to 10 msec being optimal. The timed IRQ process 118 is illustrated in flow chart form in FIG. 19. After reading and storing the various inputs, it calculates volume and flow². The rate of change in pressure is calculated for use in the Calculate $T_{trigger}$ function 119 and the rate of change in flow is calculated for use in the Identify Additional Efforts function 82. The main Signal is then calculated according to Equation 4 and Signal is differentiated for use in the $T_{onset}$ and $T_{end}$ identification functions 121,123. $T_{trigger}$ is then looked for using a $T_{trigger}$ calculate function 119 and, if found, the Trigger flag is set to TRUE. This initiates the non real time functions. Subsequently, the $T_{onset}$ Window calculate function 120 is used to determine whether this window is open and, if so, the Calculate $T_{onset}$ function 121 is processed to determine whether a $T_{onset}$ occurred. Finally, the Calculate $T_{end}$ Window function 122 and the Calculate $T_{end}$ function 123 are processed to identify if a $T_{end}$ occurred. The $T_{trigger}$ calculate function 119, $T_{onset}$ Window calculate function 120, Calculate $T_{onset}$ function 121, Calculate $T_{end}$ Window function 122, and the Calculate $T_{end}$ function 123 are illustrated in flow chart format in FIGS. 19 to 21. These charts are self-explanatory particularly in light of the detailed description of the same functions in relation to the block diagram (FIG. 8) and circuit diagrams (FIGS. 11 and 12) of the analog implementation.

As in the case of the analog implementation, the digital implementation can be simplified to different degrees depending on user and manufacturer preferences. The outputs of the device may also be expanded or reduced to meet user needs.

SUMMARY OF DISCLOSURE

In summary of this disclosure, the present invention provides a method and apparatus for detecting the onset and the end of inspiratory effort in a patient on mechanical ventilation. Modifications are possible within the scope of the invention.

What I claim is:

1. A method for detecting the onset of inspiratory effort ($T_{onset}$) in a patient on mechanical ventilation, comprising the steps of:
   (a) monitoring airway pressure, rate of gas flow, and volume of gas flow of the patient;
   (b) applying a gain factor ($K_f$) to the signal representing rate of gas flow to convert the gas flow signal into a gas flow pressure signal;
   (c) applying a gain factor ($K_v$) to the signal representing volume of gas flow, also to convert the gas volume signal into a gas volume pressure signal;
   (d) generating a composite pressure signal comprising the sum of airway pressure signal, gas flow pressure signal, and gas volume pressure signal, with all signals having suitably adjusted polarity;
   (e) adjusting $K_f$ and $K_v$ to result in a desired linear trajectory of composite pressure signal baseline in the latter part of the exhalation phase;
   (f) comparing (i) current composite pressure signal values with selected earlier composite pressure signal values, and/or
       (ii) current composite pressure signal values with values expected at current time based on extrapolation of composite pressure signal trajectory at specified earlier times, and/or
       (iii) the current rate of change in the composite pressure signal with a selected earlier rate of change in the composite pressure signal;
   (g) comparing differences obtained from such comparison(s) made in step (f) with selected threshold values; and
   (h) identifying $T_{onset}$ when at least one of said differences exceeds said threshold values.

2. The method of claim 1 wherein the composite pressure signal incorporates a fourth component, consisting of the square of the rate of gas flow, to which a gain factor ($K_{f2}$) is applied to convert said fourth signal to a pressure signal and where $K_{f2}$ is also used to adjust the trajectory of composite pressure signal baseline in the latter part of the exhalation phase.

3. The method of claim 2 wherein $K_{f2}$ is assigned a value corresponding to the $K_2$ constant of the endotracheal tube in place in the patient.

4. The method of claim 1 wherein $K_v$, $K_f$ and/or $K_{f2}$ are adjusted to result in a specified slope or pattern of composite pressure signal during part or all of the expiratory phase.

5. The method of claim 1 wherein a default value of $K_f$ is used while the value of $K_v$ is adjusted to obtain a desired baseline composite pressure signal trajectory.

6. The method of claim 1 wherein a default value of $K_v$ is used while the value of $K_f$ is adjusted to obtain a desired baseline composite pressure signal trajectory.

7. The method of claim 1 wherein the $K_f$ value used is a known or estimated value of respiratory system resistance of the patient.

8. The method of claim 1 wherein the $K_v$ value used is a known or estimated value of respiratory system elastance of the patient.

9. The method of claim 1 wherein current composite pressure signal value is compared with the composite pressure signal value at the most recent point where the composite pressure signal began a new rising phase and $T_{onset}$ is identified when the calculated difference exceeds a set threshold value.

10. The method of claim 1 wherein $T_{onset}$ detection is precluded in the early part of the exhalation phase.

11. The method of claim 1 wherein composite pressure signal amplitude is monitored through the inspiratory phase and wherein the end of inspiratory effort ($T_{end}$) is identified from a reduction in composite pressure signal amplitude, or composite pressure signal slope, below a specified value.

12. The method of claim 11 wherein said specified value is a specified fraction of the highest value obtained earlier during said inspiratory phase.

13. The method of claim 11 wherein $T_{end}$ detection is precluded in the early, part of the inflation phase.

14. The method of claim 11 wherein signals corresponding to $T_{end}$ are used to cycle off ventilator cycles.

15. The method of claim 1 wherein generated signals representing $T_{onset}$ are used to trigger ventilator cycles.

16. A method for detecting the onset of inspiratory effort ($T_{onset}$) in a patient on mechanical ventilation, comprising the steps of:
 (a) monitoring airway pressure and rate of gas flow of the patient;
 (b) applying a gain factor ($K_f$) to the signal representing rate of gas flow to convert the gas flow signal into a gas flow pressure signal;
 (c) generating a composite pressure signal comprising the sum of airway pressure signal and the gas flow pressure signal, with the two signals having suitably adjusted polarity;
 (d) comparing (i) the current composite pressure signal values with values expected based on extrapolation of composite pressure signal trajectory at specified earlier times, and/or
  (ii) the current rate of change of composite pressure signal with a selected earlier rate of change of composite pressure signal;
 (e) comparing differences obtained from such comparison(s) made in step (d) with selected threshold values; and
 (f) identifying $T_{onset}$ when at least one of said differences exceeds said threshold values.

17. The method of claim 16 wherein composite pressure signal incorporates a third component, consisting of the square of the rate of gas flow, to which a gain factor ($K_{f2}$) is applied to convert said third signal to a pressure signal.

18. The method of claim 16 wherein selected $K_f$ is known or assumed value of respiratory system resistance.

19. The method of claim 16 wherein generated signals representing $T_{onset}$ are used to trigger ventilator cycles.

20. A device for detecting the onset of inspiratory effort ($T_{onset}$) in a patient on mechanical ventilation, comprising:
 circuitry for measuring airway pressure, rate of gas flow and volume of gas flow of the patient;
 amplifier to apply a gain factor ($K_f$) to the signal representing rate of gas flow to convert said signal into a gas flow pressure signal;
 amplifier to apply a gain factor ($K_v$) to the signal representing volume of gas flow to convert said signal into a gas volume pressure signal;
 summing amplifier that generates a composite pressure signal comprising the sum of airway pressure signal, the gas flow pressure signal, and the gas volume pressure signal, with all signals having suitably adjusted polarity;
 means to permit adjustment of $K_f$ and $K_v$ to provide a desired trajectory of composite pressure signal baseline in the latter part of the exhalation phase;
 circuitry to direct said composite pressure signal to a $T_{onset}$ identification circuitry during a suitable period in the expiratory phase, said identification circuitry comprising circuitry to detect a change in trajectory; and
 means for generating a signal corresponding to $T_{onset}$ when measured change in trajectory of composite pressure signal exceeds a specified threshold.

21. The device of claim 20 wherein an additional signal is generated to be summed by summing amplifier, said additional signal being generated by multiplying the flow signal by the absolute value of the flow signal and applying a gain factor ($K_{f2}$) to the resulting squared flow signal using an amplifier and wherein $K_{f2}$ is also used to adjust the trajectory of composite pressure signal baseline in the latter part of the exhalation phase.

22. The device of claim 21 wherein $K_{f2}$ is assigned a value corresponding to the $K_2$ constant of the endotracheal tube in place in the patient.

23. The device of claim 20 wherein $K_f$ is fixed at a default value while adjustment of signal trajectory is made using $K_f$ and/or $K_{f2}$.

24. The device of claim 20 wherein $K_v$ is fixed at a default value while adjustment of signal trajectory is made using $K_f$ and/or $K_{f2}$.

25. The device of claim 20 wherein the summing amplifier input related to the volume of gas flow is omitted.

26. The device of claim 20 including circuitry that precludes $T_{onset}$ identification during a specified period after the end of ventilator's inflation phase.

27. The device of claim 20 wherein the $T_{onset}$ identification circuitry comprises circuitry to obtain the rate of change in amplitude of the composite pressure signal and to obtain the difference between current said rate of change with said rate of change of the composite pressure signal at a specified earlier time, and to generate a $T_{onset}$ signal when said difference exceeds a set threshold value.

28. The device of claim 20 wherein the $T_{onset}$ identification circuitry comprises circuitry to measure the difference between current amplitude of the composite pressure signal and signal amplitude of the composite pressure signal at a specified earlier time, and to generate a $T_{onset}$ signal when said difference exceeds a set threshold value.

29. The device of claim 20 wherein $K_v$ and/or $K_f$ and/or $K_{f2}$ are adjusted to produce a horizontal or slightly downward sloping composite pressure signal baseline in the latter part of expiration and the $T_{onset}$ identification circuitry comprises circuitry to measure the difference between current amplitude of the composite pressure signal and amplitude of the composite pressure signal at the most recent point where the composite pressure signal began rising, and to generate a $T_{onset}$ signal when said difference exceeds a set threshold value.

30. The device of claim 20 wherein the generated composite pressure signal is gated to circuitry to identify end of inspiratory effort ($T_{end}$) said circuitry comprising:
 circuitry to identify the highest amplitude (peak) of the composite pressure signal reached during the current inspiratory effort;

circuitry to detect when amplitude of the composite pressure signal decreases below a specified value beyond the time at which said peak occurred; and circuitry to generate a signal corresponding to $T_{end}$ when said amplitude of the composite pressure signal decreases below said specified value.

31. The device of claim 30 where said specified value is a specified fraction of peak amplitude of the composite pressure signal.

32. The device of claim 30 wherein circuitry is provided to preclude detection of $T_{end}$ during a specified period following ventilator triggering.

33. The device of claim 20 wherein signals corresponding to $T_{onset}$ are used to trigger ventilator cycles and/or signals corresponding to $T_{end}$ are used to cycle off inflation phase of ventilator.

* * * * *